(12) United States Patent
Williams et al.

(10) Patent No.: US 10,208,341 B2
(45) Date of Patent: Feb. 19, 2019

(54) METHOD OF DETERMINING THE NUCLEOTIDE SEQUENCE OF OLIGONUCLEOTIDES AND DNA MOLECULES

(71) Applicant: LIFE TECHNOLOGIES CORPORATION, Carlsbad, CA (US)

(72) Inventors: Peter Williams, Phoenix, AZ (US); Daniel J. B. Williams, Tempe, AZ (US); Linda Bloom, Gainesville, FL (US); Thomas J. Taylor, Tempe, AZ (US)

(73) Assignee: Life Technologies Corporation, Carsbad, CA (US)

( * ) Notice: Subject to any disclaimer, the term of this patent is extended or adjusted under 35 U.S.C. 154(b) by 631 days.

(21) Appl. No.: 14/268,254

(22) Filed: May 2, 2014

(65) Prior Publication Data

US 2014/0342365 A1    Nov. 20, 2014

Related U.S. Application Data

(63) Continuation of application No. 12/969,872, filed on Dec. 16, 2010, now Pat. No. 9,096,898, which is a continuation of application No. 11/929,141, filed on Oct. 30, 2007, now Pat. No. 7,875,440, which is a continuation of application No. 10/709,436, filed on May 5, 2004, now Pat. No. 7,645,596, which is a continuation of application No. 09/941,882, filed on Aug. 28, 2001, now Pat. No. 6,780,591, which is a continuation-in-part of application No. 09/673,544, filed as application No. PCT/US99/09616 on Apr. 30, 1999, now abandoned.

(60) Provisional application No. 60/083,840, filed on May 1, 1998.

(51) Int. Cl.

| C12Q 1/68 | (2018.01) |
|---|---|
| C12Q 1/6869 | (2018.01) |
| C12Q 1/6816 | (2018.01) |
| C12Q 1/6825 | (2018.01) |
| G01N 33/573 | (2006.01) |
| G01N 33/68 | (2006.01) |

(52) U.S. Cl.
CPC ......... *C12Q 1/6869* (2013.01); *C12Q 1/6816* (2013.01); *C12Q 1/6825* (2013.01); *G01N 33/573* (2013.01); *G01N 33/6863* (2013.01); *C12Q 2533/101* (2013.01); *C12Q 2563/103* (2013.01); *C12Q 2563/107* (2013.01); *C12Q 2563/116* (2013.01); *C12Q 2565/301* (2013.01); *C12Q 2565/629* (2013.01)

(58) Field of Classification Search
CPC .................................................. C12Q 1/6869
USPC ................................................. 435/6.1, 91.1
See application file for complete search history.

(56) References Cited

U.S. PATENT DOCUMENTS

| 3,996,345 A | 12/1976 | Ullman et al. |
|---|---|---|
| 4,021,307 A | 5/1977 | Mosbach |
| 4,119,368 A | 10/1978 | Yamazaki |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Koester et al. |
| 4,739,044 A | 4/1988 | Stabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand |
| 4,942,124 A | 7/1990 | Church |
| 4,962,037 A | 10/1990 | Jett et al. |
| 4,971,903 A | 11/1990 | Hyman |

(Continued)

FOREIGN PATENT DOCUMENTS

| DE | 4141178 | 6/1993 |
|---|---|---|
| DE | 10256898 | 9/2004 |

(Continued)

OTHER PUBLICATIONS

Margulies et al. and supplemental files (Nature vol. 437, pp. 376-380, Supplementary Figures pp. 1-12, Supplementary Methods pp. 1-34, and Supplementary Tables pp. 1-6 (2005).*

(Continued)

*Primary Examiner* — Jezia Riley

(74) *Attorney, Agent, or Firm* — Jones Robb, PLLC

(57) ABSTRACT

The present invention relates to a novel method for analyzing nucleic acid sequences based on real-time detection of DNA polymerase-catalyzed incorporation of each of the four nucleotide bases, supplied individually and serially in a microfluidic system, to a reaction cell containing a template system comprising a DNA fragment of unknown sequence and an oligonucleotide primer. Incorporation of a nucleotide base into the template system can be detected by any of a variety of methods including but not limited to fluorescence and chemiluminescence detection. Alternatively, microcalorimetic detection of the heat generated by the incorporation of a nucleotide into the extending template system using thermopile, thermistor and refractive index measurements can be used to detect extension reactions.

14 Claims, 15 Drawing Sheets

Specification includes a Sequence Listing.

(56) References Cited

U.S. PATENT DOCUMENTS

| | | |
|---|---|---|
| 4,979,824 A | 12/1990 | Mathies et al. |
| 4,994,368 A | 2/1991 | Goodman et al. |
| 4,994,372 A | 2/1991 | Tabor et al. |
| 4,994,373 A | 2/1991 | Stavrianopoulos et al. |
| 5,085,562 A | 2/1992 | Van Lintel et al. |
| 5,091,652 A | 2/1992 | Mathies et al. |
| 5,096,388 A | 3/1992 | Weinberg |
| 5,096,554 A | 3/1992 | Chin |
| 5,108,892 A | 4/1992 | Burke |
| 5,112,736 A | 5/1992 | Caldwell et al. |
| RE34,069 E | 9/1992 | Koster et al. |
| 5,143,854 A | 9/1992 | Pirrung et al. |
| 5,167,784 A | 12/1992 | Noolandi |
| 5,171,132 A | 12/1992 | Miyazaki et al. |
| 5,198,540 A | 3/1993 | Koster |
| 5,209,834 A | 5/1993 | Shera |
| 5,224,843 A | 7/1993 | Van Lintel |
| 5,242,796 A | 9/1993 | Prober et al. |
| 5,242,797 A | 9/1993 | Hirschfeld |
| 5,258,506 A | 11/1993 | Urdea et al. |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A | 4/1994 | Cheeseman |
| 5,304,487 A | 4/1994 | Wilding et al. |
| 5,306,403 A | 4/1994 | Vo-Dinh |
| 5,336,062 A | 8/1994 | Richter |
| 5,360,523 A | 11/1994 | Middendorf et al. |
| 5,375,979 A | 12/1994 | Trah |
| 5,376,252 A | 12/1994 | Ekstroem et al. |
| 5,403,709 A | 4/1995 | Agrawal et al. |
| 5,405,747 A | 4/1995 | Jett et al. |
| 5,405,783 A | 4/1995 | Pirrung et al. |
| 5,409,811 A | 4/1995 | Tabor et al. |
| 5,424,186 A | 6/1995 | Fodor et al. |
| 5,436,149 A | 7/1995 | Barnes |
| 5,449,767 A | 9/1995 | Ward et al. |
| 5,476,928 A | 12/1995 | Ward et al. |
| 5,484,701 A | 1/1996 | Cocuzza et al. |
| 5,492,806 A | 2/1996 | Drmanac et al. |
| 5,514,256 A | 5/1996 | Douthart et al. |
| 5,518,900 A | 5/1996 | Nikiforov et al. |
| 5,525,464 A | 6/1996 | Drmanac et al. |
| 5,529,465 A | 6/1996 | Zengerle et al. |
| 5,534,125 A | 7/1996 | Middendorf et al. |
| 5,547,839 A | 8/1996 | Dower et al. |
| 5,547,859 A | 8/1996 | Goodman et al. |
| 5,556,790 A | 9/1996 | Pettit |
| 5,558,991 A | 9/1996 | Trainor |
| 5,599,695 A | 2/1997 | Pease et al. |
| 5,610,287 A | 3/1997 | Nikiforov et al. |
| 5,620,854 A | 4/1997 | Holzrichter et al. |
| 5,631,734 A | 5/1997 | Stern et al. |
| 5,632,957 A | 5/1997 | Heller et al. |
| 5,654,149 A | 8/1997 | Mendoza et al. |
| 5,659,171 A | 8/1997 | Young et al. |
| 5,670,346 A | 9/1997 | Reeve et al. |
| 5,674,716 A | 10/1997 | Tabor et al. |
| 5,675,155 A | 10/1997 | Pentoney, Jr. et al. |
| 5,688,648 A | 11/1997 | Mathies et al. |
| 5,695,940 A | 12/1997 | Drmanac et al. |
| 5,705,018 A | 1/1998 | Hartley |
| 5,707,506 A | 1/1998 | Douthart et al. |
| 5,710,628 A | 1/1998 | Waterhouse et al. |
| 5,712,476 A | 1/1998 | Renfrew et al. |
| 5,733,729 A | 3/1998 | Lipshutz et al. |
| 5,741,640 A | 4/1998 | Fuller |
| 5,741,644 A | 4/1998 | Kambara et al. |
| 5,744,305 A | 4/1998 | Fodor et al. |
| 5,744,312 A | 4/1998 | Mamone et al. |
| 5,750,341 A | 5/1998 | Macevicz |
| 5,753,788 A | 5/1998 | Fodor et al. |
| 5,755,943 A | 5/1998 | Middendorf et al. |
| 5,756,285 A | 5/1998 | Fuller |
| 5,759,014 A | 6/1998 | Van Lintel |
| 5,759,374 A | 6/1998 | Takahashi et al. |
| 5,762,876 A | 6/1998 | Lincoln et al. |
| 5,763,594 A | 6/1998 | Hiatt et al. |
| 5,776,767 A | 7/1998 | Stevens et al. |
| 5,776,782 A | 7/1998 | Tsuji |
| 5,789,168 A | 8/1998 | Leushner et al. |
| 5,795,722 A | 8/1998 | Lacroix et al. |
| 5,795,782 A | 8/1998 | Church et al. |
| 5,807,679 A | 9/1998 | Kamb |
| 5,808,045 A | 9/1998 | Hiatt et al. |
| 5,830,657 A | 11/1998 | Leushner et al. |
| 5,831,070 A | 11/1998 | Pease et al. |
| 5,832,165 A | 11/1998 | Reichert et al. |
| 5,834,758 A | 11/1998 | Trulson et al. |
| 5,836,750 A | 11/1998 | Cabuz |
| 5,837,832 A | 11/1998 | Chee et al. |
| 5,837,860 A | 11/1998 | Anderson et al. |
| 5,846,396 A | 12/1998 | Zanzucchi et al. |
| 5,846,727 A | 12/1998 | Soper et al. |
| 5,853,979 A | 12/1998 | Green et al. |
| 5,858,671 A | 1/1999 | Jones |
| 5,861,287 A | 1/1999 | Metzker et al. |
| 5,863,722 A | 1/1999 | Brenner |
| 5,872,244 A | 2/1999 | Hiatt et al. |
| 5,876,187 A | 3/1999 | Forster et al. |
| 5,876,934 A | 3/1999 | Duthie et al. |
| 5,882,904 A | 3/1999 | Riedl et al. |
| 5,885,813 A | 3/1999 | Davis et al. |
| 5,889,165 A | 3/1999 | Fodor et al. |
| 5,902,723 A | 5/1999 | Dower et al. |
| 5,908,755 A | 6/1999 | Kumar et al. |
| 5,916,747 A | 6/1999 | Gilchrist et al. |
| 5,922,591 A | 7/1999 | Anderson et al. |
| 5,922,608 A | 7/1999 | Farnsworth et al. |
| 5,928,906 A | 7/1999 | Koster |
| 5,928,919 A | 7/1999 | Reha-Krantz et al. |
| 5,945,283 A | 8/1999 | Kwok et al. |
| 5,945,284 A | 8/1999 | Livak et al. |
| 5,945,312 A | 8/1999 | Goodman et al. |
| 5,945,325 A | 8/1999 | Arnold et al. |
| 5,948,614 A | 9/1999 | Chatterjee |
| 5,952,174 A | 9/1999 | Nikiforov et al. |
| 5,954,932 A | 9/1999 | Takahashi et al. |
| 5,958,703 A | 9/1999 | Dower et al. |
| 5,959,781 A | 9/1999 | Kintz et al. |
| 5,959,837 A | 9/1999 | Yu |
| 5,965,446 A | 10/1999 | Ishikawa |
| 5,968,740 A | 10/1999 | Fodor et al. |
| 5,974,164 A | 10/1999 | Chee |
| 5,976,338 A | 11/1999 | Fujita et al. |
| 5,981,186 A | 11/1999 | Gabe et al. |
| 5,981,956 A | 11/1999 | Stern |
| 5,994,058 A | 11/1999 | Senapathy |
| 5,994,085 A | 11/1999 | Cantor |
| 6,002,471 A | 12/1999 | Quake |
| 6,005,663 A | 12/1999 | Waterhouse et al. |
| 6,007,309 A | 12/1999 | Hartley |
| 6,015,714 A | 1/2000 | Baldarelli et al. |
| 6,017,702 A | 1/2000 | Lee et al. |
| 6,018,041 A | 1/2000 | Drmanac et al. |
| 6,020,457 A | 2/2000 | Klimash et al. |
| 6,024,925 A | 2/2000 | Little et al. |
| 6,025,136 A | 2/2000 | Drmanac |
| 6,028,190 A | 2/2000 | Mathies et al. |
| 6,030,782 A | 2/2000 | Anderson et al. |
| 6,043,080 A | 3/2000 | Lipshutz et al. |
| 6,046,005 A | 4/2000 | Ju et al. |
| 6,049,380 A | 4/2000 | Goodwin et al. |
| 6,051,380 A | 4/2000 | Sosnowski et al. |
| 6,066,454 A | 5/2000 | Lipshutz et al. |
| 6,071,394 A | 6/2000 | Cheng et al. |
| 6,077,664 A | 6/2000 | Slater et al. |
| 6,077,674 A | 6/2000 | Schleifer et al. |
| 6,087,095 A | 7/2000 | Rosenthal et al. |
| 6,087,099 A | 7/2000 | Gupte et al. |
| 6,094,274 A | 7/2000 | Yokoi |
| 6,107,032 A | 8/2000 | Kilger et al. |
| 6,107,044 A | 8/2000 | Nikiforov |

(56) References Cited

U.S. PATENT DOCUMENTS

| | | |
|---|---|---|
| 6,107,061 A | 8/2000 | Johnson |
| 6,132,580 A | 10/2000 | Mathies |
| 6,133,436 A | 10/2000 | Koster et al. |
| 6,136,212 A | 10/2000 | Mastrangelo et al. |
| 6,136,543 A | 10/2000 | Anazawa et al. |
| 6,136,962 A | 10/2000 | Shi et al. |
| 6,140,053 A | 10/2000 | Koester |
| 6,140,494 A | 10/2000 | Hamilton et al. |
| 6,141,096 A | 10/2000 | Stern et al. |
| 6,143,151 A | 11/2000 | Middendorf et al. |
| 6,147,205 A | 11/2000 | McGall et al. |
| 6,156,501 A | 12/2000 | McGall et al. |
| 6,165,694 A | 12/2000 | Liu |
| 6,177,249 B1 | 1/2001 | Kwok et al. |
| 6,197,506 B1 | 3/2001 | Fodor et al. |
| 6,197,595 B1 | 3/2001 | Anderson et al. |
| 6,207,381 B1 | 3/2001 | Larsson et al. |
| 6,207,960 B1 | 3/2001 | Stern |
| 6,210,896 B1 | 4/2001 | Chan |
| 6,214,246 B1 | 4/2001 | Craighead |
| 6,214,987 B1 | 4/2001 | Hiatt et al. |
| 6,221,592 B1 | 4/2001 | Schwartz et al. |
| 6,221,654 B1 | 4/2001 | Quake |
| 6,225,052 B1 | 5/2001 | Batz et al. |
| 6,225,062 B1 | 5/2001 | Dunn et al. |
| 6,225,092 B1 | 5/2001 | Klinger et al. |
| 6,225,109 B1 | 5/2001 | Juncosa et al. |
| 6,225,567 B1 | 5/2001 | Kester |
| 6,225,625 B1 | 5/2001 | Pirrung et al. |
| 6,228,593 B1 | 5/2001 | Lipshutz et al. |
| 6,232,075 B1 | 5/2001 | Williams |
| 6,232,103 B1 | 5/2001 | Short |
| 6,235,465 B1 | 5/2001 | Kolberg et al. |
| 6,235,473 B1 | 5/2001 | Friedman et al. |
| 6,242,180 B1 | 6/2001 | Chee |
| 6,242,528 B1 | 6/2001 | Clark et al. |
| 6,245,506 B1 | 6/2001 | Laugharn, Jr. |
| 6,245,507 B1 | 6/2001 | Bogdanov |
| 6,245,518 B1 | 6/2001 | Baier |
| 6,251,610 B1 | 6/2001 | Gupte et al. |
| 6,255,083 B1 | 7/2001 | Williams |
| 6,255,475 B1 | 7/2001 | Kwiatkowski |
| 6,258,533 B1 | 7/2001 | Jones |
| 6,261,775 B1 | 7/2001 | Bastian et al. |
| 6,261,776 B1 | 7/2001 | Pirrung et al. |
| 6,261,848 B1 | 7/2001 | Anderson et al. |
| 6,262,838 B1 | 7/2001 | Montagu |
| 6,263,286 B1 | 7/2001 | Gilmanshin et al. |
| 6,268,152 B1 | 7/2001 | Fodor et al. |
| 6,268,219 B1 | 7/2001 | McBride et al. |
| 6,269,846 B1 | 8/2001 | Overbeck et al. |
| 6,270,644 B1 | 8/2001 | Mathies et al. |
| 6,270,961 B1 | 8/2001 | Drmanac |
| 6,274,320 B1 | 8/2001 | Rothberg et al. |
| 6,274,351 B1 | 8/2001 | Peponnet |
| 6,277,604 B1 | 8/2001 | Peponnet |
| 6,280,939 B1 | 8/2001 | Allen |
| 6,280,954 B1 | 8/2001 | Ulfendahl |
| 6,284,460 B1 | 9/2001 | Fodor |
| 6,287,821 B1 | 9/2001 | Shi et al. |
| 6,294,336 B1 | 9/2001 | Boyce-Jacino et al. |
| 6,294,337 B1 | 9/2001 | Ibaraki |
| 6,306,607 B2 | 10/2001 | Williams et al. |
| 6,309,601 B1 | 10/2001 | Juncosa et al. |
| 6,309,701 B1 | 10/2001 | Barbera-Guillem |
| 6,309,824 B1 | 10/2001 | Drmanac |
| 6,309,836 B1 | 10/2001 | Kwiatkowski |
| 6,309,886 B1 | 10/2001 | Ambrose et al. |
| 6,310,189 B1 | 10/2001 | Fodor et al. |
| 6,312,893 B1 | 11/2001 | Van Ness et al. |
| 6,316,191 B1 | 11/2001 | Drmanac et al. |
| 6,322,968 B1 | 11/2001 | Head et al. |
| 6,331,439 B1 | 12/2001 | Cherukuri et al. |
| 6,333,183 B1 | 12/2001 | Evans et al. |
| 6,335,824 B1 | 1/2002 | Overbeck |
| 6,337,185 B1 | 1/2002 | Asp et al. |
| 6,337,188 B1 | 1/2002 | Head et al. |
| 6,342,326 B1 | 1/2002 | Milton |
| 6,344,325 B1 | 2/2002 | Quake et al. |
| 6,346,379 B1 | 2/2002 | Gelfand et al. |
| 6,346,413 B1 | 2/2002 | Fodor et al. |
| 6,355,420 B1 | 3/2002 | Chan et al. |
| 6,355,432 B1 | 3/2002 | Fodor et al. |
| 6,361,671 B1 | 3/2002 | Mathies et al. |
| 6,361,937 B1 | 3/2002 | Stryer |
| 6,368,562 B1 | 4/2002 | Yao |
| 6,368,699 B1 | 4/2002 | Gilbert et al. |
| 6,383,749 B2 | 5/2002 | Bochkariov et al. |
| 6,387,626 B1 | 5/2002 | Shi et al. |
| 6,395,232 B1 | 5/2002 | McBride |
| 6,395,559 B1 | 5/2002 | Swenson |
| 6,397,150 B1 | 5/2002 | Izmailov |
| 6,399,364 B1 | 6/2002 | Reeve et al. |
| 6,401,267 B1 | 6/2002 | Drmanac et al. |
| 6,403,311 B1 | 6/2002 | Chan |
| 6,403,315 B1 | 6/2002 | Drmanac |
| 6,403,317 B1 | 6/2002 | Anderson |
| 6,403,320 B1 | 6/2002 | Read et al. |
| 6,403,957 B1 | 6/2002 | Fodor et al. |
| 6,404,907 B1 | 6/2002 | Gilchrist et al. |
| 6,406,893 B1 | 6/2002 | Knapp et al. |
| 6,407,858 B1 | 6/2002 | Montagu |
| 6,408,878 B2 | 6/2002 | Unger et al. |
| 6,416,952 B1 | 7/2002 | Pirrung et al. |
| 6,420,169 B1 | 7/2002 | Read et al. |
| 6,423,273 B1 | 7/2002 | O'Mara |
| 6,432,634 B1 | 8/2002 | Digby et al. |
| 6,436,641 B1 | 8/2002 | Izmailov |
| 6,436,646 B1 | 8/2002 | Nikiforov |
| 6,440,664 B1 | 8/2002 | Digby et al. |
| 6,440,722 B1 | 8/2002 | Knapp et al. |
| 6,444,106 B1 | 9/2002 | McBride et al. |
| 6,444,173 B1 | 9/2002 | Sjursen et al. |
| 6,444,424 B1 | 9/2002 | Chatterjee et al. |
| 6,444,461 B1 | 9/2002 | Knapp et al. |
| 6,447,724 B1 | 9/2002 | Jensen et al. |
| 6,448,090 B1 | 9/2002 | McBride |
| 6,451,536 B1 | 9/2002 | Fodor et al. |
| 6,479,267 B1 | 11/2002 | Davis et al. |
| 6,485,690 B1 | 11/2002 | Pfost et al. |
| 6,485,909 B1 | 11/2002 | Hong et al. |
| 6,485,944 B1 | 11/2002 | Church et al. |
| 6,495,363 B2 | 12/2002 | Bogdanov |
| 6,506,560 B1 | 1/2003 | Hughes et al. |
| 6,511,803 B1 | 1/2003 | Church et al. |
| 6,514,706 B1 | 2/2003 | Von et al. |
| 6,521,428 B1 | 2/2003 | Senapathy |
| 6,524,829 B1 | 2/2003 | Seeger |
| 6,528,258 B1 | 3/2003 | Russell |
| 6,528,288 B2 | 3/2003 | Senapathy |
| 6,537,755 B1 | 3/2003 | Drmanac |
| 6,537,757 B1 | 3/2003 | Langmore et al. |
| 6,546,340 B2 | 4/2003 | Lipshutz et al. |
| 6,551,784 B2 | 4/2003 | Fodor et al. |
| 6,551,817 B2 | 4/2003 | Besemer et al. |
| 6,554,987 B1 | 4/2003 | Gilchrist et al. |
| 6,555,349 B1 | 4/2003 | O'Donnell |
| 6,558,945 B1 | 5/2003 | Kao |
| 6,562,566 B1 | 5/2003 | Hoheisel |
| 6,566,059 B1 | 5/2003 | Stanton, Jr. et al. |
| 6,566,515 B1 | 5/2003 | McGall et al. |
| 6,573,047 B1 | 6/2003 | Hung et al. |
| 6,573,374 B1 | 6/2003 | Muehlegger et al. |
| 6,576,424 B2 | 6/2003 | Fodor et al. |
| 6,576,425 B2 | 6/2003 | McGall et al. |
| 6,579,704 B2 | 6/2003 | Short |
| 6,582,923 B2 | 6/2003 | Stanton et al. |
| 6,585,939 B1 | 7/2003 | Dapprich |
| 6,607,888 B2 | 8/2003 | Schwartz et al. |
| 6,610,482 B1 | 8/2003 | Fodor et al. |
| 6,613,513 B1 | 9/2003 | Parce et al. |
| 6,623,928 B2 | 9/2003 | Ness et al. |
| 6,627,748 B1 | 9/2003 | Ju et al. |
| 6,632,655 B1 | 10/2003 | Mehta et al. |

(56) References Cited

U.S. PATENT DOCUMENTS

| | | |
|---|---|---|
| 6,642,001 B1 | 11/2003 | Bolk |
| 6,664,079 B2 | 12/2003 | Ju et al. |
| 6,719,868 B1 | 4/2004 | Schueller et al. |
| 6,750,018 B2 | 6/2004 | Kambara et al. |
| 6,762,048 B2 | 7/2004 | Williams |
| 6,780,591 B2 | 8/2004 | Williams et al. |
| 6,783,938 B2 | 8/2004 | Nygren et al. |
| 6,787,308 B2 | 9/2004 | Balasubramanian et al. |
| 6,818,395 B1 | 11/2004 | Quake et al. |
| 6,908,736 B1 | 6/2005 | Densham et al. |
| 6,911,345 B2 | 6/2005 | Quake et al. |
| 7,008,766 B1 | 3/2006 | Densham |
| 7,037,687 B2 | 5/2006 | Williams et al. |
| 7,056,666 B2 | 6/2006 | Dower et al. |
| 7,211,414 B2 | 5/2007 | Hardin et al. |
| 7,270,951 B1 | 9/2007 | Stemple et al. |
| 7,645,596 B2 | 1/2010 | Williams et al. |
| 7,875,440 B2 | 1/2011 | Williams et al. |
| 8,216,514 B2 | 7/2012 | Williams et al. |
| 8,666,678 B2 | 3/2014 | Davey et al. |
| 9,096,898 B2 | 8/2015 | Williams et al. |
| 9,212,393 B2 | 12/2015 | Williams |
| 2001/0024790 A1 | 9/2001 | Kambara et al. |
| 2001/0036629 A1 | 11/2001 | Dower et al. |
| 2001/0044531 A1 | 11/2001 | McGall et al. |
| 2001/0046681 A1 | 11/2001 | Senapathy |
| 2002/0009744 A1 | 1/2002 | Bogdanov |
| 2002/0012910 A1 | 1/2002 | Weiss et al. |
| 2002/0015961 A1 | 2/2002 | Kwiatkowski et al. |
| 2002/0025529 A1 | 2/2002 | Quake et al. |
| 2002/0032320 A1 | 3/2002 | Burgess et al. |
| 2002/0034792 A1 | 3/2002 | Kilger et al. |
| 2002/0039738 A1 | 4/2002 | Williams et al. |
| 2002/0042112 A1 | 4/2002 | Koster |
| 2002/0045182 A1 | 4/2002 | Singh et al. |
| 2002/0051992 A1 | 5/2002 | Bridgham et al. |
| 2002/0053532 A1 | 5/2002 | Quake et al. |
| 2002/0061529 A1 | 5/2002 | Bridgham et al. |
| 2002/0072055 A1 | 6/2002 | Jones et al. |
| 2002/0086318 A1 | 7/2002 | Manalis et al. |
| 2002/0102586 A1 | 8/2002 | Ju et al. |
| 2002/0102595 A1 | 8/2002 | Davis et al. |
| 2002/0106673 A1 | 8/2002 | Drmanac et al. |
| 2002/0115076 A1 | 8/2002 | Williams et al. |
| 2002/0115092 A1 | 8/2002 | Julius, Jr. et al. |
| 2002/0119484 A1 | 8/2002 | Weidenhammer et al. |
| 2002/0123046 A1 | 9/2002 | Smith et al. |
| 2002/0137046 A1 | 9/2002 | Koster et al. |
| 2002/0137052 A1 | 9/2002 | Bridgham et al. |
| 2002/0137062 A1 | 9/2002 | Williams et al. |
| 2002/0138205 A1 | 9/2002 | Miller |
| 2002/0142329 A1 | 10/2002 | Matray et al. |
| 2002/0142333 A1 | 10/2002 | Gelfand et al. |
| 2002/0146704 A1 | 10/2002 | Head et al. |
| 2002/0146726 A1 | 10/2002 | Matray et al. |
| 2002/0150903 A1 | 10/2002 | Koster et al. |
| 2002/0150938 A1 | 10/2002 | Kneipp et al. |
| 2002/0164629 A1 | 11/2002 | Quake et al. |
| 2002/0168642 A1 | 11/2002 | Drukier et al. |
| 2002/0168678 A1 | 11/2002 | Williams et al. |
| 2002/0172948 A1 | 11/2002 | Perlin et al. |
| 2002/0177129 A1 | 11/2002 | Paabo et al. |
| 2002/0182601 A1 | 12/2002 | Sampson et al. |
| 2002/0192661 A1 | 12/2002 | Paabo |
| 2002/0192662 A1 | 12/2002 | Boyce-Jacino et al. |
| 2002/0192691 A1 | 12/2002 | Drmanac et al. |
| 2002/0197618 A1 | 12/2002 | Sampson et al. |
| 2003/0003272 A1 | 1/2003 | Laguitton et al. |
| 2003/0003498 A1 | 1/2003 | Digby et al. |
| 2003/0008285 A1 | 1/2003 | Fischer |
| 2003/0008413 A1 | 1/2003 | Kim et al. |
| 2003/0017461 A1 | 1/2003 | Singh et al. |
| 2003/0022207 A1 | 1/2003 | Balasubramanian et al. |
| 2003/0027140 A1 | 2/2003 | Ju et al. |
| 2003/0036080 A1 | 2/2003 | Jensen et al. |
| 2003/0044778 A1 | 3/2003 | Goelet et al. |
| 2003/0044779 A1 | 3/2003 | Goelet et al. |
| 2003/0044781 A1 | 3/2003 | Korlach et al. |
| 2003/0044816 A1 | 3/2003 | Denison et al. |
| 2003/0054181 A1 | 3/2003 | Swerdlow et al. |
| 2003/0054361 A1 | 3/2003 | Heller |
| 2003/0058440 A1 | 3/2003 | Scott et al. |
| 2003/0058799 A1 | 3/2003 | Yamakawa et al. |
| 2003/0059778 A1 | 3/2003 | Berlin et al. |
| 2003/0060431 A1 | 3/2003 | Simmonds et al. |
| 2003/0064366 A1 | 4/2003 | Hardin et al. |
| 2003/0064398 A1 | 4/2003 | Barnes et al. |
| 2003/0064483 A1 | 4/2003 | Shaw et al. |
| 2003/0087237 A1 | 5/2003 | Hong et al. |
| 2003/0087300 A1 | 5/2003 | Knapp et al. |
| 2003/0092005 A1 | 5/2003 | Levene et al. |
| 2003/0092007 A1 | 5/2003 | Gibbs et al. |
| 2003/0096258 A1 | 5/2003 | Fu et al. |
| 2003/0100006 A1 | 5/2003 | Senapathy et al. |
| 2003/0104437 A1 | 6/2003 | Barnes et al. |
| 2003/0104466 A1 | 6/2003 | Knapp et al. |
| 2003/0108867 A1 | 6/2003 | Chee et al. |
| 2003/0138809 A1 | 7/2003 | Williams et al. |
| 2003/0143599 A1 | 7/2003 | Makarov et al. |
| 2003/0148344 A1 | 8/2003 | Rothberg et al. |
| 2003/0162213 A1 | 8/2003 | Fuller et al. |
| 2003/0186227 A1 | 10/2003 | Balasubramanian et al. |
| 2003/0186255 A1 | 10/2003 | Williams et al. |
| 2003/0190627 A1 | 10/2003 | Zhao et al. |
| 2003/0190647 A1 | 10/2003 | Odera et al. |
| 2003/0190663 A1 | 10/2003 | Yang et al. |
| 2003/0194722 A1 | 10/2003 | Odedra et al. |
| 2003/0194740 A1 | 10/2003 | Williams et al. |
| 2003/0215862 A1 | 11/2003 | Parce et al. |
| 2004/0009487 A1 | 1/2004 | Kadushin et al. |
| 2004/0014096 A1 | 1/2004 | Anderson et al. |
| 2004/0029115 A9 | 2/2004 | Dower et al. |
| 2004/0038206 A1 | 2/2004 | Zhang et al. |
| 2004/0054162 A1 | 3/2004 | Hanna et al. |
| 2004/0106110 A1 | 6/2004 | Balasubramanian et al. |
| 2004/0126770 A1 | 7/2004 | Kumar |
| 2005/0014175 A1 | 1/2005 | Quake et al. |
| 2005/0032076 A1 | 2/2005 | Williams et al. |
| 2005/0100932 A1 | 5/2005 | Lapidus et al. |
| 2005/0116262 A1 | 6/2005 | Chen et al. |
| 2005/0147992 A1 | 7/2005 | Quake et al. |
| 2005/0170367 A1 | 8/2005 | Quake et al. |
| 2005/0239085 A1 | 10/2005 | Buzby |
| 2006/0205094 A1 | 9/2006 | Akhavan-Tafti et al. |
| 2008/0166727 A1 | 7/2008 | Esfandyarpour et al. |
| 2008/0213770 A1 | 9/2008 | Williams et al. |
| 2011/0183321 A1 | 7/2011 | Williams et al. |
| 2011/0294115 A1 | 12/2011 | Williams et al. |
| 2012/0258449 A1 | 10/2012 | Williams et al. |

FOREIGN PATENT DOCUMENTS

| | | |
|---|---|---|
| EP | 0223618 | 5/1987 |
| EP | 0412883 | 2/1991 |
| EP | 0579997 | 1/1994 |
| EP | 0703364 | 3/1996 |
| EP | 0706004 | 4/1996 |
| EP | 0779436 | 6/1997 |
| EP | 0845603 | 6/1998 |
| EP | 0932700 | 8/1999 |
| EP | 0946752 | 10/1999 |
| EP | 0955085 | 11/1999 |
| EP | 0999055 | 5/2000 |
| EP | 0706004 | 8/2003 |
| GB | 2155152 | 9/1985 |
| GB | 2308460 | 6/1997 |
| GB | 2400518 | 10/2004 |
| SE | 9500589 | 8/1996 |
| WO | 89/03432 | 4/1989 |
| WO | 89/09283 | 10/1989 |
| WO | 90/13666 | 11/1990 |
| WO | 90/15070 | 12/1990 |
| WO | 91/06678 | 5/1991 |
| WO | 92/10092 | 6/1992 |

(56) References Cited

FOREIGN PATENT DOCUMENTS

| | | |
|---|---|---|
| WO | 92/10587 | 6/1992 |
| WO | 93/05183 | 3/1993 |
| WO | 93/06121 | 4/1993 |
| WO | 93/21340 | 10/1993 |
| WO | WO 93/21340 A1 * | 10/1993 |
| WO | 93/23564 | 11/1993 |
| WO | 95/12608 | 5/1995 |
| WO | 95/27080 | 10/1995 |
| WO | 96/04547 | 2/1996 |
| WO | 96/12014 | 4/1996 |
| WO | 96/12039 | 4/1996 |
| WO | 96/12705 | 5/1996 |
| WO | 96/27025 | 9/1996 |
| WO | 96/27432 | 9/1996 |
| WO | 96/36737 | 11/1996 |
| WO | 97/02488 | 1/1997 |
| WO | 97/22076 | 6/1997 |
| WO | 97/23650 | 7/1997 |
| WO | 97/37041 | 10/1997 |
| WO | 97/39150 | 10/1997 |
| WO | 97/40184 | 10/1997 |
| WO | 97/41258 | 11/1997 |
| WO | 97/41259 | 11/1997 |
| WO | 97/42348 | 11/1997 |
| WO | 98/00708 | 1/1998 |
| WO | 98/02575 | 1/1998 |
| WO | 98/03684 | 1/1998 |
| WO | 98/07069 | 2/1998 |
| WO | 98/08440 | 3/1998 |
| WO | 98/08978 | 3/1998 |
| WO | 98/13523 | 4/1998 |
| WO | 98/20019 | 5/1998 |
| WO | 98/20020 | 5/1998 |
| WO | 98/20166 | 5/1998 |
| WO | 98/21361 | 5/1998 |
| WO | 98/27228 | 6/1998 |
| WO | 98/28440 | 7/1998 |
| WO | 98/33939 | 8/1998 |
| WO | 98/40520 | 9/1998 |
| WO | 98/41650 | 9/1998 |
| WO | 98/41657 | 9/1998 |
| WO | 98/44152 | 10/1998 |
| WO | 98/45481 | 10/1998 |
| WO | 98/53300 | 11/1998 |
| WO | 98/54669 | 12/1998 |
| WO | 98/55593 | 12/1998 |
| WO | 99/01768 | 1/1999 |
| WO | 99/05221 | 2/1999 |
| WO | 99/05315 | 2/1999 |
| WO | 99/06422 | 2/1999 |
| WO | 99/09616 | 2/1999 |
| WO | 99/13109 | 3/1999 |
| WO | 99/13110 | 3/1999 |
| WO | 99/17093 | 4/1999 |
| WO | 99/19516 | 4/1999 |
| WO | 99/24797 | 5/1999 |
| WO | 99/27137 | 6/1999 |
| WO | 99/31278 | 6/1999 |
| WO | 99/37810 | 7/1999 |
| WO | 99/39001 | 8/1999 |
| WO | 99/40105 | 8/1999 |
| WO | 99/40223 | 8/1999 |
| WO | 99/41410 | 8/1999 |
| WO | 99/44045 | 9/1999 |
| WO | 99/45153 | 9/1999 |
| WO | 99/47539 | 9/1999 |
| WO | 99/47706 | 9/1999 |
| WO | 99/53423 | 10/1999 |
| WO | 99/57321 | 11/1999 |
| WO | 99/61888 | 12/1999 |
| WO | 99/64437 | 12/1999 |
| WO | 99/64840 | 12/1999 |
| WO | 99/65938 | 12/1999 |
| WO | 99/66076 | 12/1999 |
| WO | 99/66313 | 12/1999 |
| WO | 00/00637 | 1/2000 |
| WO | 00/06770 | 2/2000 |
| WO | 00/09753 | 2/2000 |
| WO | 00/11223 | 3/2000 |
| WO | 00/17397 | 3/2000 |
| WO | 00/26935 | 5/2000 |
| WO | 00/30591 | 6/2000 |
| WO | 00/34523 | 6/2000 |
| WO | 00/37680 | 6/2000 |
| WO | 00/40750 | 7/2000 |
| WO | 00/40758 | 7/2000 |
| WO | 00/42223 | 7/2000 |
| WO | 00/43540 | 7/2000 |
| WO | 00/43752 | 7/2000 |
| WO | 00/50642 | 8/2000 |
| WO | 00/53805 | 9/2000 |
| WO | 00/53812 | 9/2000 |
| WO | 00/56937 | 9/2000 |
| WO | 00/58507 | 10/2000 |
| WO | 00/58516 | 10/2000 |
| WO | 00/68410 | 11/2000 |
| WO | 00/70073 | 11/2000 |
| WO | 00/71755 | 11/2000 |
| WO | 00/79007 | 12/2000 |
| WO | 01/01025 | 1/2001 |
| WO | 01/16375 | 3/2001 |
| WO | 01/23610 | 4/2001 |
| WO | 01/24937 | 4/2001 |
| WO | 01/25480 | 4/2001 |
| WO | 01/31055 | 5/2001 |
| WO | 01/32930 | 5/2001 |
| WO | 01/38574 | 5/2001 |
| WO | 01/42496 | 6/2001 |
| WO | 01/43184 | 6/2001 |
| WO | 01/57248 | 8/2001 |
| WO | 01/57249 | 8/2001 |
| WO | 01/61044 | 8/2001 |
| WO | 01/64838 | 9/2001 |
| WO | 01/75154 | 10/2001 |
| WO | 01/79536 | 10/2001 |
| WO | 01/85991 | 11/2001 |
| WO | 01/92284 | 12/2001 |
| WO | 01/96607 | 12/2001 |
| WO | 02/00343 | 1/2002 |
| WO | 02/02584 | 1/2002 |
| WO | 02/02795 | 1/2002 |
| WO | 02/02813 | 1/2002 |
| WO | 02/03305 | 1/2002 |
| WO | 02/04680 | 1/2002 |
| WO | 02/20836 | 3/2002 |
| WO | 02/20837 | 3/2002 |
| WO | 02/27032 | 4/2002 |
| WO | 02/29106 | 4/2002 |
| WO | 02/30486 | 4/2002 |
| WO | 02/35441 | 5/2002 |
| WO | 02/36832 | 5/2002 |
| WO | 02/44414 | 6/2002 |
| WO | 02/061126 | 8/2002 |
| WO | 02/061127 | 8/2002 |
| WO | 02/072779 | 9/2002 |
| WO | 02/072892 | 9/2002 |
| WO | 02/077694 | 10/2002 |
| WO | 02/079519 | 10/2002 |
| WO | 02/088381 | 11/2002 |
| WO | 02/088382 | 11/2002 |
| WO | 02/097113 | 12/2002 |
| WO | 02/099398 | 12/2002 |
| WO | 03/002767 | 1/2003 |
| WO | 03/016565 | 2/2003 |
| WO | 03/020895 | 3/2003 |
| WO | 03/020968 | 3/2003 |
| WO | 03/021010 | 3/2003 |
| WO | 03/031947 | 4/2003 |
| WO | 03/044678 | 5/2003 |
| WO | 03/048178 | 6/2003 |
| WO | 03/048991 | 6/2003 |
| WO | 03/062897 | 7/2003 |
| WO | 03/106642 | 12/2003 |
| WO | 2004/061119 | 7/2004 |

(56) References Cited

FOREIGN PATENT DOCUMENTS

| WO | 2004/074503 | 9/2004 |
|---|---|---|
| WO | 2005/047523 | 5/2005 |
| WO | 2005/080605 | 9/2005 |

OTHER PUBLICATIONS

Burgess, K., et al., "An Approach to Photolabile, Fluorescent Protecting Groups" *J. Org. Chem.*, vol. 62, No. 15, Jul. 1997, 5165-5168.
C.A. No. 10-735-SLR, "Expert Report of George M. Weinstock, Ph.D.", in *Helicos Biosciences Corp. v. Pacific Biosciences of California*, Mar. 7, 2012, 141 pages.
C.A. No. 10-735-SLR, "Expert Report of Gerald Zon Re: Invalidity of U.S. Pat. No. 7,645,596, U.S. Pat. No. 7,037,687, and U.S. Pat. No. 7,169,560", in *Helicos Biosciences Corp. v. Pacific Biosciences of California*, Mar. 7, 2012, 615 pages.
C.A. No. 10-735-SLR, "Expert Report of Kevin Ulmer Ph.D. in Rebuttal to Expert Report of George M. Weinstock Ph.D. Re: U.S. Pat. No. 7,037,687", in *Helicos Biosciences Corp. v. Pacific Biosciences of California*, Apr. 13, 2012, 65 pages.
C.A. No. 10-735-SLR, "Expert Report of Kevin Ulmer Ph.D. in Rebuttal to Expert Report of Gerald Zon Re: Invalidity of U.S. Pat. No. 7,645,596, U.S. Pat. No. 7,037,687 and U.S. Pat. No. 7,169,560", in *Helicos Biosciences Corp. v. Pacific Biosciences of California*, Apr. 13, 2012, 442 pages.
C.A. No. 10-735-SLR, "Second Supplemental Expert Report of Dr. Gerald Zon", in *Helicos Biosciences Corporation* vs. *Pacific Biosciences of California*, Apr. 30, 2012, 426 pages.
C.A. No. 10-735-SLR, "Supplemental Expert Report of George M. Weinstock, Ph.D.", in *Helicos Biosciences Corp. v. Pacific Biosciences of California*, Apr. 30, 2012, 125 pages.
C.A. No. 10-735-SLR, "Supplemental Expert Report of Gerald Zon Re: Invalidity of U.S. Pat. No. 7,645,596, U.S. Pat. No. 7,037,687, and U.S. Pat. No. 7,169,560", in *Helicos Biosciences Corp. v. Pacific Biosciences of California*, Apr. 6, 2012, 30 pages.
C.A. No. 10-735-SLR, "Supplemental Expert Report of Kevin Ulmer Ph.D. in Rebuttal to Supplemental Expert Report of Gerald Zon Re: Invalidity of U.S. Pat. No. 7,654,596, U.S. Pat. No. 7,037,687, and U.S. Pat. No. 7,169,560", Apr. 27, 2012, 21 pages.
CA2,458,777, Office Action from Canadian IP Office, dated Apr. 26, 2006, 2 pages.
Cook, G.A., et al., "A Rapid, Enzymatic Assay for the Measurement of Inorganic Pyrophosphate in Animal Tissues", *Anal. Biochem.*, vol. 91, 1978, 557-565.
Drake, H.L., et al., "A New, Convenient Method for the Rapid Analysis of Inorganic Pyrophosphate", *Anal. Biochem.*, vol. 94, Apr. 1979, 117-120.
EP02757473, Supplementary European Search Report, dated Feb. 4, 2005, 4 pages.
Garcia, C.A., et al., "Mutation detection by pyrosequencing: sequencing of exons 5-8 of the p53 tumor suppressor gene", *Gene*, vol. 253, No. 2, 2000, 249-257.
Hite, J.M., et al., "Factors affecting fidelity of DNA synthesis during PCR amplification of d(C-A)n d(G-T)n microsatellite repeats", *Nucleic Acids Res.*, vol. 24(12), 1996, 2429-2434.
Hunkapiller, T., et al., "Large-scale and automated DNA sequence determination", *Science*, vol. 254, No. 5028, Oct. 4, 1991, 59-67.
Johnson, J.C., et al., "An Enzymatic Method for Determination of Inorganic Pyrophosphate and Its Use as an Assay for RNA Polymerase", *Anal. Biochem.*, vol. 26, No. 1, 1968, 137-145.
JP2000-547272, Office Action from Japanese Patent Office, dated Dec. 4, 2002, 4 pages.
Klenow, H., et al., "Selective Elimination of the Exonuclease Activity of the Deoxyribonucleic Acid Polymerase from *Escherichia coli* B by Limited Proteolysis", *PNAS*, vol. 65, No. 2, 1970, 168-175.

Ronaghi, M., et al., "Real-time DNA Sequencing Using Detection of Pyrophosphate Release", *Anal. Biochem.*, vol. 242, No. 1, 1996, 84-89.
Ronaghi, M., et al., "A Sequencing Method Based on Real-Time Pyrophosphate", *Science*, vol. 281, 1998, 363-365.
Ronaghi, M., "Pyrosequencing Sheds Light on DNA Sequencing", *Genome Res.*, vol. 11, No. 1, 2001, 3-11.
Sambrook et al., "Large Fragment DNA Polymerase I (Klenow Fragment)" *Molecular Cloning a Laboratory Manual, 2nd edition*, 1989, 3 pages.
Sanger, F., et al., "DNA sequencing with chain-terminating inhibitors", *PNAS*, vol. 74, No. 12, 1977, 5463-5467.
Swamy, A.R., et al., "Near-Infrared Fluorescent Immunoassays: A Novel Approach to Environmental Analysis", Chapter 12 in *Immunochemical Technology for Environmental Applications, ACS Symposium Series*, American Chemical Society, 1997, 146-161.
Tabor, S., et al., "DNA sequence analysis with a modified bacteriophage T7 DNA polymerase", *PNAS*, vol. 84, 1987, 4767-4771.
U.S. Appl. No. 95/001,529, "Declaration of Dr. Jay Trautman Exhibit B to Request for Reexamination of U.S. Pat. No. 7,645,596", Jan. 27, 2011, 65 pages.
U.S. Appl. No. 95/001,529, "Request for Inter Partes Reexamination under 37 C.F.R. § 1.913", Jan. 27, 2011, 91 pages.
U.S. Appl. No. 95/001,529, "Second Declaration of Dr. Jay Trautman Exhibit A to the Third Party Requester Comments under 37 C.F.R. § 1.947 in The Reexamination of U.S. Pat. No. 7,645,596", Jun. 9, 2011, 10 pages.
U.S. Appl. No. 95/001,529, "Third Party Requester Comments under 37 C.F.R. § 1.947", Dec. 21, 2011, 15 pages.
U.S. Appl. No. 95/001,529, "Third Party Requester Comments under 37 C.F.R. § 1.947", Jun. 9, 2011, 33 pages.
U.S. Appl. No. 95/001,532, "Request for Inter Partes Reexamination under 37 C.F.R. § 1.913", Jan. 27, 2011, 183 pages.
U.S. Appl. No. 95/001,532, "Third Party Requester Comments under 37 C.F.R. § 1.947", Dec. 5, 2011, 19 pages.
U.S. Appl. No. 95/001,532, "Third Party Requester Comments under 37 C.F.R. § 1.947", Jul. 13, 2011, 34 pages.
U.S. Appl. No. 95/001,643, "Declaration by Dr. Steven A. Sundberg Under 37 C.F.R. 1.132", Exhibit A5, Nov. 13, 2011, 14 pages.
U.S. Appl. No. 95/001,643, "Declaration of Hesaam Esfandyarpour Under 37 C.F.R. 1.132", Exhibit 2, Feb. 18, 2010, 3 pages.
U.S. Appl. No. 95/001,643, "Request for Inter Partes Reexamination of U.S. Pat. No. 7,875,440", Jun. 7, 2011, 232 pages.
U.S. Appl. No. 95/001,643, Inter Partes Reexamination Communication, Aug. 17, 2011, 29 pages.
U.S. Appl. No. 95/001,643, "Third Party Requester Comments to Patent Owner's Response to Action Closing Prosecution", Jul. 31, 2012, 32 pages.
U.S. Appl. No. 95/001,643, "Third Party Requester's Comments to Patentee's Amendment and Response to Office Action in Inter Partes Reexamination under 37 C.F.R. § 1.947", Nov. 14, 2011, 50 pages.
"Promega's Protocols and Applications Guide on PCR Amplification, 2011", Available at http:///www.promega.com/resources/product-guidesand-selectors/protocols-and-applications-guide/pcr-amplification/, 2011, 34 pages.
"Therminator DNA Polymerase FAQ", http://www.neb.com/nebecomm/products/faqproductM0261.asp, Jun. 1, 2005, 1 page.
"Ullman's Encyclopedia of industrial Chemistry", *Subject: Carbon Black, Wiley-VCH, 6ID Edition*, vol. 6, Sections 6 to 6.3, 1999.
Adam, et al., "Individual genomes targeted in sequencing revolution", *Nature*, vol. 411, May 2001, 402.
Agrawal, S. et al., "Site-specific functionalization of Oligodeoxynucleotides for Non-Radioactive Labelling", *Tetrahedron Letters*, Elsevier, Amsterdam, vol. 31 No. 11, 1990, 1543-1546.
Ambrose, W. et al., "Single Molecule Detection With Total Internal Reflection Excitation: Comparing Signal-to-Background and Total Signals in Different Geometries", *Cytometry*, vol. 36 No. 3, 1999, 224-231.
Amit, et al., "Photosensitive Protecting Groups of Amino Sugars and Their Use on Glycoside Synthesis. 2-Nitrobenzyloxycarbonylamino

(56) References Cited

OTHER PUBLICATIONS and 6-Nitroveratryloxycarbonylamino Derivatives.", *J. Org. Chem.*, 39 (2), American Chemical Society, 1974, 192-196.

Ananthi, S., "Recorders in Medical Instruments", *A Text book of Medical Instruments, New Age International, New Delhi*, Chapter 19, 2006, 538-548.

Arndt-Joven, D. et al., "Immunofluorescence Localization of Z-DNA in Chromosomes: Quantitation by Scanning Microphotometry and Computer-assisted Image Analysis", *The Journal of Cell Biology*, vol. 101, Oct. 1985, 1422-1433.

Augustin, M. A. et al., "Progress towards single-molecule sequencing: enzymatic synthesis of nucleotide-specifically labeled DNA", *Journal of Biotechnology*, vol. 8, No. 13, 2001, 289-301.

Axelrod, D., "Cell-Substrate Contacts Illuminated by Total Internal Reflection Fluorescence", *The Journal of Cell Biology*, vol. 89, Apr. 1981, 141-145.

Axelrod, D. et al., "Total internal reflection fluorescent microscopy", *Journal of Microscopy*, vol. 129, 1983, 19-28.

Bai, X. et al., "Photocleavage of a 2-nitrobenzyl linker bridging a fluorophore to the 5' end of DNA", *Proc Natl Acad Sci*, USA, vol. 100, No. 2, 2003, 409-13.

Bailey, J. M. et al., "Affinity Labeling of NADP+-Specific Isocitrate Dehydrogenase by a New Fluorescent Nucleotide Analogue, 2-[(4-bromo-2,3-dioxobutyl)thio]-1,N6-ethenoadenosine 2',5'-bisphosphate+", *Biochemistry*, vol. 24 (20), 1985, 5367-5377.

Basche, T. et al., "Single Molecule Optical Detection, Imaging and Spectroscopy", *Weinheim:VCM, Germany*, 1997, Ch.2 and 3.

Beaucage, S. et al., "Advances in the Synthesis of Oligonucleotides by the Phosphoramidite Approach", *Tetrahedron Report No. 309*, vol. 48, No. 12, 1992, 2223-2311.

Beese, Lorena S. et al., "Structure of DNA Polymerase I Klenow Fragment Bound to Duplex DNA", *Science*, vol. 260, American Association for the Advancement of Science, Apr. 16, 1993, 352-355.

Bennett, et al., "Solexa Sequencing chemistry can be applied to different platforms which will have common elements in detection and data processing", *Pharmacogenomics*, vol. 5, No. 4, 2004, 433-438.

Biesalski, et al., "Preparation and Characterization of a Polyelectrolyte Monolayer Covalently Attached to a Planar Solid Surface", The Article was published on the web, *Macromolecules*, vol. 32, No. 7, 1999, 2309-2316.

Black, D. L. , "Protein diversity from alternating splicing: A challenge for bioinformatics and post genome biology", *Cell*, vol. 103, No. 3, 2000, 367-370.

Blattner, F. R. et al., "The Complete genome sequence of *Escherichia coli* K-12", *Science*, vol. 277, 1997, 1453-1474.

Boles, et al., "High-Resolution Mapping of Carcinogen Binding Sites on DNA", *Biochemistry*, vol. 25, 1986, 3039-3043.

Brakmann, et al., "Optimal Enzymes for Single-Molecule Sequencing", *Current Pharmaceutical Biotechnology*, vol. 5, 2004, 119-126.

Brakmann, S. et al., "The large fragment of *Escherichia coli* DNA polymerase I can synthesize DNA exclusively from fluorescently labeled nucleotides", *Chembiochem*, vol. 2, No. 10, 2001, 773-777.

Braslavsky, et al., "Sequence Information Can Be Obtained From Single DNA Molecules,", *PNAS*, vol. 100, No. 7,, Apr. 1, 2003, pp. 3960-3964.

Braslavsky, I. et al., "Objective-type dark-field illumination for scattering from microbeads", *Applied Optics*, vol. 40, No. 31, Nov. 2001, 5650-5657.

Braslavsky, I. et al., "Single Molecule Measurements of DNA Polymerase Activity: A Step Towards Single Molecule Sequencing", *Biophys.*, 2002, 507A.

Brechtel, R. et al., "Control of the electro osmotic flow by metal-salt-containing buffers", *J Chromatoraphy A.*, vol. 716, 1995, 97-105.

Bridgman, A. et al., "An improved method for the synthesis of mercurated dUTP. Enzymatic synthesis of Hg-labelled DNA of high molecular weight suitable for use in an image based DNA sequencing strategy", *DNA Seq.*, vol. 6, No. 4, 1996, 199-209.

Bruggert, J. et al., "Microfabricated tools for nanoscience", *J. Micromech.Microeng.*,, vol. 3, 1993, 161-167.

Bryzek, J. et al., "Micromachines on the march", *IEEE Spectrum*, vol. 31, No. 5, 1994, 20-31.

Buchaillot, L. et al., "Silicon Nitride Thin Films Young's Modulus Determination by an Optical Non Destructive Method", *Jpn. J. Appl. Phys.*,, vol. 36, Jun. 1997, L794-L797.

Burghardt, et al., "Total Internal Reflection/Fluorescence Photobleaching Recovery Study of Serum Albumin Adsorption Dynamics", *Biophys. Journal*, vol. 33, Mar. 1981, 455-468.

Burghardt, T. et al., "Total Internal Reflection Fluorescence Study of Energy Transfer in Surface-Adsorbed and Dissolved Bovine Serum Albumin", *Biochemistry*, vol. 22, 1983, 979-985.

Butler, D. et al., "Draft data leave geneticists with a mountain still to climb", *Nature*, vol. 405, Issue 6782, May 2000, 984-985.

Canard, B et al., "Catalytic editing properties of DNA polymerases", *Proc. Natl. Acad. Sci. USA*, vol. 92, No. 24, Nov. 1995, 10859-10863.

Canard, B. et al., "DNA polymerase fluorescent substrates with reversible 3'-tags", *Gene*, vol. 148, No. 1, 1994, 1-6.

Cheng, et al., "High-speed DNA sequence analysis", *Prog. in Biochem. and Biophys.*,, vol. 22, 1995, 223-227.

Chicurel, M. , "Faster, better, cheaper genotyping", *Nature*, vol. 412, Issue 6847, Aug. 2001, 580-582.

Chidgeavadze, Z. G. et al., "2',3'-Dideoxy-3' aminonucleoside 5'triphosphates are the terminators of DNA synthesis catalyzed by DNA polymerases", *Nucl. Acids Res.* 12 (3):, 1984, 1671-1686.

Chidgeavadze, Z. G. et al., "3'-Floro-2',3'-dideoxyribonucleoside 5'-triphosphates: terminators of DNA synthesis", *FEBS Letters 183*:, 1985, 275-278.

Chiu, D. et al., "Patterned deposition of cells and proteins onto surfaces by using three-dimensional microfluidic systems", *PNAS*, vol. 97, No. 6, 2000, 2408-2413.

Chou, et al., "A Microfabricated Device for Sizing and Sorting DNA Molecules,", *PNAS*, vol. 96, Jan. 1999, 11-13.

Chou, et al., "A Microfabricated Rotary Pump", *Biomedical Microdevices*, vol. 3, 2001, 323-330.

Close, D. et al., "Ultraviolet Photobleaching of Free Radicals Created in y-Irradiated Amino Acids", *Radiation Research*, vol. 53, 1973, 349-357.

Cooper, J. et al., "Analysis of Fluorescence Energy Transfer in Duplex and Branched DNA Molecules", *Biochemistry*, vol. 29, No. 39, 1990, 9261-9268.

Crocker, J. C. et al., "Methods of digital video microscopy for colloidal studies", *Journal of Colloid and Interface Science*, vol. 179, No. 1, 1996, 298-310.

Dapprich, Johannes, "Single-Molecule DNA Digestion by Lambda-Exonuclease", *Cytometry*, vol. 36, No. 3, 1999, 163-168.

Debenham, J. S. et al., "Two New Orthogonal Amine-Protecting Groups that can be Cleaved under Mild or Neutral Conditions", *Journal of the American Chemical Society*, vol. 117, No. 11, 1995, 3302-3303.

Decher, G. et al., "Buildup of ultrathin multilayer films by a self-assembly process: III. Consecutively alternating adsorption of anionic and cationic polyelectrolytes on charged surfaces", *Thin Solid Films*, vol. 210-211, Part 2, 1992, pp. 831-835.

Decher, G. et al., "Fuzzy nanoassemblies : Toward layered polymeric multicomposites", *Science*, vol. 277, No. 5330, 1997, 1232-1237.

Delamarche, E. et al., "Patterned Delivery of Immunoglobulins to Surfaces Using Microfluidic Networks", *Science*, vol. 276, 1997, 779-781.

Dempster, J. , "Computer Analysis of Electrophysiological Signals", *Academic Press*, Chapter 2, 1993, 31 pages.

Dickson, et al., "Simultaneous Imaging of Individual Molecules aligned both parallel and perpendicular to the optic axis", *The American Physical Society*, vol. 81, No. 24, 1998, 5322-5325.

Doktycz, M. et al., "Genosensors and Model Hybridization Studies", *Automation Technologies for Genome Characterization*, Ch.10, T. Beugelsdijk (Ed), John Wiley & Sons, Inc.,, 1997, 205-225.

Doublie, S. et al., "Crystal Structure of a bacteriophage T7 DNA replication complex at 2.2A[SYMBOL] resolution", *Nature*, vol. 391, Jan. 15, 1988, pp. 251-258.

(56) References Cited

OTHER PUBLICATIONS

Driscoll, Robert J. et al., "Atomic-scale imaging of DNA using scanning tunnelling microscopy", *Nature*, vol. 346, No. 6281, Jul. 19, 1990, 294-296.

Drmanac, R. et al., "Sequencing by hybridization: Towards an automated sequencing of one million M13 clones arrayed on membranes", *Electrophoresis*, vol. 13, 1992, 566-573.

Duffy, et al., "Patterning Electroluminescence Materials with Feature Sizes as Small as 5 um Using Elastomeric Membranes as Masks for Dry Lift-Off", *Advanced Materials*, vol. 11, No. 7, 1999, 546-552.

Duffy, et al., "Rapid prototyping of microfluidic switches in poly(dimethyl siloxane) and their acuation by electro-osmotic flow", *J. Micromech. Microeng.*, vol. 9, 1999, 211-217.

Duffy, et al., "Rapid Prototyping of Microfluidic Systems in Poly(dimethylsiloxane)", *Analytical Chemistry*, vol. 70, No. 23, 1998, 4974-4984.

Easmon, C. S. et al., "The Measurement of Opsonic and Phagocytic Function by Luminol-Dependent Chemiluminescence", *Immunology*, vol. 41, No. 1, 1980, 67-74.

Effenhauser, et al., "Integrated capillary electrophoresis on Flexible silicone microdevices: Analysis of DNA restriction fragments and detection of single DNA molecules on microchips", *Anal. Chem.*, vol. 69, 1997, 3451-3457.

Effenhauser, et al., "Integrated chip-based capillary electrophoresis" *Electrophoresis*, vol. 18, 1997, 2203-2213.

Eigen, M., "Sorting single molecules: application to diagnostics and evolutionary biotechnology", *Proc. Natl. Acad. Sci.*, vol. 91, 1994, pp. 5740-5747.

Evangelista, R. A. et al., "Characterization of fluorescent nucleoside triphosphates by capillary electrophoresis with laser-induced fluorescence detection:Action of alkaline phosphatase and DNA polymerase", *Analytical Biochemistry*, vol. 235, No. 1, 1996, 89-97.

Fahrenberg, et al., "A microvalve system fabricated by thermoplastic molding", *J. Micromech. Microeng.*, vol. 5, 1995, 169-171.

Ferguson, "A fiber-optic DNA biosensor microarray for the analysis of gene expression", *Nature Biotechnology*, vol. 14, 1996, 1681-1684.

Forster, T., "Delocalized Excitation and Excitation Transfer", *Modem Quantum Chem., Istanbul Lectures, Part III, Academic Press*, New York, 1965, 93-137.

Fritz, J. et al., "Electronic detection of DNA by its intrinsic molecular charge", *PNAS*, vol. 99, No. 22, Oct. 2002, 14142-14146.

Fu, et al., "An integrated microfabricated cell sorter", *Analytical Chemistry*, vol. 74, No. 11, Jun. 1, 2002, 2451-2457.

Fu, Anne Y. et al., "A microfabricated fluorescence-activated cell sorter", *Nature America, Inc.*, vol. 17, 1999, pp. 1109-1111.

Funatsu, et al., "Imaging of Single Fluorescent Molecules and Individual ATP Turnovers by Single Myosin Molecules in Aqueous Solution", *Letters to Nature*, vol. 374, Apr. 1995, 555-559.

Garcia, A. M. « Determination of Ion Penneability by Fluorescence Quenching », *Methods in Enzymology*, vol. 207, No. 33, 1992, 501-511.

Gardner, et al., "Comparative kinetics of nucleotide analog incorporation by Vent DNA polymerase", *J. Biol. Chem.*, vol. 279, No. 12, 2004, 11834-11842.

Gardner, Andrew F. et al., "Acyclic and dideoxy terminator preferences denote divergent sugar recognition by archaeon and Taq DNA polymerases", *Nucleic Acids Research*, vol. 30, No. 2, 2002, 605-613.

Giller, et al., "Incorporation of reporter molecule-labeled nucleotides by DNA polymerases. I. Chemical synthesis of various reporter group-labeled 2'deoxyribonucleoside-5'-triphosphates", *Nucleic Acids Res.*, vol. 31, No. 10, 2003, 2630-2635.

Giusti, W. et al., "Synthesis and Characterization of 5'-Fluorescent-dye-labeled Oligonucleotides", *PCR Methods and Applications*, vol. 2, 1993, 223-227.

Goll, et al., "Microvalves with bistable buckled polymer diaphragms", *J. Micromech. Microeng.*, vol. 6, 1996, 77-79.

Goodwin, P. et al., "Application of single molecule detection to DNA sequencing", *Nucleosides, Nucleotides & Nucleic Acids*, vol. 16, No. 5&6, May 1997, pp. 543-550.

Gravesen, et al., "Microfluidics—a review", *J. Micromech. Microeng.*, vol. 3, 1993, 168-182.

Greene, T. W. et al., "Protective Groups in Organic Synthesis", *John Wiley & Sons, Inc.*, New York, 3rd Ed., 1999.

Gueroui, Z. et al., "Observation by fluorescence microscopy of transcription on single combed DNA", *PNAS*, vol. 99, No. 9, 2002, 6005-6010.

Guilbault, G., "Practical Fluorescence—Theory, Methods and Techniques", *Chapters 1 and 3, Marcel Dekker, Inc.*, New York, 1973, 521-524.

Guillier, F. et al., ""Linkers and Cleavage Strategies in Socio-Phase Organic Synthesis and Combinational Chemistry"", vol. 100, May 6, 2000, 2091-2157.

Gupta, K. C. et al., "A general method for the synthesis of 3'-sulfhydryl and phosphate group containing oligonucleotides", *Nucleic Acids Research*, vol. 19, No. 11, Jun. 11, 1991, 3019-3025.

Gyllenstein, U. B. et al., "Generation of single-stranded DNA by the polymerase chain reaction and its application to direct sequencing of the HLA-DQA locus", *Proc. Natl. Acad. Sci*, vol. 85, 1988, 7652-7656.

Ha, "Single molecule spectroscopy with automated positioning", *Appl. Phys. Lett.*, vol. 70, No. 6, 1997, 782-784.

Ha, "Single-Molecule Fluorescence Methods for the Study of Nucleic Acids", *Current Opinion in Structural Biology*, vol. 11, 2001, 287-292.

Ha, T. et al., "Single molecule dynamics studied by polarization modulation", *Phys. Rev. Lett.*, vol. 77, No. 19, 1996, 3979-3982.

Ha, T. et al., "Single-Molecule Fluorescence Resonance Energy Transfer", *Methods*, vol. 25, No. 1, 2001, 78-86.

Ha, T. et al., "Single-Molecule Fluorescence Spectroscopy of Enzyme Conformational Dynamics and Cleavage Mechanism", *PNAS*, vol. 96, No. 3, 1999, pp. 893-898.

Hamamatsu Photonics, K.K., "High Sensitivity Cameras: Principle and Technology", *Technical Note*, 2006, 8 pages.

Hanna, M et al., "Synthesis and characterization of a new photocrosslinking CTP analog and its use in photoaffimity labeling E. coli and T7 RNA polymerases", *Nucleic Acids Research*, vol. 21, No. 9, 1993, 2073-2079.

Hansen, C. J. et al., "A robust and scalable microfluidic metering method that allows Protein crystal growth by free interface diffusion", *Proc Natl Acad Sci U S A*, vol. 99, No. 26, 2002, 16531-16536.

Harding, J., "Single-molecule detection as an approach to rapid DNA sequencing", *Trends in Biotechnology*, vol. 10, 1992, 55-57.

Harris, J. M., "Introduction to Biochemical and biomedical applications of poly (ethylene glycol)", *Poly(ethylene glycol) Chemistry*, Plenum Press: New York, 1992, 1-14.

Harrison, D. et al., "Micromachining a Miniaturized Capillary Electrophoresis-Based Chemical Analysis Systems on a Chip", *Science*, vol. 261, 1993, 895-897.

Harrison, D. et al., "Towards miniaturized electrophoresis and chemical analysis systems on silicon: an alternative to chemical sensors", *Sensors and Actuators B*, vol. 10, 1993, 107-116.

Hasan, A. et al., "Photolabile Protecting Groups for Nucleosides: Synthesis and Photodeprotection Rates", *Tetrahedron*, vol. 53, No. 12, 1997, 4247-4264.

Hornbeck, L. et al., "Bistable Deformable Mirror Device", *Techlical Digest Series, Optical Society of America*, vol. 8, Jun. 1988, 107-110.

Horowitz, P. et al., "The Art of Electronics", 2nd Edition, Cambridge University Press, Cambridge, Chapter 9, 1989, 14 pages.

Horowitz, P. et al., "The Art of Electronics", 2nd Edition, Cambridge University Press, Cambridge, Chapter 15, 1989, 987-1041.

Hosokawa, et al., "Handling of Picoliter liquid samples in a poly(dimethylsiloxane)-based microfluidic device", *Anal. Chem.*, vol. 71, No. 20, 1999, 4781-4785.

Houseal, T. et al., "Real-Time Imaging of Single DNA Molecules with Fluorescence Microscopy", *Biophys. J.*, vol. 56, 1989, pp. 507-516.

(56) References Cited

OTHER PUBLICATIONS

Howorka, Stefan et al., "Sequence-specific detection of individual DNA strands using engineered nanopores", Nature Biotechnology, vol. 19, 2001, 636-639.
Hubner, et al., "Direct observation of the triplet lifetime quenching of single dye molecules by molecular oxygen", J. Chem. Physics, vol. 115, No. 21, 2001, 9619-9622.
Hultman, T. et al., "Bidirectional Solid-Phase Sequencing of In Vitro-Amplified Plasmid DNA", BioTechniques, vol. 10, No. 1, 1991, 84-93.
Hyman, David E., "A New Method of Sequencing DNA", Analytical Biochemistry, vol. 174, Apr. 1988, 423-436.
Ikuta, et al., "Three dimensional micro integrated fluid systems (MIFS) fabricated by stereo lithography", IEEE Kyushu Institute of Technology, 1994, 1-6.
Ishii, et al., "Fluorescence resonance energy transfer between single fluorophores attached to a coiled-coil protein in aqueous solution", Chemical Physics, vol. 247, 1999, 163-173.
Ishijima, A. et al., "Simultaneous Observation of Individual ATPase and Mechanical Events by a Single Myosin Molecule during Interaction with Actin", Cell, vol. 92, Jan. 1998, 161-171.
Ishikawa, M. et al., "Single-Molecule Detection by Laser-Induced Fluorescence Technique with a Position-Sensitive Photon-Counting Apparatus", Appl. Phys.,, vol. 33, Part 1, No. 3A, 1994, 1571-1576.
Jacobs, et al., "Combinatorial Chemistry-Applications of Light-Directed Chemical Synthesis", Tibtech, vol. 12, No. 1, Jan. 1994, 19-26.
Jacobson, et al., "Microfluidic devices for electrokinetically driven parallel and serial mixing", Anal. Chem.,, vol. 71, No. 20, 1999, 4455-4459.
Jacobson, K. et al., "International Workshop on the application of fluorescence photobleaching techniques to problems in cell biology", Workshop Summary, Federation Proceedings, vol. 42, 1983, 72-79.
Jacobson, S. C. et al., "High-speed separations on a microchip", Anal. Chem, vol. 66, No. 7, 1994, 1114-1118.
Jett, J. et al., "High-Speed DNA Sequencing: An Approach Based Upon Fluorescence Detection of Single Molecules", Journal of Biomolecular Structure and Dynamics, vol. 7, No. 2, 1989, 301-308.
Johnston, R. et al., "Autoradiography using storage phosphor technology", Electrophoresis, vol. 11, 1990, 355-360.
Jongeneel, C. V. et al., "Comprehensive sampling of gene expression in human cell lines with massively parallel signature sequencing", Proc Natl Acad Sci , USA, vol. 100, No. 8, 2003, 636-639.
Joos, Beda et al., "Covalent Attachment of Hybridizable Oligonucleotides to Glass Supports", Analytical Biochem., vol. 247(1), 1997, pp. 96-101.
JP2000-547272, "Office Action dated Jan. 27, 2004", Japanese Patent Application, Jan. 27, 2004, 12 pages.
JP2004-218570, "Office Action dated May 8, 2007", Japanese Patent Application, May 8, 2007, 7 pages.
Kambara, H. et al., "Optimization of Parameters in a DNA Sequenator using Fluorescence Detection", Biotechnology, vol. 6, 1988, 816-821.
Kartalov, et al., "Poly-Electrolyte Surface-Chemistry Platform for Fluorescence Studies of DNA on Glass", http://www.ugcs.caltech.edu/.about.kartalov/PEM.sub.--6.pdf, Jun. 7, 2002, 1-7.
Kartalov, et al., "Single-Molecule Detection and DNA Sequencing-by-Synthesis", In Partial Fulfillment of the Requirements for the Degree of Doctor Philosophy, California Institute of technology, 2004, 1-160.
Kartalov, E. P. et al., "Microfluidic device reads up to four consecutive base pairs in DNA sequencing-by-synthesis", Nucleic Acids Research, vol. 32, No. 9, 2004, 2873-2879.
Kawai, et al., "A simple method of detecting amplified DNA with immobilized probes on microtiter wells", Analytical Biochemistry, vol. 209, 1993, 63-69.
Kelso, et al., "Single-cell analysis by RT-PCR reveals differential expression of multiple type 1 and 2 cytokine genes among cells within polarized CD4+ T cell populations", International Immunology, vol. 11, No. 4, 1999, 617-621.
Kenis, et al., "Microfabrication inside capillaries using multiphase laminar flow patterning", Science, vol. 285, 1999, 83-85.
Kenney, Mary et al., "Mutation Typing Using Electrophoresis and Gel-Immobilized Acrydite(TM) Probes", Biotechniques, 25, 1998, 516-521.
Khandjian, E., "UV cross linking of RNA to nylon membrane enhances hybridization signals", Mole. Bio. Rep., vol. 11, 1986, 107-115.
Khrapko, et al., "A Method for DNA Sequencing by Hybridization with Oligonucleotide Matrix", J. DNA Seq. Map., vol. 1, 1991, 375-388.
Kiefer, J. R. et al., "Crystal structure of a thermostable Bacillus DNA polymerase 1 large fragment at 2.1 A resolution", Structure, vol. 5, Current Biology Ltd., Jan. 15, 1997, 95-108.
Kim, Y. et al., "Crystal Structure of Thermus Acquatics DNA Polymerase", Nature, vol. 376, Aug. 17, 1995, 612-616.
Kirkland, T. A. et al., "Ring-Closing Metathesis in Methanol and Water", Journal of Organic Chemistry, vol. 63, No. 26, 1998, 9904-9909.
Knerr, L. et al., "Application of a ring-closing-metathesis-based linker to the solid phase synthesis of oligosaccharides", Synlett, vol. 11, 1999, 1802-1804.
Knowles, A. et al., "Practical Absorption Spectrometry", Chapman and Hall, London, Chapter 6, 1984, 32 pages.
Kopp, M. U. et al., "Chemical Amplification: Continuous-Flow PCR on a Chip", Science, vol. 280, May 18, 1998, 1046-1048.
Korolev, S. et al., "Crystal structure of the large fragment of Thermus aquaticus DNA polymerase I at 2.5 A resolution: Structural basis for thermostability", PNAS, USA, vol. 92, 1995, 9264-9268.
Kovacs, et al., "Simple synthesis of 5-vinyl-and 5-ethynyl-2' deoxyuridine 5'-triphosphates", Tetrahedron Letters, vol. 29, No. 36, 1988, 4525-4528.
Kricka, et al., "Labels, Labeling, Analytical Strategies, and Applications", Ch. 1 and Table Ix, Academic Press, New York, 1995, 3-40.
Krider, E. et al., "2'-Modified Nucleosides for Site-Specific Labeling of Oligonucleotides", Bioconjugate Chem.,, vol. 13, No. 1, 2002, 155-162.
Kuhn, L. et al., "Silicon Charge Electrode Array for Ink Jet Printing", IEEE Trans. on Electron Dev.,, vol. ED-25, No. 10, Oct. 1978, 1257-1260.
Lacoste, T. et al., "Ultrahigh-resolution multicolor colocalization of single fluorescent probes", PNAS, vol. 97, No. 17, 2000, 9461-9466.
Lander, E et al., "Initial sequencing and analysis of the human genome", Nature, vol. 409, 2001, pp. 860-921.
Lazowski, K. et al., "Highly Sensitive Detection of Hybridization of Oligonucleotides to Specific Sequences of Nucleic Acids by Application of Fluorescence Resonance Energy Transfer", Antisense and Nucleic Acid Drug Dev.,, vol. 10, 2000, 97-103.
Leach, R. W. et al., "Description, Performance and Calibration of a Charge-Coupled-Device Camera", Publications of the Astronomical Society of the Pacific, vol. 92, No. 546, 1980, 233-245.
Lee, "Enhancing the catalytic repertoire of nucleic acids: a systematic study of linker length and rigidity", Nucleic Acids Res.,, vol. 29, No. 7, Apr. 2001, 1565-1573.
Lee, Y. et al., "Laser-Induced Fluorescence Detection of a Single Molecule in a Capillary", Anal. Chem.,, vol. 66, 1994, 4142-4149.
Leonard, N. J. et al., "Synthesis of Fluorescent Nucleotide Analogues: 5'-mono-, di-, and triphosphates of Linear-Benzoguanosine, Linear-Benzoinosine and Linear-Benzoxanthosine", Proceedings of the National Academy of Sciences, vol. 76, No. 9, 1979, 4262-4264.
Levene, M J. et al., "Zero-Mode Waveguides for Single Molecule Analysis at High Concentrations", Science, vol. 229, 2003, pp. 682-686.
Levsky, et al., "Single-cell gene expression profiling", Science, vol. 297, 2002, 836-840.
Li, et al., "Ultrasensitive Coincidence Fluorescence Detection of Single DNA Molecules,", Anal. Chem., vol. 75, No. 7,, Apr. 1, 2003, 1664-1670.
Li, Y. et al., "Structural Studies of the Klentaq1 DNA Polymerase", Current Organic Chem.,, vol. 5, 2001, 871-883.

(56) References Cited

OTHER PUBLICATIONS

Li, Yanlong et al., "Design, Synthesis, and Spectroscopic Properties of Peptide-Bridged Fluorescence Energy-Transfer Cassettes", *Bioconjugate Chemistry*, vol. 10, No. 2, 1999, 241-245.
Li, Z et al., "A photocleavable fluorescent nucleotide for DNA sequencing and analysis", *PNAS*, vol. 100 (2), 2003, pp. 414-419.
Lin, L. et al., "Free-Space Micromachined Optical Switches for Optical Networking", *IEEE J. of Selected Topics in Quantum Electronics*, vol. 5, No. 1, 1999, 4-9.
Liu, J. et al., "A nanoliter rotary device for polymerase chain reaction", *Electrophoresis*, vol. 23, No. 10, 2002, 1531-1536.
Lodder, M. et al., "Misacylated Transfer RNAs Having a Chemically Removable Protecting Group", *Journal of Organic Chemistry*, vol. 63, No. 3, 1998, 794-803.
Loh, E. et al., "Polymerase chain reaction with single-sided specificity: analysis of T cell receptor delta chain.", *Science*, 243, 1989, pp. 217-220.
Lok, C., "Deciphering DNA, Top Speed—Helicos BioSciences aims to expedite sequencing, enable genomic medicine", *Technology Review*, May 2005, 27-28.
Lopez, G. et al., "Fabrication and Imaging of Two-Dimensional Patterns of Proteins Adsorbed on Self-Assembled Monolayers by Scanning Electron Microscopy", *J. Arner. Chem. Soc.,*, vol. 115, 1993, 10774-10781.
Lotters, et al., "The mechanical properties of the rubber elastic polymer polydimethylsiloxane for sensor applications", *J. Micromech. Microeng.*, vol. 7, 1997, 145-147.
Lucy, et al., "Characterization of the cationic surfactant induced reversal of electroosmotic flow in capillary electrophoresis", *Anal. Chem.,*, vol. 68, 1996, 300-305.
Ludwig, J et al., "Rapid and Efficient Synthesis of Nucleoside 5'-O-(1-Thiotriphosphates), 5'-Triphosphates and 2',3'-Cyclophosphorothioates Using 2-Chloro-4H-1,3,2-benzodioxaphosphorin-4-one", *J Org Chem*, vol. 54, 1989, pp. 631-635.
Lvov, Y. et al., "Assembly of Thin Films by Means of Successive Deposition of Alternate Layers of DNA and Poly(allylamine)", *American Chemical Society, Macromolecules*, vol. 26, 1993, 5396-5399.
Macklin, J. et al., "Imaging and Time-Resolved Spectroscopy of Single Molecules at an Interface", *Science*, vol. 272, No. 5259, Apr. 1996, 255-258.
Malier, B et al., "Replication by a single DNA polymerase of a stretched single-stranded DNA", *PNAS*, vol. 97(22), 2000, pp. 12002-12007.
Manz, A. et al., "Miniaturized Total Chemical Analysis Systems: A Novel Concept for Chemical Sensing", *Sensors and Actuators*, vol. B1, 1990, 244-248.
Marriott, G. et al., "Time resolved imaging microscopy—Phosphorescence and delayed fluorescence imaging", *Biophys. J.,*, vol. 60, Dec. 1991, 1374-1387.
Marziali, A. et al., "New DNA sequencing methods", *Annual Review of Biomedical Engineering*, vol. 3, 2001, 195-223.
Mastrangelo, C. et al., "Vacuum-Sealed Silicon Micromachined Incandescent Light Source", *IDEM*, vol. 89, 1989, 503-506.
Meiners, J. C. et al., "Femonewton force spectroscopy of single extended DNA molecules", *Phys Rev Lett*, vol. 84, No. 21, 2000, 5014-5017.
Meldrum, K., "Microfluidics-based products for nucleic acid analysis", http://www.americanlaboratory.com/articles/al/a9909mel.pdf, Sep. 1999, 2 pages.
Meller, Amit et al., "Rapid nanopore discrimination between single polynucleotide molecules", *PNAS*, vol. 97, No. 3, Feb. 1, 2000, pp. 1079-1084.
Mertz, J. et al., "Single-molecule detection by two-photon-excited fluorescence", *Optics Letters*, vol. 20, No. 24, Dec. 1995, 2532-2534.
Metzker, et al., "Elimination of residual natural nucleotides from 3'-O-modified-dNTP syntheses by enzymatic mop-up", *BioTechniques*, vol. 25, 1998, 814-817.

Metzker, M. et al., "Electrophoretically Uniform Fluorescent Dyes for Automated DNA Sequencing", *Science*, vol. 271, 1996, 1420-1422.
Metzker, Michael et al., "Termination of DNA synthesis by a novel 3'-modifies-deoxyribonucleoside 5'-triphosphates", *Nucleic Acids Res.*, vol. 22(20), 1994, 4259-4267.
Mitra, R et al., "Fluorescent In Situ Sequencing on Polymerase Colonies", *Anal Biochem*, vol. 320, 2003, pp. 55-65.
Moe, et al., "Rapid Detection of Clinically Relevant Bacteria in Platelets Using the Hybriscan Baceterial Detection system", *Journal of the American Society of Hematology*, vol. 96, No. 11, 2000, 4155.
Moore, P., "To affinity and beyond", *Nature*, vol. 426, No. 6967, 2003, 725-731.
Muller, et al., "Surface-micromachined microoptical elements and systems", *IEEE*, vol. 86, No. 8, 1998, 1705-1720.
Nelson, Paul S. et al., "Bifunctional oligonucleotide probes synthesized using a novel CPG support are able to detect single base pair mutations", *Nucleic Acids Research*, vol. 17, Sep. 25, 1989, 7187-7193.
Nie, Shuming et al., "Probing individual molecules with confocal fluorescence microscopy", *Science*, vol. 266, Nov. 11, 1994, 1018-1021.
Nyren, Pal et al., "Solid Phase DNA Minisequencing by an Enzymatic Luminometric Inorganic Pyrophosphate Detection Assay", *Analytical Biochemistry*, vol. 208, No. 1, 1993, 171-175.
Ochman, H. et al., "Genetic Applications of an Inverse Polymerase Chain Reaction", *Genetics*, vol. 120, 1988, 621-623.
Ohara, T. et al., ""Wired" Enzyme Electrodes for Amperometric Determination of Glucose or Lactate in the Presence of Interfering Substancess", *Anal. Chem.,*, vol. 66, No. 15, Aug. 1994, 2451-2457.
Ohara, T. et al., "Glucose Electrodes Based on Cross-Linked [Os(bpY)2CltH Complexed Poly(1-vinylimidazole) Films", *Anal. Chem.,*, vol. 65, 1993, 3512-3517.
Okabe, S. et al., "Do Photobleached Fluorescent Microtubules Move?: Re-evaluation of Fluorescence Laser Photobleaching both In Vitro and in Growing Xenopus Axon", *J. Cell Bio.,*, vol. 120, No. 5, 1993, 1177-1186.
Ollis, D. L. et al., "Structure of large fragment of *Escherichia coli* DNA polymerase I complexed with dTMP", *Nature*, vol. 313, Feb. 28, 1985, pp. 762-766.
Oroskar, A. et al., "Detection of immobilized amplicons by ELISA-like techniques", *Clin. Chem.,*, vol. 42, No. 9, 1996, 1547-1555.
Padmaja, T. et al., "Enzymatically degradable prodrugs: a novel methodology for drug linkage", *Journal of Applied Polymer Science*, vol. 85, No. 10, 2002, 2108-2118.
Patchornik, A. et al., "Photosensitive Protecting Groups", *J. Amer. Chem. Soc.*, 92, 1970, 6333-6335.
PCT/US1999/009616, International Preliminary Examination Report dated Nov. 28, 2000, Nov. 28, 2000, 5 pages.
PCT/US1999/009616, "International Search Report dated Oct. 14, 1999", Oct. 14, 1999, 3 pages.
PCT/US1999/009616, "Written Opinion dated Jul. 21, 2000", Jul. 21, 2000, 4 pages.
PCT/US2002/27605, "International Search Report dated Mar. 27, 2003", Mar. 27, 2003, 2 pages.
Pennisi, E., "Gene researchers hunt bargins, fixer-upper", *Science*, vol. 298, No. 5594, 2002, 735-736.
Perales, et al., "Enhancement of DNA, cDNA synthesis and fidelity at high temperatures by a dimeric single-stranded DNA-binding protein", *Nucleic Acids Res.,*, vol. 31, No. 22, 2003, 6473-6480.
Perkins, T. et al., "Relaxation of a Single DNA Molecule Observed by Optical Microscopy", *Science*, vol. 264, May 1994, 822-826.
Pethig, R. et al., "Applications of dielectrophoresis in biotechnology", *TIBTECH*, vol. 15, 1997, 426-432.
Pisani, F. et al., "Domain Organization and DNA-Induced Conformational Changes of an Archaeal Family B DNA Polymerase", *Biochemistry*, vol. 35, Jul. 1996, 9158-9166.
Plakhotnik, T. et al., "Single-Molecule Spectroscopy", *Annu. Rev. Phys. Chem.,*, vol. 48, 1997, 181-212.
Ploem, J. et al., "Fluorescence Microscopy", *Fluorescent and Luminescent Probes for Biological Activity*, Academic Press, London, Ch. 1, 1993, 1-11.

(56) References Cited

OTHER PUBLICATIONS

Qin, et al., "Elastomeric Light Valves", *Advanced Materials*, vol. 9, No. 5, 1997, 407-410.

Qin, P. et al., "Site-Specific Labeling of RNA with Fluorophores and Other Structural Probes", *Methods*, vol. 18, No. 1, May 1999, 60-70.

Quake, S. et al., "Fluorescent Photobleaching Method for Sequencing DNA", *Circa*, 1996, 1-10.

Quake, S. et al., "From Micro- to Nanofabrication with Soft Materials", *Science*, vol. 290, No. 5496, Nov. 2000, 1536-1540.

Quake, S. et al., "Polymer Physics with Single Molecules of DNA", (Dept. of Physics), a colloquium by Stephen Quake, Stanford University, Presented at Laser Spectroscopy XII Intl. Conference, Italy, Jun. 1995, Feb. 22, 1996.

Rapp, R. et al., "LIGA micropump for gases and liquids", *Sensors and Actuators A*, vol. 40, 1994, 57-61.

Rasolonjatovo, I. et al., "6-N-(N-methylanthranyamido)-4-oxo-hexanoic acid: a new florescent protecting group applicable to a new DNA sequencing method", *Nucleosides & Nucleotides*, vol. 17, No. 9-11, 1998, 2021-2025.

Rasolonjatovo, I. et al., "Development of a new DNA sequencing method: 3'-ester cleavage catalyzed by Taq DNA polymerase", *Nucleosides & Nucleotides*, vol. 18, No. 4 & 5, 1999, 1021-1022.

Reha-Krantz, et al., "Motif A of Bacteriophage T4 DNA Polymerase: Role in Primer Extension and DNA Replication Fidelity", *J. Bio. Chem.*, vol. 269, No. 8, 1994, 5635-5643.

Reha-Krantz, L. et al., "Genetic and Biochemical Studies of Bacteriophage T4 DNA Polymerase 3'.fwdarw.5'-Exonuclease Activity", *The Journal of Biological Chemistry*, vol. 268, No. 36, 1993, 27100-27108.

Rigler, R. et al., "DNA-sequencing at the single molecule level", *Journal of Biotechnology*, vol. 86, No. 3, 2001, p. 161.

Rigler, R. et al., "Fluorescence correlations, single molecule detection and large number screening Applications in Biotechnology", *Journal of Biotechnology*, vol. 41, 1995, 177-186.

Rosenblum, B B. et al., "Improved single-strand DNA sizing accuracy in capillary electrophoresis", *Nucl. Acids Res.*, vol. 25, No. 19, 1997, 3925-3929.

Rosenblum, B B. et al., "New dye-labeled terminators for improved DNA sequencing patterns", *Nucleic Acids Research*, vol. 25, No. 22, Nov. 1997, 4500-4504.

Roylance, L. et al., "A Batch-Fabricated Silicon Accelerometer", *IEEE Trans. on Elec. Dev.*, vol. ED-26, No. 12, 1979, 1911-1917.

Ruparel, H. et al., "Design and synthesis of a 3'-a-allyl photocleavable fluorescent nucleotide as a reversible terminator for DNA sequencing by synthesis", vol. 102 (17), Apr. 1, 2005, 5932-5937.

Ruth, J. et al., "Nucleoside Analogues with Clinical Potential in Antivirus Chemotherapy", *Molecular Pharmacology*, vol. 20, 1981, 415-422.

Sarfati, S. R. et al., "Synthesis of fluorescent derivatives of 3'-O-(6-aminohexanoyl)-pyrimidine nucleosides 5'-triphosphates that act as DNA polymerase substrates reversibly tagged at C-3", *Journal of the Chemical Society, Perkin Transactions :Organic and Bio-Organic Chemistry*, vol. 9, 1995, 1163-1171.

Sato, Eisuke, "Bimane Conjugates of 5-Halogenouridylic Acids as Fluorogenic Substrates for Phosphodiesterase I", *J. Chem. Research*, 1994, 390-391.

Satoh, et al., "Flow-Injection Determination of Inorganic Pyrophosphate with Use of an Enzyme Thermistor Containing Immobilized Inorganic Pyrophosphatase", *Anal Chim Acta*, vol. 214, No. 1-2, 1988, 409-413.

Satoh, I et al., "Flow-injection determination of inorganic pyrophosphate with use of an enzyme thermistor containing immobilized inorganic pyrophosphate", *Chemical Abstracts*, vol. 110, No. 16, Abstract No. 146806; XP002116838, Apr. 17, 1989, 1.

Sauer, M et al., "Single molecule DNA sequencing in submicrometer channels: state of the art and future prospects", *J Biotech*, vol. 86, 2001, pp. 181-201.

Schasfoort, R. et al., "Field-effect flow control for microfabricated fluidic networks", *Science*, vol. 286(5441), 1999, pp. 942-945.

Schueller, O. et al., "Reconfigurable diffraction gratings based on elastomeric microfluidic devices", *Sensors and Actuators*, vol. 78, 1998, 149-159.

Seeger, S. et al., "Single molecule fluorescence—High Performance Molecular Diagnosis and Screening", *Translated from BIOforum*, Apr. 1998, 179-185.

Selvin, "Fluorescence Resonance Energy Transfer", *Methods in Enzymology*, vol. 246, 1995, 300-335.

Seo, "Photocleavable fluorescent nucleotides for DNA sequencing on a chip constructed by site-specific coupling chemistry", *PNAS*, vol. 101, No. 15, Apr. 13, 2004, 5488-5493.

Seo, Tae Seok et al., "Four-color DNA sequencing by synthesis on a chip using photocleavable fluorescent nucleotides", *PNAS*, vol. 102, No. 17, 2005, 5926-5931.

Shackelford, J. F. et al., "Intro. to Materials Science for Engineers", 3.sup.rd Edition, Prentice-Hall, Inc., Macmillan Publ. Co., 1992.

Shendure, et al., ""Advance Sequencing Technologies: Methods and Goals"", *Nat Rev Genet*. May 2004; 5(5):, May 2004, 335-344.

Shoji, S. et al., "Fluids for Sensor Systems", *Microsystem Technology in Chemistry and Life Science, Topics in Current Chem.*, vol. 194, 1998, 162-188.

Shoji, S. et al., "Smallest Dead Volume Microvalves for Integrated Chemical Analyzing Systems", *Proceedings of Transducers '91, IEEE*, San Francisco, 1991, 1052-1055.

Smith, L. et al., "The synthesis of oligonucleotides containing an aliphatic amino group at the 5' terminus: synthesis of fluorescent DNA primers for use in DNA sequence analysis", *Nucleic Acids Res.*, vol. 13, No. 7, 1985, 2399-2412.

Smith, Lloyd et al., "Fluorescence detection in automated DNA sequence analysis", *Nature*, vol. 321, 1986, 674-679.

Smith, S. et al., "Direct Mechanical Measurements of the Elasticity of Single DNA Molecules by Using Magnetic Beads", *Science*, vol. 258, 1992, 1122-1126.

Smits, I., "Piezoelectric Micropump with Three Valves Working Peristaltically", *Sensors and Actuators*, vol. A21-A23, 1990, 203-206.

Song, et al., "Influence of the triplet excited state on the photobleaching kinetics of fluorescein in microscopy", *Biophysics J.*, vol. 70, 1996, 2959-2968.

Sproat, Brian S. et al., "The synthesis of protected 5'-mercapto-2',5'-dideoxyribonucleoside-3'-0-phosphorainidites; uses of 5'-mercapto-oligodeoxyribonucleotides", *Nucleic Acids Research*, vol. 15, No. 12, Jun. 25, 1987, 4837-4849.

Stocki, S. et al., "Dynamics of Bacteriophage T4 DNA Polymerase Function: Identification of Amino Acid Residues that Affect Switching between Polymerase and 3'.fwdarw.5'-Exonuclease Activities", *J. Mol. Biol*, vol. 254, 1995, 15-28.

Strausberg, Robert et al., "The mammalian gene collection", *Science*, vol. 286, No. 5439, Oct. 15, 1999, 455-457.

Sukhorukov, G. B. et al., "Assembly of polyelectrolyte multilayer films by consecutively alternating adsorption of polynucleotides and polycations", *Thin Solid Films*, vol. 284-285, 1996, 220-223.

Tasara, et al., "Incorporation of reporter molecule-labeled nucleotides by DNA polymerases. II. High-density labeling of natural DNA", *Nucleic Acids Res.*, vol. 31, No. 10, 2003, 2636-2646.

Taveira, N. et al., "Detection of HI VI proviral DNA by PCR and hybridization with digoxigenin labeled probes", *Mol. Cell Probes*, vol. 6, No. 4, 1992, 265-270.

Taylor, D. et al., "Characterization of chemisorbed monolayers by surface potential measurements", *J. Phys. D. Appl. Phys.*, vol. 24, 1991, 1443-1450.

Terry, E. M. , "Advanced Laboratory Practice in Electricity and Magnetism", *McGraw-Hill Book Co., Inc.*, Section 61, 1922, 11 pages.

Terry, S. et al., "A Gas Chromatographic Air Analyzer Fabricated on a Silicon Wafer", *IEEE Trans. on Electron Dev.*, vol. ED-26, No. 12, 1979, 1880-1886.

Theisen, P. et al., "Fluorescent dye phosphoramidite labeling of oligonucleotides", *Nucleic Acids Symp. Ser.*, vol. 27, 1992, 99-100.

Thompson, N. et al., "Immunoglobulin Surface-Binding Kinetics Studied by Total Internal Reflection with Fluorescence Correlation Spectroscopy", *Biophys. J.*, vol. 43, Jul. 1983, 103-114.

(56) References Cited

OTHER PUBLICATIONS

Thompson, N. et al., "Measuring Surface Dynamics of Biomolecules by Total Internal Reflection Fluorescence with Photobleaching Recovery or Correlation Spectroscopy", *Biophys. J.*,, vol. 33, Mar. 1981, 435-454.
Thorsen, et al., "Microfluidic large-scale integration", *Science*, vol. 298, No. 5593, 2002, 580-584.
Tokunaga, Makio et al., "Single Molecule Imaging of Fluorophores and Enzymatic Reactions Achieved by Objective-Type Total Internal Reflection Fluorescence Microscopy", *Biochemical and Biophysical Research Communications*, vol. 235, No. 1, Jun. 9, 1997, 47-53.
Toneguzzo, F. et al., "Use of a Chemically Modified T7 DNA Polymerase for Manual and Automated Sequencing of Super coiled DNA", *BioTech*, vol. 6, No. 5, 1988, 460-469.
Trager, R. S. et al., "DNA sequencing—Venter's next goal: 1000 human genomes", *Science*, vol. 298, No. 5595, 2002, 947.
Tufte, O. et al., "Silicon Diffused-Element Piezoresistive Diaphragms", *J. Applied Phys.*,, vol. 31, No. 11, Nov. 1962, 3322-3327.
Tyagi, Sanjay et al., "Multicolor molecular beacons for allele discrimination", *Nature Biotechnology*, vol. 16, 1998, 49-53.
Unger, M et al., "Monolithic Microfabricated Valves and Pumps by Multilayer Soft Lithography", *Science*, 288:, 2000, 113-116.
Unger, M et al., "Single-Molecule Fluorescence Observed with Mercury Lamp Illumination", *Biotechniques*, vol. 27, Nov. 1999, 1008-1014.
U.S. Appl. No. 09/941,882, "Office Action dated Jul. 23, 2003", U.S. Patent Application, Jul. 23, 2003, 7 pages.
U.S. Appl. No. 10/229,997, "Office Action dated Dec. 27, 2004", U.S. Patent Application, Dec. 27, 2004, 9 pages.
U.S. Appl. No. 10/709,436, "Amendment and Response to Office Action dated Oct. 22, 2008", U.S. Patent Application, Oct. 22, 2008, 7 pages.
U.S. Appl. No. 10/709,436, "Amendment and Response to Office Action dated Aug. 24, 2009", U.S. Patent Application, Aug. 24, 2009, 8 pages.
U.S. Appl. No. 10/709,436, "Office Action dated Feb. 24, 2009", U.S. Patent Application, Feb. 24, 2009, 8 pages.
U.S. Appl. No. 10/709,436, "Office Action dated May 22, 2008", U.S. Patent Application, May 22, 2008, 10 pages.
U.S. Appl. No. 10/709,436, "Office Action dated Jun. 12, 2007", U.S. Patent Application, Jun. 12, 2007, 52 pages.
U.S. Appl. No. 10/709,436, "Response to Office Action dated Dec. 12, 2007", U.S. Patent Application, Dec. 12, 2007, 4 pages.
U.S. Appl. No. 11/929,141, "Amendment and Response to Office Action dated Mar. 23, 2010", U.S. Patent Application, Mar. 23, 2010, 15 pages.
U.S. Appl. No. 11/929,141, "Office Action dated Jan. 14, 2010", U.S. Patent Application, Jan. 14, 2010, 6 pages.
U.S. Appl. No. 11/929,141, "Office Action dated Apr. 14, 2010", U.S. Patent Application, Apr. 14, 2010, 7 pages.
U.S. Appl. No. 11/929,141, "Office Action dated Aug. 12, 2009", U.S. Patent Application, Aug. 12, 2009, 8 pages.
U.S. Appl. No. 11/929,141, "Response to Office Action dated Nov. 12, 2009", U.S. Patent Application, Nov. 12, 2009, 15 pages.
U.S. Appl. No. 12/617,842, "Office Action dated Jun. 15, 2010", U.S. Patent Application, Jun. 15, 2010, 10 pages.
U.S. Appl. No. 12/969,872, "Notice of Allowance dated Jan. 3, 2012", U.S. Patent Application, Jan. 3, 2012, 5 pages.
U.S. Appl. No. 12/969,872, "Office Action dated Jun. 29, 2011", U.S. Patent Application, Jun. 29, 2011, 8 pages.
U.S. Appl. No. 13/008,303, "Office Action dated Jan. 25, 2012", U.S. Patent Application, Jan. 25, 2012, 10 pages.
U.S. Appl. No. 13/008,303, "Office Action dated Sep. 16, 2011", U.S. Patent Application, Sep. 16, 2011, 8 pages.
U.S. Appl. No. 13/008,392, "Office Action dated Nov. 16, 2011", U.S. Patent Application, Nov. 16, 2011, 7 pages.
U.S. Appl. No. 13/008,392, "Office Action dated Mar. 7, 2012", U.S. Patent Application, Mar. 7, 2012, 8 pages.
U.S. Appl. No. 13/008,392, "Office Action dated Jun. 8, 2011", U.S. Patent Application, Jun. 8, 2011, 9 pages.
U.S. Appl. No. 13/099,718, "Office Action dated Feb. 2, 2012", U.S. Patent Application, Feb. 2, 2012, 5 pages.
U.S. Appl. No. 13/099,718, "Office Action dated Feb. 5, 2013", U.S. Patent Application, Feb. 5, 2013, 7 pages.
U.S. Appl. No. 13/099,718, "Office Action dated Aug. 8, 2013", U.S. Patent Application, Aug. 8, 2013, 8 pages.
U.S. Appl. No. 13/156,117, "Office Action dated Jan. 12, 2012", U.S. Patent Application, Jan. 12, 2012, 6 pages.
U.S. Appl. No. 13/156,117, "Office Action dated Apr. 24, 2012", U.S. Patent Application, Apr. 24, 2012, 6 pages.
U.S. Appl. No. 13/408,458, "Office Action dated Aug. 9, 2013", U.S. Patent Application, Aug. 9, 2013, 17 pages.
U.S. Appl. No. 95/001,529, "Action Closing Prosecution mailed Oct. 20, 2011", U.S. Patent Reexamination, Oct. 20, 2011, 18 pages.
U.S. Appl. No. 95/001,529, "Kits and Reagents for Automated DNA Analysis, Exhibit F mailed on Jun. 9, 2011", Jun. 9, 2011, 3 pages.
U.S. Appl. No. 95/001,529, "Non-Final Office Action dated Mar. 10, 2011", U.S. Patent Reexamination, Mar. 10, 2011, 13 pages.
U.S. Appl. No. 95/001,529, "Notice of Intent to Issue a Reexam Certificate dated Dec. 26, 2012", U.S. Patent Reexamination, Dec. 26, 2012, 4 pages.
U.S. Appl. No. 95/001,529, "Notice of Right of Appeal mailed Apr. 26, 2012", U.S. Patent Reexamination, Apr. 26, 2012, 18 pages.
U.S. Appl. No. 95/001,529, "Nucleic Acid Labeling and Detection, Non-radioactive Labeling and Detection of Nucleic Acids, Exhibit E", Jun. 9, 2011, 96-97.
U.S. Appl. No. 95/001,529, "Reexamination Certificate dated Jan. 11, 2013", U.S. Patent Reexamination, Jan. 11, 2013, 2 pages.
U.S. Appl. No. 95/001,529, "Request to Grant Order for Inter Partes Reexamination mailed Mar. 10, 2011", U.S. Patent Reexamination, Mar. 10, 2011, 8 pages.
U.S. Appl. No. 95/001,529, "Response to Action Closing Prosecution dated Nov. 21, 2011", U.S. Patent Reexamination, Nov. 21, 2011, 21 pages.
U.S. Appl. No. 95/001,529, "Response to Non-Final Action dated May 10, 2011", U.S. Patent Reexamination, May 10, 2011, 33 pages.
U.S. Appl. No. 95/001,532, "Action Closing Prosecution mailed Oct. 5, 2011", U.S. Patent Reexamination, Oct. 5, 2011, 30 pages.
U.S. Appl. No. 95/001,532, "Non-Final Office Action dated Apr. 13, 2011", U.S. Patent Reexamination, Apr. 13, 2011, 21 pages.
U.S. Appl. No. 95/001,532, "Notice of Intent to Issue a Reexam Certificate dated Sep. 6, 2012", U.S. Patent Reexamination, Sep. 6, 2012, 5 pages.
U.S. Appl. No. 95/001,532, "Notice of Right of Appeal mailed May 9, 2012", U.S. Patent Reexamination, May 9, 2012, 28 pages.
U.S. Appl. No. 95/001,532, "Reexamination Certificate dated Oct. 5, 2012", U.S. Patent Reexamination, Oct. 5, 2012, 2 pages.
U.S. Appl. No. 95/001,532, "Request to Grant Order for Inter Partes Reexamination mailed Apr. 13, 2011", U.S. Patent Reexamination, Apr. 13, 2011, 16 pages.
U.S. Appl. No. 95/001,532, "Response to Action Closing Prosecution dated Dec. 5, 2011", U.S. Patent Reexamination, Dec. 5, 2011, 19 pages.
U.S. Appl. No. 95/001,532, "Response to Non-Final Action dated Jun. 13, 2011", U.S. Patent Reexamination, Jun. 13, 2011, 30 pages.
U.S. Appl. No. 95/001,643, "Action Closing Prosecution mailed Jun. 1, 2012", U.S. Patent Reexamination, Jun. 1, 2012, 15 pages.
U.S. Appl. No. 95/001,643, "Appeal Brief by Patent Owner mailed May 13, 2013", U.S. Patent Reexamination, May 13, 2013, 27 pages.
U.S. Appl. No. 95/001,643, "Appeal Brief by Third Party Requestor mailed May 13, 2013", U.S. Patent Reexamination, May 13, 2013, 125 pages.
U.S. Appl. No. 95/001,643, "Non-Final Office Action dated Aug. 17, 2011", U.S. Patent Reexamination, Aug. 17, 2011, 16 pages.
U.S. Appl. No. 95/001,643, "Notice of Right of Appeal mailed Jan. 23, 2013", U.S. Patent Reexamination, Jan. 23, 2013, 16 pages.
U.S. Appl. No. 95/001,643, "Respondent Brief by Patent Owner mailed Jun. 13, 2013", U.S. Patent Reexamination, Jun. 13, 2013, 314 pages.

(56) References Cited

OTHER PUBLICATIONS

U.S. Appl. No. 95/001,643, "Respondent Brief by Patent Owner mailed Jul. 17, 2013", U.S. Patent Reexamination, Jul. 17, 2013, 309 pages.
U.S. Appl. No. 95/001,643, "Respondent Brief by Third Party Requestor mailed Jun. 13, 2013", U.S. Patent Reexamination, Jun. 13, 2013, 236 pages.
U.S. Appl. No. 95/001,643, "Response to Action Closing Prosecution dated Jul. 2, 2012", U.S. Patent Reexamination, Jul. 2, 2012, 16 pages.
U.S. Appl. No. 95/001,643, "Response to Non-Final Action dated Oct. 17, 2011", U.S. Patent Reexamination, Oct. 17, 2011, 10 pages.
Vale, R. et al., "Direct observation of single kinesin molecules moving along microtubules", Nature, vol. 380, Apr. 1996, 451-453.
Van Dam, R. M. et al., "Gene expression analysis with universal n-mer arrays", Genome Res, vol. 12, No. 1, 2002, 145-152.
Van De Pol, F. et al., "Micro-liquid handling devices: A Review", Micro System Technologies 90, 1.sup.st Intl. Conf., On Micro Electro, Opto, Mechanic Systems and Components, Berlin, Springer-Verlag, 1990, 799-805.
Van Oijen, et al., "Single molecule kinetics of lambda exonuclease reveal base dependence and dynamic disorder", Science, vol. 301, 2003, 1235-1238.
Venter, J C. et al., "The sequence of the human genome", Science, vol. 291, No. 5507, Feb. 16, 2001, 1304-1351.
Vieider, C. et al., "A Pneumatically Actuated Micro Valve With a Silicone Rubber Membrane for Integration With Fluid-Handling Systems", Proceedings of Transducers '95, Stockholm, 1995, 284-286.
Walker, M. G. et al., "Prediction of gene function by genome-scale expression analysis: Prostate cancer-associated genes", Genome Researce, vol. 9, No. 12, 1999, 1198-1203.
Wang, et al., "Design and Synthesis of New Fluorogenic HIV Protease Substrates Based on Resonance Energy Transfer", Tetrahedron Letters, vol. 31, No. 45, 1990, 6493-6496.
Wang, M. D. et al., "Force and Velocity measured for single molecules of RNA polymerase", Science, vol. 282, No. 5390, 1998, 902-907.
Washizu, Masao et al., "Molecular Dielectrophoresis of Biopolymers", IEEE Transactions on Industry Applications, vol. 30, No. 4, Jul./Aug. 1994, 835-843.
Watkins, R. et al., "A Total Internal-Reflection Technique for the Examination of Protein Adsorption", J. Biomed. Mater. Res.,, vol. 11, 1977, 915-938.
Weber, J. L. et al., "Human whole-genome shotgun sequencing", Genome Research, vol. 7, No. 5, 1997, 401-409.
Webster, J. et al., "Monolithic Capillary Gel Electrophoresis Stage with On-Chip Detector", Intl. Con.English Pound. on MEMS (MEMS 96), 1996, 491-496.
Wedekind, P. et al., "Scanning microphotolysis: a new photobleaching technique based on fast intensity modulation of a scanned laser beam and confocal imaging", J. Microscopy, vol. 176, Pt. 1, Oct. 1994, 23-33.
Weir, et al., "Hybrigel Purification: A Novel Technique for Accelerated Prepration of DNA Sequence Products for Capillary Electrophoresis and Multiplexing", Clinical Chemistry, vol. 45, No. 11, 1999, 2052.
Weiss, S, "Fluorescence spectroscopy of single biomolecules", Science, vol. 283, Mar. 1999, 1676-1683.
Welch, M. B. et al., "Synthesis of fluorescent, photolabile 3'-O-protected nucleoside triphosphates for the base addition sequencing scheme", Nucleosides & Nucleotides, vol. 18, No. 2, 1999, 197-201.

Werner, et al., "Progress towards single-molecule DNA sequencing: a one color demonstration", J Biotechnology, vol. 102, No. 1, 2003, 1-14.
Williams, N. et al., "Exploring the Adenine Nucleotide Binding Sites on Mitochondrial F.sub.1-ATPase with a New Photoaffinity Probe, 3'-O-(4-Benzoyl)benzoyl Adenosine 5'-Triphosphate", J. Biol. Chem.,, vol. 237, No. 6, 1982, 2834-2841.
Winter, et al., "Direct gene expression analysis", Curr. Pharm. Biotech.,, vol. 5, 2004, 191-197.
Wu, Felicia Y. et al., "Synthesis and properties of adenosine-5'-triphosphoro-γ-1-(5-sulfonic acid)naphthyl ethylamidate: A fluorescent nucleotide substrate for DNA-dependent RNA polymerase from Escherichia coli", Archives of Biochemistry and Biophysics, vol. 246, No. 2, May 1, 1986, 564-571.
Wuite, G. et al., "Single-molecule studies of the effect of template tension on T7 DNA polymerase activity", Nature, vol. 404, 2000, 103-106.
Xia, et al., "Complex Optical Surfaces Formed by Replica Molding Against Elastomeric Masters", Science, vol. 273, 1996, 347-349.
Xia, et al., "Soft lithography", Angew. Chem. Int. Ed. 37, 1998, 550-575.
Xia, G et al., "Directed evolution of novel polymerase activities: Mutation of a DNA polymerase into an efficient RNA polymerase", PNAS, vol. 99(10), 2002, pp. 6597-6602.
Xie, "Single molecule approach to dispersed kinetics and dynamic disorder: Probing conformational fluctuation and enzymatic dynamics", J. Chem. Physics, vol. 117, No. 24, 2002, 11024-11032.
Xu, et al., "Direct Measurement of Single-Molecule Diffusion and Photodecomposition in Free Solution,", Science, vol. 275, No. 21, Feb. 1997, 1106-1109.
Xu, Xiao-Hong N. et al., "Long-Range Electrostatic Trapping of Single-Protein Molecules at a Liquid-Solid Interface", Science, vol. 11, No. 5383, Sep. 1998, 1650-1653.
Yang, et al., "A Mems Thermopneumatic Silicone Rubber Membrane Valve", Proceedings of IEEE 10.sup.th Annual International Workshop on MicroElectro Mech.,Sys., Sensors and Actuators, vol. A64, No. 1, 1998, 101-108.
Yazdi, N. et al., "Micromachined Inertial Sensors", Proceedings of the IEEE, vol. 86, Aug. 1998, 1640-1659.
Yershov, et al., "DNA Analysis and Diagnostics on Oligonucleotide Microchips", Proc. Natl, Acad. Sci. USA 93, 1996, 4913-4918.
Young, et al., "Contoured elastic-membrane microvalves for microfluidic network integration", J. Biomechanical Engineering, vol. 121, 1999, 2-6.
Yu, et al., "Cyanine dye dUTP analogs for enzymatic labeling of DNA probes", Nucleic Acids Res.,, vol. 22, No. 15, 1994, 3226-3232.
Zdeblick, M. et al., "A Microminiature Electric-to-Fluidic Valve", Transducers '87, Reprinted in Micromechanics and MEMS Classic and Seminal Papers to 1990, IEEE Press, 1987, 437-439.
Zhu, Z et al., "Directly labeled DNA probes using fluorescent nucleotides with different length linkers.", Nucleic Acids Research, vol. 22, No. 16, Aug. 25, 1994, 3418-3422.
Zhu, Z. et al., "Molecular Mechanism Controlling the Incorporation of Fluorescent Nucleotides into DNA by PCR", Cytometry, vol. 28, 1997, 206-211.
Zuckermann, R. et al., "Efficient Methods for attachment of thiol Specific Probes to the 3'-Ends of Synthetic Oligodeoxybonucleotides", Nucleic Acids Research, Oxford University Press vol. 15(13), Jul. 10, 1987, 5305-5321.
"Chapter 26. Nucleotide Metabolism, Exhibit B", 1995, 796.

* cited by examiner

FLUORESCENCE SPECTRA OF EQUIMOLAR FLUORESCEIN AND TETRA METHYLRHODAMINE BEFORE AND AFTER ADDITION OF DIPHENYLIODONIUM CHLORIDE

EFFECT OF A LEADING STRAND POPULATION ON EXTENSION SIGNALS

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
ctgagaaacc agaaagtcct                                           20

<210> SEQ ID NO 2
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 2
agaaggaaag ggattgttct ggatattacc ag                             32

<210> SEQ ID NO 3
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 3
gggaaaggaa ga                                                   12

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
ctggtaatat ccagaacaat                                           20

<210> SEQ ID NO 5
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 5
gtgcagatct g                                                    11

<210> SEQ ID NO 6
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 6
ctgagaaacc agaaagtcct cagt                                      24

METHOD OF DETERMINING THE NUCLEOTIDE SEQUENCE OF OLIGONUCLEOTIDES AND DNA MOLECULES

CROSS REFERENCE TO RELATED APPLICATIONS

This patent application is a continuation of Ser. No. 12/969,872 filed Dec. 16, 2010, which is a continuation of Ser. No. 11/929,141 filed Oct. 30, 2007, now U.S. Pat. No. 7,875,440, which is a continuation of Ser. No. 10/709,436 filed May 5, 2004, now U.S. Pat. No. 7,645,596, which is a continuation of Ser. No. 09/941,882 filed Aug. 28, 2001, now U.S. Pat. No. 6,780,591, which is a continuation-in-part of Ser. No. 09/673,544 filed Feb. 26, 2001, which is a national stage entry of PCT/US99/09616 filed Apr. 30, 1999, which claims the benefit of provisional application Ser. No. 60/083,840 filed May 1, 1998.

SEQUENCE LISTING

This application contains a Sequence Listing, which has been submitted in ASCII format via EFS-Web and is hereby incorporated by reference in its entirety. Said ASCII copy is named LT00853_1_CON_12_ST25.txt, was created on Jul. 21, 2014, and is 1,886 bytes in size.

INTRODUCTION

The present invention relates to a novel method for analyzing nucleic acid sequences based on real-time detection of DNA polymerase-catalyzed incorporation of each of the four deoxynucleoside monophosphates, supplied individually and serially as deoxynucleoside triphosphates in a micro fluidic system, to a template system comprising a DNA fragment of unknown sequence and an oligonucleotide primer. Incorporation of a deoxynucleoside monophosphate (dNMP) into the primer can be detected by any of a variety of methods including but not limited to fluorescence and chemiluminescence detection. Alternatively, microcalorimetric detection of the heat generated by the incorporation of a dNMP into the extending primer using thermopile, thermistor and refractive index measurements can be used to detect extension reactions. The present invention further provides a method for monitoring and correction of sequencing errors due to misincorporation or extension failure.

The present invention provides a method for sequencing DNA that avoids electrophoretic separation of DNA fragments thus eliminating the problems associated with anomalous migration of DNA due to repeated base sequences or other self-complementary sequences which can cause single-stranded DNA to self-hybridize into hairpin loops, and also avoids current limitations on the size of fragments that can be read. The method of the invention can be utilized to determine the nucleotide sequence of genomic or cDNA fragments, or alternatively, as a diagnostic tool for sequencing patient derived DNA samples.

BACKGROUND OF INVENTION

Currently, two approaches are utilized for DNA sequence determination: the dideoxy chain termination method of Sanger (1977, Proc. Natl. Acad. Sci. 74:5463-5674) and the chemical degradation method of Maxam (1977, Proc. Natl. Acad. Sci. 74:560-564). The Sanger dideoxy chain termination method is the most widely used method and is the method upon which automated DNA sequencing machines rely. In the chain termination method, DNA polymerase enzyme is added to four separate reaction systems to make multiple copies of a template DNA strand in which the growth process has been arrested at each occurrence of an A, in one set of reactions, and a G, C, or T, respectively, in the other sets of reactions, by incorporating in each reaction system one nucleotide type lacking the 3'-OH on the deoxyribose at which chain extension occurs. This procedure produces a series of DNA fragments of different lengths, and it is the length of the extended DNA fragment that signals the position along the template strand at which each of four bases occur. To determine the nucleotide sequence, the DNA fragments are separated by high resolution gel electrophoresis and the order of the four bases is read from the gel.

A major research goal is to derive the DNA sequence of the entire human genome. To meet this goal the need has developed for new genomic sequencing technology that can dispense with the difficulties of gel electrophoresis, lower the costs of performing sequencing reactions, including reagent costs, increase the speed and accuracy of sequencing, and increase the length of sequence that can be read in a single step. Potential improvements in sequencing speed may be provided by a commercialized capillary gel electrophoresis technique such as that described in Marshall and Pennisi (1998, Science 280:994-995). However, a major problem common to all gel electrophoresis approaches is the occurrence of DNA sequence compressions, usually arising from secondary structures in the DNA fragment, which result in anomalous migration of certain DNA fragments through the gel.

As genomic information accumulates and the relationships between gene mutations and specific diseases are identified, there will be a growing need for diagnostic methods for identification of mutations. In contrast to the large scale methods needed for sequencing large segments of the human genome, what is needed for diagnostic methods are repetitive, low-cost, highly accurate techniques for resequencing of certain small isolated regions of the genome. In such instances, methods of sequencing based on gel electrophoresis readout become far too slow and expensive.

When considering novel DNA sequencing techniques, the possibility of reading the sequence directly, much as the cell does, rather than indirectly as in the Sanger dideoxynucleotide approach, is a preferred goal. This was the goal of early unsuccessful attempts to determine the shapes of the individual nucleotide bases with scanning probe microscopes.

Additionally, another approach for reading a nucleotide sequence directly is to treat the DNA with an exonuclease coupled with a detection scheme for identifying each nucleotide sequentially released as described in Goodwin, et al., (1995, Experimental Techniques of Physics 41:279-294). However, researchers using this technology are confronted with the enormous problem of detecting and identifying single nucleotide molecules as they are digested from a single DNA strand. Simultaneous exonuclease digestion of multiple DNA strands to yield larger signals is not feasible because the enzymes rapidly get out of phase, so that nucleotides from different positions on the different strands are released together, and the sequences become unreadable. It would be highly beneficial if some means of external regulation of the exonuclease could be found so that multiple enzyme molecules could be compelled to operate in phase. However, external regulation of an enzyme that remains docked to its polymeric substrate is exceptionally difficult, if not impossible, because after each digestion the next substrate segment is immediately present at the active site. Thus, any controlling signal must be present at the active site at the start of each reaction.

A variety of methods may be used to detect the polymerase-catalyzed incorporation of deoxynucleoside monophosphates (dNMPs) into a primer at each template site. For example, the pyrophosphate released whenever DNA polymerase adds one of the four dNTPs onto a primer 3' end may be detected using a chemiluminescent based detection of the pyrophosphate as described in Hyman E. D. (1988, Analytical Biochemistry 174:423-436) and U.S. Pat. No. 4,971,903. This approach has been utilized most recently in a sequencing approach referred to as "sequencing by incorporation" as described in Ronaghi (1996, Analytical Biochem. 242:84) and Ronaghi (1998, Science 281:363-365). However, there exist two key problems associated with this approach, destruction of unincorporated nucleotides and detection of pyrophosphate. The solution to the first problem is to destroy the added, unincorporated nucleotides using a dNTP-digesting enzyme such as apyrase. The solution to the second is the detection of the pyrophosphate using ATP sulfurylase to reconvert the pyrophosphate to ATP which can be detected by a luciferase chemiluminescent reaction as described in U.S. Pat. No. 4,971,903 and Ronaghi (1998, Science 281: 363-365). Deoxyadenosine a-thiotriphosphate is used instead of dATP to minimize direct interaction of injected dATP with the luciferase.

Unfortunately, the requirement for multiple enzyme reactions to be completed in each cycle imposes restrictions on the speed of this approach while the read length is limited by the impossibility of completely destroying unincorporated, non-complementary, nucleotides. If some residual amount of one nucleotide remains in the reaction system at the time when a fresh aliquot of a different nucleotide is added for the next extension reaction, there exists a possibility that some fraction of the primer strands will be extended by two or more nucleotides, the added nucleotide type and the residual impurity type, if these match the template sequence, and so this fraction of the primer strands will then be out of phase with the remainder. This out of phase component produces an erroneous incorporation signal which grows larger with each cycle and ultimately makes the sequence unreadable.

A different direct sequencing approach uses dNTPs tagged at the 3' OH position with four different colored fluorescent tags, one for each of the four nucleotides is described in Metzger, M. L., et al. (1994, Nucleic Acids Research 22:4259-4267). In this approach, the primer/template duplex is contacted with all four dNTPs simultaneously. Incorporation of a 3' tagged NMP blocks further chain extension. The excess and unreacted dNTPs are flushed away and the incorporated nucleotide is identified by the color of the incorporated fluorescent tag. The fluorescent tag must then be removed in order for a subsequent incorporation reaction to occur. Similar to the pyrophosphate detection method, incomplete removal of a blocking fluorescent tag leaves some primer strands unextended on the next reaction cycle, and if these are subsequently unblocked in a later cycle, once again an out-of-phase signal is produced which grows larger with each cycle and ultimately limits the read length. To date, this method has so far been demonstrated to work for only a single base extension. Thus, this method is slow and is likely to be restricted to very short read lengths due to the fact that 99% efficiency in removal of the tag is required to read beyond 50 base pairs. Incomplete removal of the label results in out of phase extended DNA strands.

SUMMARY OF INVENTION

Accordingly, it is an object of the present invention to provide a novel method for determining the nucleotide sequence of a DNA fragment which eliminates the need for electrophoretic separation of DNA fragments. The inventive method, referred to herein as "reactive sequencing", is based on detection of DNA polymerase catalyzed incorporation of each of the four nucleotide types, when deoxynucleoside triphosphates (dNTP's) are supplied individually and serially to a DNA primer/template system. The DNA primer/template system comprises a single stranded DNA fragment of unknown sequence, an oligonucleotide primer that forms a matched duplex with a short region of the single stranded DNA, and a DNA polymerase enzyme. The enzyme may either be already present in the template system, or may be supplied together with the dNTP solution.

Typically a single deoxynucleoside triphosphate (dNTP) is added to the DNA primer template system and allowed to react. As used herein deoxyribonucleotide means and includes, in addition to dGTP, dCTP, dATP, dTTP, chemically modified versions of these deoxyribonucleotides or analogs thereof. Such chemically modified deoxyribonucleotides include but are not limited to those deoxyribonucleotides tagged with a fluorescent or chemiluminescent moiety. Analogs of deoxyribonucleotides that may be used include but are not limited to 7-deazapurine. The present invention additionally provides a method for improving the purity of deoxynucleotides used in the polymerase reaction.

An extension reaction will occur only when the incoming dNTP base is complementary to the next unpaired base of the DNA template beyond the 3' end of the primer. While the reaction is occurring, or after a delay of sufficient duration to allow a reaction to occur, the system is tested to determine whether an additional nucleotide derived from the added dNTP has been incorporated into the DNA primer/template system. A correlation between the dNTP added to the reaction cell and detection of an incorporation signal identifies the nucleotide incorporated into the primer/template. The amplitude of the incorporation signal identifies the number of nucleotides incorporated, and thereby quantifies single base repeat lengths where these occur. By repeating this process with each of the four nucleotides individually, the sequence of the template can be directly read in the 5' to 3' direction one nucleotide at a time.

Detection of the polymerase mediated extension reaction and quantification of the extent of reaction can occur by a variety of different techniques, including but not limited to, microcalorimetic detection of the heat generated by the incorporation of a nucleotide into the extending duplex. Optical detection of an extension reaction by fluorescence or chemiluminescence may also be used to detect incorporation of nucleotides tagged with fluorescent or chemiluminescent entities into the extending duplex. Where the incorporated nucleotide is tagged with a fluorophore, excess unincorporated nucleotide is removed, and the template system is illuminated to stimulate fluorescence from the incorporated nucleotide. The fluorescent tag may then be cleaved and removed from the DNA template system before a subsequent incorporation cycle begins. A similar process is followed for chemiluminescent tags, with the chemiluminescent reaction being stimulated by introducing an appropriate reagent into the system, again after excess unreacted tagged dNTP has been removed; however, chemiluminescent tags are typically destroyed in the process of readout and so a separate cleavage and removal step following detection may not be required. For either type of tag, fluorescent or chemiluminescent, the tag may also be cleaved after incorporation and transported to a separate detection chamber for fluorescent or chemiluminescent detection. In this way, fluorescent quenching by adjacent fluorophore tags incorporated in a single base repeat sequence may be avoided. In addition, this may protect the DNA template system from possible radiation damage in the case of fluorescent detection or from possible chemical damage in the case of chemiluminescent detection. Alternatively the fluorescent tag may be selectively destroyed by a chemical or photochemical reaction. This process eliminates the need to cleave the tag after each readout, or to detach and transport the tag from the reaction chamber to a separate detection chamber for fluorescent detection. The present invention provides a method for selective destruction of a fluorescent tag by a photochemical reaction with diphenyliodonium ions or related species.

The present invention further provides a reactive sequencing method that utilizes a two cycle system. An exonuclease-deficient polymerase is used in the first cycle and a mixture of exonuclease-deficient and exonuclease-proficient enzymes are used in the second cycle. In the first cycle, the template-primer system together with an exonuclease deficient polymerase will be presented sequentially with each of the four possible nucleotides. In the second cycle, after identification of the correct nucleotide, a mixture of exonuclease proficient and deficient polymerases, or a polymerase containing both types of activity will be added in a second cycle together with the correct dNTP identified in the first cycle to complete and proofread the primer extension. In this way, an exonuclease-proficient polymerase is only present in the reaction cell when the correct dNTP is present, so that exonucleolytic degradation of correctly extended strands does not occur, while degradation and correct re-extension of previously incorrectly extended strands does occur, thus achieving extremely accurate strand extension.

The present invention also provides a method for monitoring reactive sequencing reactions to detect and correct sequencing reaction errors resulting from misincorporation, i.e., incorrectly incorporating a non-complementary base, and extension failure, i.e., failure to extend a fraction of the DNA primer strands. The method is based on the ability to (i) determine the size of the trailing strand population (trailing strands are those primer strands which have undergone an extension failure at any extension prior to the current reaction step); (ii) determine the downstream sequence of the trailing strand population between the 3' terminus of the trailing strands and the 3' terminus of the corresponding leading strands ("downstream" refers to the template sequence beyond the current 3' terminus of a primer strand; correspondingly, "upstream" refers to the known template and complementary primer sequence towards the 5' end of the primer strand; "leading strands" are those primer strands which have not previously undergone extension failure); and (iii) predict at each extension step the signal to be expected from the extension of the trailing strands through simulation of the occurrence of an extension failure at any point upstream from the 3' terminus of the leading strand. Subtraction of the predicted signal from the measured signal yields a signal due only to valid extension of the leading strand population.

In a preferred embodiment of the invention, the monitoring for reactive sequencing reaction errors is computer-aided. The ability to monitor extension failures permits determination of the point to which the trailing strands for a given template sequence have advanced and the sequence in the 1, 2 or 3 base gap between these strands and the leading strands. Knowing this information the dNTP probe cycle can be altered to selectively extend the trailing strands for a given template sequence while not extending the leading strands, thereby resynchronizing the populations.

The present invention further provides an apparatus for DNA sequencing comprising: (a) at least one chamber including a DNA primer/template system which produces a detectable signal when a DNA polymerase enzyme incorporates a deoxyribonucleotide monophosphate onto the 3' end of the primer strand; (b) means for introducing into, and evacuating from, the reaction chamber at least one selected from the group consisting of buffers, electrolytes, DNA template, DNA primer, deoxyribonucleotides, and polymerase enzymes; (c) means for amplifying said signal; and (d) means for, converting said signal into an electrical signal.

BRIEF DESCRIPTION OF DRAWINGS

Further objects and advantages of the invention will be apparent from a reading of the following description in conjunction with the accompanying drawings, in which.

DETAILED DESCRIPTION

Figure 1:
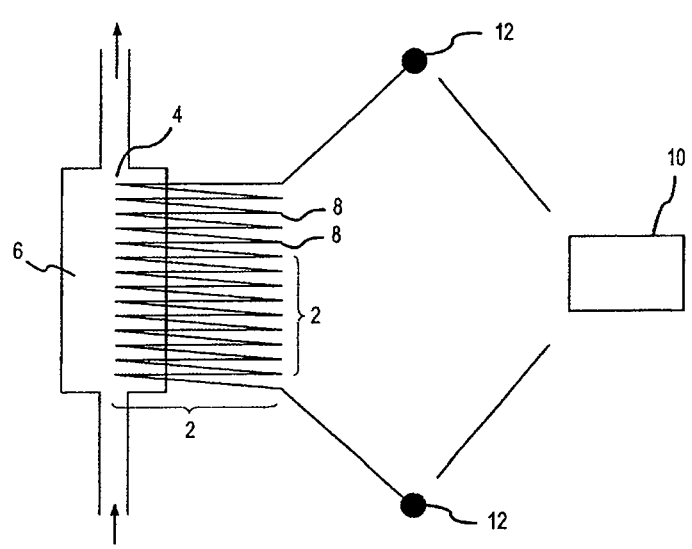
FIG. 1 is a schematic diagram illustrating a reactive sequencing device containing a thin film bismuth antimony thermopile in accordance with the invention.

The present invention provides a method for determining the nucleic acid sequence of a DNA molecule based on detection of successive single nucleotide DNA polymerase mediated extension reactions. As described in detail below, in one embodiment, a DNA primer/template system comprising a polynucleotide primer complementary to and bound to a region of the DNA to be sequenced is constrained within a reaction cell into which buffer solutions containing various reagents necessary for a DNA polymerase reaction to occur are added. Into the reaction cell, a single type of deoxynucleoside triphosphate (dNTP) is added. Depending on the identity of the next complementary site in the DNA primer/template system, an extension reaction will occur only when the appropriate nucleotide is present in the reaction cell. A correlation between the nucleotide present in the reaction cell and detection of an incorporation signal identifies the next nucleotide of the template. Following each extension reaction, the reaction cell is flushed with dNTP-free buffer, retaining the DNA primer/template system, and the cycle is repeated until the entire nucleotide sequence is identified.

The present invention is based on the existence of a control signal within the active site of DNA polymerases which distinguish, with high fidelity, complementary and non-complementary fits of incoming deoxynucleotide triphosphates to the base on the template strand at the primer extension site, i.e., to read the sequence, and to incorporate at that site only the one type of deoxynucleotide that is complementary. That is, if the available nucleotide type is not complementary to the next template site, the polymerase is inactive, thus, the template sequence is the DNA polymerase control signal. Therefore, by contacting a DNA polymerase system with a single nucleotide type rather than all four, the next base in the sequence can be identified by detecting whether or not a reaction occurs. Further, single base repeat lengths can be quantified by quantifying the extent of reaction.

As a first step in the practice of the inventive method, single-stranded template DNA to be sequenced is prepared using any of a variety of different methods known in the art. Two types of DNA can be used as templates in the sequencing reactions. Pure single-stranded DNA such as that obtained from recombinant bacteriophage can be used. The use of bacteriophage provides a method for producing large quantities of pure single stranded template. Alternatively, single-stranded DNA may be derived from double-stranded DNA that has been denatured by heat or alkaline conditions, as described in Chen and Subrung, (1985, DNA 4:165); Huttoi and Skaki (1986, Anal. Biochem. 152:232); and Mierendorf and Pfeffer, (1987, Methods Enzymol. 152:556), may be used. Such double stranded DNA includes, for example, DNA samples derived from patients to be used in diagnostic sequencing reactions.

The template DNA can be prepared by various techniques well known to those of skill in the art. For example, template DNA can be prepared as vector inserts using any conventional cloning methods, including those used frequently for sequencing. Such methods can be found in Sambrook et al., Molecular Cloning: A Laboratory Manual, Second Edition (Cold Spring Harbor Laboratories, New York, 1989). In a preferred embodiment of the invention, polymerase chain reactions (PCR) may be used to amplify fragments of DNA to be used as template DNA as described in Innis et al., ed. PCR Protocols (Academic Press, New York, 1990).

The amount of DNA template needed for accurate detection of the polymerase reaction will depend on the detection technique used. For example, for optical detection, e.g., fluorescence or chemiluminescence detection, relatively small quantities of DNA in the femtomole range are needed. For thermal detection quantities approaching one picomole may be required to detect the change in temperature resulting from a DNA polymerase mediated extension reaction.

In enzymatic sequencing reactions, the priming of DNA synthesis is achieved by the use of an oligonucleotide primer with a base sequence that is complementary to, and therefore capable of binding to, a specific region on the template DNA sequence. In instances where the template DNA is obtained as single stranded DNA from bacteriophage, or as double stranded DNA derived from plasmids, "universal" primers that are complementary to sequences in the vectors, i.e., the bacteriophage, cosmid and plasmid vectors, and that flank the template DNA, can be used.

Primer oligonucleotides are chosen to form highly stable duplexes that bind to the template DNA sequences and remain intact during any washing steps during the extension cycles. Preferably, the length of the primer oligonucleotide is from 18-30 nucleotides and contains a balanced base composition. The structure of the primer should also be analyzed to confirm that it does not contain regions of dyad symmetry which can fold and self anneal to form secondary structures thereby rendering the primers inefficient. Conditions for selecting appropriate hybridization conditions for binding of the oligonucleotide primers in the template systems will depend on the primer sequence and are well known to those of skill in the art.

In utilizing the reactive sequencing method of the invention, a variety of diffe to incorporate dNTPs onto the 3' end of the primer which is hybridized to the polymerases include but are not limited to Taq polymerase, T7 or T4 polyme preferred embodiment of the invention, described in detail below, DNA polyn proofreading activity are used in the sequencing reactions. For the most rapi polymerase is sufficient to ensure that each DNA molecule carries a non-co % molecule during reaction. For a typical equilibrium constant of ~50 nM for the equilibrium:

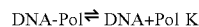

DNA-Pol ⇌ DNA+Pol K

The desired condition is [Pol]≥50 nM+[DNA].

In addition, reverse transcriptase which catalyzes the synthesis of single stranded DNA from an RNA template may be utilized in the reactive sequencing method of the invention to sequence messenger RNA (mRNA). Such a method comprises sequentially contacting an RNA template annealed to a primer (RNA primer/template) with dNTPs in the presence of reverse transcriptase enzyme to determine the sequence of the RNA. Because mRNA is produced by RNA polymerase-catalyzed synthesis from a DNA template, and thus contains the sequence information of the DNA template strand, sequencing the mRNA yields the sequence of the DNA gene from which it was transcribed. Eukaryotic mRNAs have poly(A) tails and therefore the primer for reverse transcription can be an oligo(dT). Typically, it will be most convenient to synthesize the oligo(dT) primer with a terminal biotin or amino group through which the primer can be captured on a substrate and subsequently hybridize to and capture the template mRNA strand.

The extension reactions are carried out in buffer solutions which contain the appropriate concentrations of salts, dNTPs and DNA polymerase required for the DNA polymerase mediated extension to proceed. For guidance regarding such conditions see, for example, Sambrook, et al., (1989, Molecular Cloning, A Laboratory Manual, Cold Spring Harbor Press, N.Y.); and Ausubel, et al (1989, Current Protocols in Molecular Biology, Green Publishing Associates and Wiley Interscience, N.Y.).

Typically, buffer containing one of the four dNTPs is added into a reaction cell. Depending on the identity of the nucleoside base at the next unpaired template site in the primer/template system, a reaction will occur when the reaction cell contains the appropriate dNTP. When the reaction cell contains any one of the other three incorrect dNTPs, no reaction will take place.

The reaction cell is then flushed with dNTP free buffer and the cycle is repeated until a complete DNA sequence is identified. Detection of a DNA polymerase mediated extension can be made using any of the detection methods described in detail below including optical and thermal detection of an extension reaction.

In some instances, a nucleotide solution is found to be contaminated with any of the other three nucleotides. In such instances a small fraction of strands may be extended by incorporation of an impurity dNTP when the dNTP type supplied is incorrect for extension, producing a population of strands which are subsequently extended ahead of the main strand population. Thus, in an embodiment of the invention, each nucleotide solution can be treated to remove any contaminated nucleotides. Treatment of each nucleotide solution involves reaction of the solution prior to use with immobilized DNA complementary to each the possibly contaminating nucleotides. For example, a dATP solution will be allowed to react with immobilized poly (dA), poly (dG) or poly (dC), with appropriate primers and polymerase, for a time sufficient to incorporate any contaminating dTTP, dCTP and dGTP nucleotides into DNA.

In a preferred embodiment of the invention, the primer/template system comprises the template DNA tethered to a solid phase support to permit the sequential addition of sequencing reaction reagents without complicated and time consuming purification steps following each extension reaction. Preferably, the template DNA is covalently attached to a solid phase support, such as the surface of a reaction flow cell, a polymeric microsphere, filter material, or the like, which permits the sequential application of sequencing reaction reagents, i.e., buffers, dNTPs and DNA polymerase, without complicated and time consuming purification steps following each extension reaction. Alternatively, for applications that require sequencing of many samples containing the same vector template or same gene, for example, in diagnostic applications, a universal primer may be tethered to a support, and the template DNA allowed to hybridize to the immobilized primer.

The DNA may be modified to facilitate covalent or non-covalent tethering of the DNA to a solid phase support. For example, when PCR is used to amplify DNA fragments, the 5' ends of one set of PCR primer oligonucleotides strands may be modified to carry a linker moiety for tethering one of the two complementary types of DNA strands produced to a solid phase support. Such linker moieties include, for example, biotin. When using biotin, the biotinylated DNA fragments may be bound non-covalently to streptavidin covalently attached to the solid phase support. Alternatively, an amino group (—NH$_2$) may be chemically incorporated into one of the PCR primer strands and used to covalently link the DNA template to a solid phase support using standard chemistry, such as reactions with N-hydroxysuccinimide activated agarose surfaces.

In another embodiment, the 5' ends of the sequencing oligonucleotide primer may be modified with biotin, for non-covalent capture to a streptavidin-treated support, or with an amino group for chemical linkage to a solid support; the template strands are then captured by the non-covalent binding attraction between the immobilized primer base sequence and the complementary sequence on the template strands. Methods for immobilizing DNA on a solid phase support are well known to those of skill in the art and will vary depending on the solid phase support chosen.

In the reactive sequencing method of the present invention, DNA polymerase is presented sequentially with each of the 4 dNTPs. In the majority of the reaction cycles, only incorrect dNTPs will be present, thereby increasing the likelihood of misincorporation of incorrect nucleotides into the extending DNA primer/template system.

Accordingly, the present invention further provides methods for optimizing the reactive sequencing reaction to achieve rapid and complete incorporation of the correct nucleotide into the DNA primer/template system, while limiting the misincorporation of incorrect nucleotides. For example, dNTP concentrations may be lowered to reduce misincorporation of incorrect nucleotides into the DNA primer. $K_m$ values for incorrect dNTPs can be as much as 1000-fold higher than for correct nucleotides, indicating that a reduction in dNTP concentrations can reduce the rate of misincorporation of nucleotides. Thus, in a preferred embodiment of the invention the concentration of dNTPs in the sequencing reactions are approximately 5-20 µM. At this concentration, incorporation rates are as close to the maximum rate of 400 nucleotides/s for T4 DNA polymerase as possible.

In addition, relatively short reaction times can be used to reduce the probability of misincorporation. For an incorporation rate approaching the maximum rate of ~400 nucleotides/s, a reaction time of approximately 25 milliseconds (ms) will be sufficient to ensure extension of 99.99% of primer strands.

In a specific embodiment of the invention, DNA polymerases lacking 3' to 5' exonuclease activity may be used for reactive sequencing to limit exonucleolytic degradation of primers that would occur in the absence of correct dNTPs. In the presence of all four dNTPs, misincorporation frequencies by DNA polymerases possessing exonucleolytic proofreading activity are as low as one error in 10$^6$ to 10$^8$ nucleotides incorporated as discussed in Echols and Goodman (1991, Annu. Rev. Biochem 60; 477-511); and Goodman, et al. (1993, Crit. Rev. Biochem. Molec. Biol. 28:83-126); and Loeb and Kunkel (1982, Annu. Rev. Biochem. 52:429-457). In the absence of proofreading, DNA polymerase error rates are typically on the order of 1 in 10$^4$ to 1 in 10$^6$. Although exonuclease activity increases the fidelity of a DNA polymerase, the use of DNA polymerases having proofreading activity can pose technical difficulties for the reactive sequencing method of the present invention. Not only will the exonuclease remove any misincorporated nucleotides, but also, in the absence of a correct dNTP complementary to the next template base, the exonuclease will remove correctly-paired nucleotides successively until a point on the template sequence is reached where the base is complementary to the dNTP in the reaction cell. At this point, an idling reaction is established where the polymerase repeatedly incorporates the correct dNMP and then removes it. Only when a correct dNTP is present will the rate of polymerase activity exceed the exonuclease rate so that an idling reaction is established that maintains the incorporation of that correct nucleotide at the 3' end of the primer.

A number of T4 DNA polymerase mutants containing specific amino acid substitutions possess reduced exonuclease activity levels up to 10,000-fold less than the wild-type enzyme. For example, Reha-Krantz and Nonay (1993, J. Biol. Chem. 268:27100-17108) report that when Asp 112 was replaced with Ala and Glu 114 was replaced with Ala (D112A/E114A) in T4 polymerase, these two amino acid substitutions reduced the exonuclease activity on double stranded DNA by a factor of about 300 relative to the wild type enzyme. Such mutants may be advantageously used in the practice of the invention for incorporation of nucleotides into the DNA primer/template system.

In yet another embodiment of the invention, DNA polymerases which are more accurate than wild type polymerases at incorporating the correct nucleotide into a DNA primer/template may be used. For example, in a (D112A/E114A) mutant T4 polymerase with a third mutation where Ile 417 is replaced by Val (I417V/D112A/E114A), the I417V mutation results in an antimutator phenotype for the polymerase (Reha-Krantz and Nonay, 1994, J. Biol. Chem. 269:5635-5643; Stocki et al., 1995, Mol. Biol. 254:15-28). This antimutator phenotype arises because the polymerase tends to move the primer ends from the polymerase site to the exonuclease site more frequently and thus proof read more frequently than the wild type polymerase, and thus increases the accuracy of synthesis.

In yet another embodiment of the invention, polymerase mutants that are capable of more efficiently incorporating fluorescent-labeled nucleotides into the template DNA system molecule may be used in the practice of the invention. The efficiency of incorporation of fluorescent-labeled nucleotides may be reduced due to the presence of bulky fluorophore labels that may inhibit dNTP interaction at the active site of the polymerase. Polymerase mutants that may be advantageously used for incorporation of fluorescent-labeled dNTPs into DNA include but are not limited to those described in U.S. application Ser. No. 08/632,742 filed Apr. 16, 1996 which is incorporated by reference herein.

In a preferred embodiment of the invention, the reactive sequencing method utilizes a two cycle system. An exonuclease-deficient polymerase is used in the first cycle and a mixture of exonuclease-deficient and exonuclease-proficient enzymes are used in the second cycle. In the first cycle, the primer/template system together with an exonuclease-deficient polymerase will be presented sequentially with each of the four possible nucleotides. Reaction time and conditions will be such that a sufficient fraction of primers are extended to allow for detection and quantification of nucleotide incorporation, ~98%, for accurate quantification of multiple single-base repeats. In the second cycle, after identification of the correct nucleotide, a mixture of exonuclease proficient and deficient polymerases, or a polymerase containing both types of activity will be added in a second cycle together with the correct dNTP identified in the first cycle to complete and proofread the primer extension. In this way, an exonuclease-proficient polymerase is only present in the reaction cell when the correct dNTP is present, so that exonucleolytic degradation of correctly extended strands does not occur, while degradation and correct re-extension of previously incorrectly extended strands does occur, thus achieving extremely accurate strand extension.

The detection of a DNA polymerase mediated extension reaction can be accomplished in a number of ways. For example, the heat generated by the extension reaction can be measured using a variety of different techniques such as those employing thermopile, thermistor and refractive index measurements.

In an embodiment of the invention, the heat generated by a DNA polymerase mediated extension reaction can be measured. For example, in a reaction cell volume of 100 micrometers$^3$ containing 1 µg of water as the sole thermal mass and $2 \times 10^{11}$ DNA template molecules (300 fmol) tethered within the cell, the temperature of the water increases by $1 \times 10^{3 \circ}$ C. for a polymerase reaction which extends the primer by a single nucleoside monophosphate. This calculation is based on the experimental determination that a one base pair extension in a DNA chain is an exothermic reaction and the enthalpy change associated with this reaction is 3.5 kcal/mole of base. Thus extension of 300 fmol of primer strands by a single base produces 300 fmol×3.5 kcal/mol or $1 \times 10^{-9}$ cal of heat. This is sufficient to raise the temperature of 1 pg of water by $1 \times 10^{-3 \circ}$ C. Such a temperature change can be readily detectable using thermistors (sensitivity <$10^\circ$ C.), thermopiles (sensitivity <$10^{-5 \circ}$ C.); and refractive index measurements (sensitivity <$10^\circ$ C.).

In a specific embodiment of the invention, thermopiles may be used to detect temperature changes. Such thermopiles are known to have a high sensitivity to temperature and can make measurements in the tens of micro-degree range in several second time constants. Thermopiles may be fabricated by constructing serial sets of junctions of two dissimilar metals and physically arranging the junctions so that alternating junctions are separated in space. One set of junctions is maintained at a constant reference temperature, while the alternate set of junctions is located in the region whose temperature is to be sensed. A temperature difference between the two sets of junctions produces a potential difference across the junction set which is proportional to the temperature difference, to the thermoelectric coefficient of the junction and to the number of junctions. For optimum response, bimetallic pairs with a large thermoelectric coefficient are desirable, such as bismuth and antimony. Thermopiles may be fabricated using thin film deposition techniques in which evaporated metal vapor is deposited onto insulating substrates through specially fabricated masks. Thermopiles that may be used in the practice of the invention include thermopiles such as those described in U.S. Pat. No. 4,935,345, which is incorporated by reference herein.

In a specific embodiment of the invention, miniature thin film thermopiles produced by metal evaporation techniques, such as those described in U.S. Pat. No. 4,935,345 incorporated herein by reference, may be used to detect the enthalpy changes. Such devices have been made by vacuum evaporation through masks of about 10 mm square. Using methods of photolithography, sputter etching and reverse lift-off techniques, devices as small as 2 mm square may be constructed without the aid of modern microlithographic techniques. These devices contain 150 thermoelectric junctions and employ 12 micron line widths and can measure the exothermic heat of reaction of enzyme-catalyzed reactions in flow streams where the enzyme is preferably immobilized on the surface of the thermopile.

To incorporate thermopile detection technology into a reactive sequencing device, thin-film bismuth-antimony thermopiles 2, as shown in FIG. 1, may be fabricated by successive electron-beam evaporation of bismuth and antimony metals through two different photolithographically-generated masks in order to produce a zigzag array of alternating thin bismuth and antimony wires which are connected to form two sets of bismuth-antimony thermocouple junctions. Modern microlithographic techniques will allow fabrication of devices at least one order of magnitude smaller than those previously made, i.e., with line widths as small as 1 ўm and overall dimensions on the order of 100 µm². One set of junctions 4 (the sensor junctions) is located within the reaction cell 6, i.e., deposited on a wall of the reaction cell, while the second reference set of junctions 8 is located outside the cell at a reference point whose temperature is kept constant. Any difference in temperature between the sensor junctions and the reference junctions results in an electric potential being generated across the device, which can be measured by a high-resolution digital voltmeter 10 connected to measurement points 12 at either end of the device. It is not necessary that the temperature of the reaction cell and the reference junctions be the same in the absence of a polymerase reaction event, only that a change in the temperature of the sensor junctions due to a polymerase reaction event be detectable as a change in the voltage generated across the thermopile.

Figure 2:
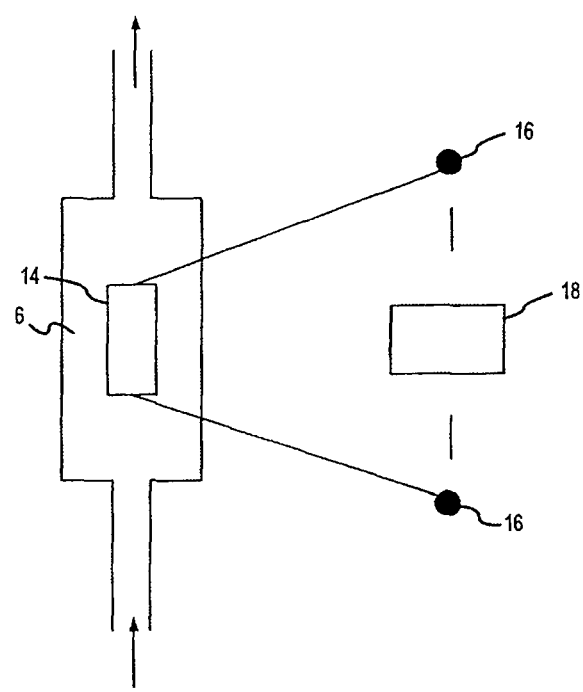
FIG. 2 is a schematic diagram of a reactive sequencing device containing a thermistor in accordance with the invention.

In addition to thermopiles, as shown in FIG. 2, a thermistor 14 may also be used to detect temperature changes in the reaction cell 6 resulting from DNA polymerase mediated incorporation of dNMPs into the DNA primer strand. Thermistors are semiconductors composed of a sintered mixture of metallic oxides such as manganese, nickel, and cobalt oxides. This material has a large temperature coefficient of resistance, typically 4% per ° C., and so can sense extremely small temperature changes when the resistance is monitored with a stable, high-resolution resistance-measuring device such as a digital voltmeter, e.g., Keithley Instruments Model 2002. A thermistor 14, such as that depicted in FIG. 2, may be fabricated in the reactive sequencing reaction cell by sputter depositing a thin film of the active thermistor material onto the surface of the reaction cell from a single target consisting of hot pressed nickel, cobalt and manganese oxides. Metal interconnections 16 which extend out beyond the wall of the reaction cell may also be fabricated in a separate step so that the resistance of the thermistor may be measured using an external measuring device 18.

Temperature changes may also be sensed using a refractive index measurement technique. For example, techniques such as those described in Bornhop (1995, Applied Optics 34:3234-323) and U.S. Pat. No. 5,325,170, may be used to detect refractive index changes for liquids in capillaries. In such a technique, a low-power He—Ne laser is aimed off-center at a right angle to a capillary and undergoes multiple internal reflection. Part of the beam travels through the liquid while the remainder reflects only off the external capillary wall. The two beams undergo different phase shifts depending on the refractive index difference between the liquid and capillary. The result is an interference pattern, with the fringe position extremely sensitive to temperature-induced refractive index changes.

In a further embodiment of the invention, the thermal response of the system may be increased by the presence of inorganic pyrophosphatase enzyme which is contacted with the template system along with the dNTP solution. Additionally, heat is released as the pyrophosphate released from the dNTPs upon incorporation into the template system is hydrolyzed by inorganic pyrophosphatase enzyme.

In another embodiment, the pyrophosphate released upon incorporation of dNTP's may be removed from the template system and hydrolyzed, and the resultant heat detected, using thermopile, thermistor or refractive index methods, in a separate reaction cell downstream. In this reaction cell, inorganic pyrophosphatase enzyme may be mixed in solution with the dNTP removed from the DNA template system, or alternatively the inorganic pyrophosphatase enzyme may be covalently tethered to the wall of the reaction cell.

Alternatively, the polymerase-catalyzed incorporation of a nucleotide base can be detected using fluorescence and chemiluminescence detection schemes. The DNA polymerase mediated extension is detected when a fluorescent or chemiluminescent signal is generated upon incorporation of a fluorescently or chemiluminescently labeled dNMP into the extending DNA primer strand. Such tags are attached to the nucleotide in such a way as to not interfere with the action of the polymerase. For example, the tag may be attached to the nucleotide base by a linker arm sufficiently long to move the bulky fluorophore away from the active site of the enzyme.

For use of such detection schemes, nucleotide bases are labeled by covalently attaching a compound such that a fluorescent or chemiluminescent signal is generated following incorporation of a dNTP into the extending DNA primer/ template. Examples of fluorescent compounds for labeling dNTPs include but are not limited to fluorescein, rhodamine, and BODIPY (4,4-difluoro-4-bora-3a,4a-diaza-s-indacene). See "Handbook of Molecular Probes and Fluorescent Chemicals", available from Molecular Probes, Inc. (Eugene, Oreg.). Examples of chemiluminescence based compounds that may be used in the sequencing methods of the invention include but are not limited to luminol and dioxetanones (See, Gundennan and McCapra, "Chemiluminescence in Organic Chemistry", Springer-Verlag, Berlin Heidleberg, 1987).

Fluorescently or chemiluminescently labeled dNTPs are added individually to a DNA template system containing template DNA annealed to the primer, DNA polymerase and the appropriate buffer conditions. After the reaction interval, the excess dNTP is removed and the system is probed to detect whether a fluorescent or chemiluminescent tagged nucleotide has been incorporated into the DNA template. Detection of the incorporated nucleotide can be accomplished using different methods that will depend on the type of tag utilized.

For fluorescently-tagged dNTPs the DNA template system may be illuminated with optical radiation at a wavelength which is strongly absorbed by the tag entity. Fluorescence from the tag is detected using for example a photodetector together with an optical filter which excludes any scattered light at the excitation wavelength.

Since labels on previously incorporated nucleotides would interfere with the signal generated by the most recently incorporated nucleotide, it is essential that the fluorescent tag be removed at the completion of each extension reaction. To facilitate removal of a fluorescent tag, the tag may be attached to the nucleotide via a chemically or photochemically cleavable linker using methods such as those described by Metzger, M. L., et al. (1994, Nucleic Acids Research 22:4259-4267) and Burgess, K., et al., (1997, J. Org. Chem. 62:5165-5168) so that the fluorescent tag may be removed from the DNA template system before a new extension reaction is carried out.

In a further embodiment utilizing fluorescent detection, the fluorescent tag is attached to the dNTP by a photocleavable or chemically cleavable linker, and the tag is detached following the extension reaction and removed from the template system into a detection cell where the presence, and the amount, of the tag is determined by optical excitation at a suitable wavelength and detection of fluorescence. In this embodiment, the possibility of fluorescence quenching, due to the presence of multiple fluorescent tags immediately adjacent to one another on a primer strand which has been extended complementary to a single base repeat region in the template, is minimized, and the accuracy with which the repeat number can be determined is optimized. In addition, excitation of fluorescence in a separate chamber minimizes the possibility of photolytic damage to the DNA primer/template system. In an additional embodiment utilizing fluorescent detection, the signal from the fluorescent tag can be destroyed using a chemical reaction which specifically targets the fluorescent moiety and reacts to form a final product which is no longer fluorescent. In this embodiment, the fluorescent tag attached to the nucleotide base is destroyed following extension and detection of the fluorescence signal, without the removal of the tag. In a specific embodiment, fluorophores attached to dNTP bases may be selectively destroyed by reaction with compounds capable of extracting an electron from the excited state of the fluorescent moiety thereby producing a radical ion of the fluorescent moiety which then reacts to form a final product which is no longer fluorescent. In a further specific embodiment, the signal from a fluorescent tag is destroyed by photochemical reaction with the cation of a diphenyliodonium salt following extension and detection of the fluorescence label. The fluorescent tag attached to the incorporated nucleotide base is destroyed, without removal of the tag, by the addition of a solution of a diphenyliodonium salt to the reaction cell and subsequent UV light exposure. The diphenyliodonium salt solution is removed and the reactive sequencing is continued. This embodiment does not require dNTP's with chemically or photochemically cleavable linkers, since the fluorescent tag need not be removed.

In a further embodiment of the technique, the response generated by a DNA polymerase-mediated extension reaction can be amplified. In this embodiment, the dNTP is chemically modified by the covalent attachment of a signaling tag through a linker that can be cleaved either chemically or photolytically. Following exposure of the dNTP to the primer/template system and flushing away any unincorporated chemically modified dNTP, any signaling tag that has been incorporated is detached by a chemical or photolytic reaction and flushed out of the reaction chamber to an amplification chamber in which an amplified signal may be produced and detected.

A variety of methods may be used to produce an amplified signal. In one such catalytic function. When the catalytic tag is cleaved and allowed to react with chemical reaction ensue producing many moles of product per mole of catalytic multiplication of reaction enthalpy. Either the reaction product is detected, the color or absorbency, or the amplified heat product is detected by a thermal signal that is covalently attached to the dNTP via a cleavable linker arm of sufficient length that does not interfere with the active site of the polymerase enzyme. Following incorporation that enzyme is detached and transported to a second reactor volume in which specific substrate, thus an amplified response is obtained as each enzyme of reaction. For example, the enzyme catalase (CAT) catalyzes the reaction:

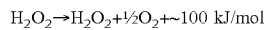

$$H_2O_2 \xrightarrow{CAT} H_2O_2 + \tfrac{1}{2}O_2 + \sim 100 \text{ kJ/mol}$$

If each dNTP is tagged with a catalase molecule which is detached after dNMP incorporation and allowed to react downstream with hydrogen peroxide, each nucleotide incorporation would generate ~25 kcal/mol×N of heat where N is the number of hydrogen peroxide molecules decomposed by the catalase. The heat of decomposition of hydrogen peroxide is already ~6-8 times greater than for nucleotide incorporation, (i.e. 3.5-4 kcal/mol). For decomposition of ~150 hydrogen peroxide molecules the amount of heat generated per base incorporation approaches 1000 times that of the unamplified reaction. Similarly, enzymes which produce colored products, such as those commonly used in enzyme-linked immunosorbent assays (ELISA) could be incorporated as detachable tags. For example the enzyme alkaline phosphatase converts colorless p-nitrophenyl phosphate to a colored product (p-nitrophenol); the enzyme horseradish peroxidase converts colorless o-phenylenediamine hydrochloride to an orange product. Chemistries for linking these enzymes to proteins such as antibodies are well-known to those versed in the art, and could be adapted to link the enzymes to nucleotide bases via linker arms that maintain the enzymes at a distance from the active site of the polymerase enzymes.

In a further embodiment, an amplified thermal signal may be produced when the signaling tag is an entity which can stimulate an active response in cells which are attached to, or held in the vicinity of, a thermal sensor such as a thermopile or thermistor. Pizziconi and Page (1997, Biosensors and Bioelectronics 12:457-466) reported that harvested and cultured mast cell populations could be activated by calcium ionophore to undergo exocytosis to release histamine, up to 10-30 pg (100-300 fmol) per cell. The multiple cell reactions leading to exocytosis are themselves exothermic. This process is further amplified using the enzymes diamine oxidase to oxidize the histamine to hydrogen peroxide and imidazoleacetaldehyde, and catalase to disproportionate the hydrogen peroxide. Two reactions together liberate over 100 kJ of heat per mole of histamine. For example, a calcium ionophore is covalently attached to the dNTP base via a linker arm which distances the linked calcium ionophore from the active site of the polymerase enzyme and is chemically or photochemically cleavable. Following the DNA polymerase catalyzed incorporation step, and flushing away unincorporated nucleotides any calcium ionophore remaining bound to an incorporated nucleotide may be cleaved and flushed downstream to a detection chamber containing a mast cell-based sensor such as described by Pizziconi and Page (1997, Biosensors and Bioelectronics 12:457-466). The calcium ionophore would bind to receptors on the mast cells stimulating histamine release with the accompanying generation of heat. The heat production could be further amplified by introducing the enzymes diamine oxidase to oxidize the histamine to hydrogen peroxide and imidazoleacetaldehyde, and catalase to disproportionate the hydrogen peroxide. Thus a significantly amplified heat signal would be produced which could readily be detected by a thermopile or thermistor sensor within, or in contact with, the reaction chamber.

In a further embodiment utilizing chemiluminescent detection, the chemiluminescent tag is attached to the dNTP by a photocleavable or chemically cleavable linker. The tag is detached following the extension reaction and removed from the template system into a detection cell where the presence, and the amount, of the tag is determined by an appropriate chemical reaction and sensitive optical detection of the light produced. In this embodiment, the possibility of a non-linear optical response due to the presence of multiple chemiluminescent tags immediately adjacent to one another on a primer strand which has been extended complementary to a single base repeat region in the template, is minimized, and the accuracy with which the repeat number can be determined is optimized. In addition, generation of chemiluminescence in a separate chamber minimizes chemical damage to the DNA primer/template system, and allows detection under harsh chemical conditions which otherwise would chemically damage the DNA primer/template. In this way, chemiluminescent tags can be chosen to optimize chemiluminescence reaction speed, or compatibility of the tagged dNTP with the polymerase enzyme, without regard to the compatibility of the chemiluminescence reaction conditions with the DNA primer/template.

In a further embodiment of the invention, the concentration of the dNTP solution removed from the template system following each extension reaction can be measured by detecting a change in UV absorption due to a change in the concentration of dNTPs, or a change in fluorescence response of fluorescently-tagged dNTPs. The incorporation of nucleotides into the extended template would result in a decreased concentration of nucleotides removed from the template system. Such a change could be detected by measuring the UV absorption of the buffer removed from the template system following each extension cycle.

In a further embodiment of the invention, extension of the primer strand may be sensed by a device capable of sensing fluorescence from, or resolving an image of, a single DNA molecule. Devices capable of sensing fluorescence from a single molecule include the confocal microscope and the near-field optical microscope. Devices capable of resolving an image of a single molecule include the scanning tunneling microscope (STM) and the atomic force microscope (AFM).

In this embodiment of the invention, a single DNA template molecule with attached primer is immobilized on a surface and viewed with an optical microscope or an STM or AFM before and after exposure to buffer solution containing a single type of dNTP, together with polymerase enzyme and other necessary electrolytes. When an optical microscope is used, the single molecule is exposed serially to fluorescently-tagged dNTP solutions and as before incorporation is sensed by detecting the fluorescent tag after excess unreacted dNTP is removed. Again as before, the incorporated fluorescent tag must be cleaved and discarded before a subsequent tag can be detected. Using the STM or AFM, the change in length of the primer strand is imaged to detect incorporation of the dNTP. Alternatively the dNTP may be tagged with a physically bulky molecule, more readily visible in the STM or AFM, and this bulky tag is removed and discarded before each fresh incorporation reaction.

When sequencing a single molecular template in this way, the possibility of incomplete reaction producing erroneous signal and out-of-phase strand extension, does not exist and the consequent limitations on read length do not apply. For a single molecular template, reaction either occurs or it does not, and if it does not, then extension either ceases and is known to cease, or correct extension occurs in a subsequent cycle with the correct dNTP. In the event that an incorrect nucleotide is incorporated, which has the same probability as more the multiple strand processes discussed earlier, for example 1 in 1,000, an error is recorded in the sequence, but this error does not propagate or affect subsequent readout and so the read length is not limited by incorrect incorporation.

Detection and Compensation for DNA Polymerase Errors

In the reactive sequencing process, extension failures will typically arise due to the kinetics of the extension reaction and limitations on the amount of time allotted for each extension trial with the single deoxynucleotide triphosphates (dNTP's). When reaction is terminated by flushing away the dNTP supply, some small fraction of the primer strands may remain unextended. These strands on subsequent dNTP reaction cycles will continue to extend but will be out of phase with the majority strands, giving rise to small out-of-phase signals (i.e. signaling a positive incorporation for an added dNTP which is incorrect for extension of the majority strands). Because extension failure can occur, statistically, on any extension event, these out-of-phase signals will increase as the population of strands with extension failures grows. Ultimately the out-of-phase signal becomes comparable in amplitude with the signal due to correct extension of the majority strands and the sequence may be unreadable. The length by which the primer has been extended when the sequence becomes unreadable is known as the sequencing read length.

The present invention relates to a method that can extend the sequencing read length in two ways, first, by discriminating between the in-phase and out-of-phase signals, and second by calculating where, and how, a dNTP probe sequence can be altered so as selectively to extend the out-of-phase strands to bring them back into phase with the majority strands.

Specifically, a method is provided for discriminating between the in-phase and out-of-phase sequencing signals comprising: (i) detecting and measuring error signals thereby determining the size of the trailing strand population; (ii) between the 3' terminus of the trailing strand primers and the 3' terminus of the leading strand primers; (iii) simulating the occurrence of an extension failure at a point upstream from the 3' terminus of the leading strands thereby predicting at each extension step the exact point in the sequence previously traversed by the leading strands to which the 3' termini of the trailing strands have been extended; (iv) predicting for each dNTP introduced the signal to be expected from correct extension of the trailing strands; and (v) subtracting the predicted signal from the measured signal to yield a signal due only to correct extension of the leading strand population.

"Upstream" refers to the known sequence of bases correctly incorporated onto the primer strands. "Downstream" refers to the sequence beyond the 3' terminus. Thus for the leading strand population the downstream sequence is unknown but is predetermined by the sequence of the template strand that has not yet been read; for the trailing strand population, the downstream sequence is known for the gap between the 3' termini of the trailing and leading strands.

The gap between the leading and trailing primer strands may be 1, 2 or 3 bases (where a single base repeat of any length, e.g. AAAA, is counted as a single base because the entire repeat will be traversed in a single reaction cycle if the correct dNTP is introduced), but can never exceed 3 bases nor shrink spontaneously to zero if the reaction cycle of the four dNTP's is unchanged and no other reaction errors occur, for example a second extension failure on the same primer strand. If the reaction cycle of the four dNTP's is unchanged, it may readily be understood that a primer strand which has failed to extend when the correct dNTP, for example dATP, is in the reaction chamber cannot trail the leading (majority) strands (which did extend) by more than 3 bases, because the fourth base in the dNTP reaction cycle will always once again be the correct base (dATP) for the strand which failed to extend previously. Similarly, a trailing strand resulting from an extension failure can never re-synchronize with the leading strands if extension subsequently proceeds correctly, because the leading strands will always have extended by at least one more nucleotide—G, T, or C in the example discussion of an A extension failure—before the trailing strand can add the missing A. The effect is that after each complete dNTP cycle the trailing strands always follow the leading strands by an extension amount that represents the bases added in one complete dNTP cycle at a given point in the sequence. A further consequence is that all trailing strands that have undergone a single failure are in phase with each other regardless of the point at which the extension failure occurred.

The methods described herein may be utilized to significantly extend the read length that can be achieved by the technique of reactive sequencing by providing a high level of immunity to erroneous signals arising from extension failure. In a preferred embodiment of the invention, the discrimination method of the invention is computer based.

First, determination of the readout signals allows real-time discrimination between the signals due to correct extension of the leading strand population and error signals arising from extension of the population of trailing strands resulting from extension failure. Using this information, accurate sequence readout can be obtained significantly beyond the point at which the trailing strand signals would begin to mask the correct leading strand signals. In fact, because the trailing strand signals can always be distinguished from the leading strand signals, it is possible to allow the trailing strand population to continue to grow, at the expense of the leading strands, to the point where the sequence is read from the signals generated on the trailing strand population, and the leading strand signals are treated as error signals to be corrected for. Ultimately, as the probability that a primer strand will have undergone at least one extension failure approaches unity, the signals from the leading strand population will disappear. Correspondingly the probability will increase that a trailing strand will undergo a second extension failure; the signals from this second population of double failure strands can be monitored and the single failure strand signals corrected in just the same way as the zero failure strand signals were corrected for signals due to single failure strands.

Second, because knowledge of the leading strand sequence permits one to know the point to which the trailing strands have advanced, by simulating the effect of an extension failure on that known sequence in a computer, and also to know the sequence in the 1, 2 or 3 base gap between these strands and the leading strands, then for a given template sequence the dNTP probe cycle can be altered at any point to selectively extend the trailing strands while not extending the leading strands, thereby resynchronizing the populations. Alternatively the gap between leading and trailing strands can be simulated in the computer and the gap can be eliminated by reversing the dNTP cycle whenever the gap shrinks to a single base. These processes are referred to as "healing." If a large number of different sequences are being read in parallel with the same dNTP reagents, an altered dNTP probe cycle that is correct for healing extension failure strands on a given sequence may not be correct for healing other sequences. However, with a large enough number of parallel sequence readouts, roughly one-third of the sequences will have trailing strands with a 1-base gap at any point, and so reversal of the dNTP probe cycle at arbitrary intervals will heal roughly one-third of the readouts with extension failure gaps. Repeated arbitrary reversal of the dNTP probe cycle eventually heals roughly two-thirds of all the readouts. The overall effect of these error correction and error elimination processes is to reduce, or eliminate any limitation on read length arising from extension failure.

The ability to overcome the read length limitations imposed by extension failure provides significant additional flexibility in experimental design. For example, it may be that read length is not limited by extension failure, but rather by misincorporation of incorrect nucleotides, which shuts down extension on the affected strands and steadily reduces the signal, ultimately to the point where it is not detectable with the desired accuracy. In this case, the ability to eliminate the effects of extension failure allows the experimenter great flexibility to alter the reaction conditions in such a way that misincorporation is minimized, at the expense of an increased incidence of extension failure. Misincorporation frequency depends in part on the concentration of the probing dNTP's and the reaction time allowed. Longer reaction times, or higher dNTP concentrations result in an increased probability of misincorporation, but a reduced incidence of extension failure. Therefore, if a higher level of extension failure can be tolerated due to, for example, the computer-aided signal discrimination and dNTP cycle-reversal healing methods, then reaction times and/or dNTP reagent concentrations can be reduced to minimize misincorporation, with the resulting increase in extension failure being countered by the computer-aided signal discrimination and/or dNTP cycle-reversal healing techniques described above.

If the deoxyribonucleotides used for the polymerase reaction are impure a small fraction of strands will extend when the main nucleotide is incorrect and produce a population of leading, rather than trailing, error strands. As with the trailing strands, the leading strand population is never more than three bases, nor less than one base, ahead of the main population, unless a second error occurs on the same strand, and also, regardless of where an incorrect extension by an impurity dNTP occurs, the leading strands are all in phase with each other. A given base site can be probed either 1, 2 or 3 times with an incorrect dNTP before it must be extended by the correct dNTP, so on the average twice. If each of the incorrect dNTP's is assumed to carry the same percentage of dNTP impurity, then the probability of incorrect extension by, e.g. 99% pure dNTP containing the correct complementary base as an impurity is 1% divided by 3 (only ⅓ of the impurity will be the correct complementary base)×2 (average 2 incorrect trials between each correct extension), that is, 0.67%.

Figure 15:
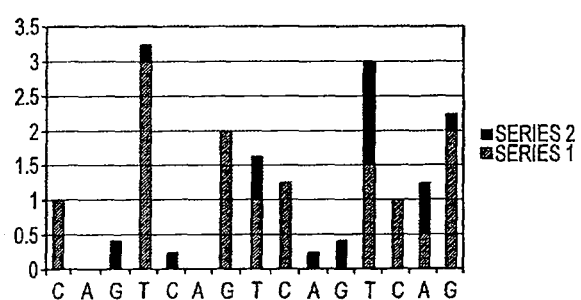
FIG. 15. Effect of a leading strand population on extension signals.

As with trailing strands, the leading strand population can produce out-of-phase extension signals that complicate the readout of the majority strand sequence, as shown in FIG. 15. Because the sequence downstream of the 3' terminus of the majority strands is not known at the time of extension of those strands, the signal due to leading strand extension can not immediately be corrected for, nor can an altered dNTP cycle be calculated which would automatically heal the gap between majority and leading strands for a given template sequence. However similar methods can be used to ameliorate the effects of a leading strand population. First, as with trailing strands, reversal of the dNTP probe cycle automatically heals the gap between leading and majority strand populations whenever the gap shrinks to a single base. Therefore, arbitrary reversal of the dNTP probe cycle has a ⅓ probability of healing the gap for a given sequence, or will heal ⅓ of the sequences in a large population of sequences probed in parallel. Continued arbitrary reversal eventually heals roughly two-thirds of such gaps. Second, although the sequence downstream of the 3' terminus of the majority strands is not immediately known, information about this sequence becomes available as soon as the majority strands traverse the gap region. Therefore, for each extension of the majority strands it is possible, ideally using a computer simulation, to calculate when the leading strand population would have traversed that base and thus the signal by which a prior extension of the majority strands would have been contaminated. In this way the majority strand extension signals can retrospectively be corrected for leading strand signals.

There are important aspects to leading strand creation that reduce the frequency of occurrence of leading strand events. First, if the concentration of impurity dNTP's is sufficiently low, a leading strand population cannot be created by impurity extension of the first base of a repeat. This is because the probability of incorrect incorporation of two impurity bases on the same strand in the same reaction cycle is the square of the probability for a single incorporation, and therefore vanishingly small for small impurity levels. Therefore, whenever the correct dNTP for extension of the repeat length is supplied, all strands will be extended to completion when the correct nucleotide is supplied, regardless of whether some fraction of the strands were already partially extended by one base of the repeat. Second, not all incorrect extensions result in a permanent phase difference. For a permanent phase difference to result, a second extension (by a correct base) must occur on the leading strand before the main strands extend to catch up to the leading strand. Labeling the next four sites along the template sequence: 1, 2, 3, 4, then, by definition, if a leading strand is created by incorporation of an impurity base on site 1 while the majority of the strands do not extend, the main nucleotide supplied is incorrect for extension at site 1. If the main nucleotide supplied is correct for extension at site 2, a 2-base lead is created. There is 1 chance in 4 that the reaction chamber contains the correct nucleotide for site 2, so the probability of creating a 2-base extension in a single step (with an impurity extension followed by a correct extension) is ¼ the probability of the impurity extension alone. For the 0.67% impurity extension probability cited above, this means a 0.16% probability of creating a 2-base extension in a single cycle.

However, if the main nucleotide supplied is incorrect for further extension at site 2, and, by definition incorrect for extension at site 1, then for the lead to become fixed, the correct nucleotide for site 2 must be supplied before the correct nucleotide to extend at site 1. The probability that site 2 will extend before site 1 is therefore 50%; for a 0.67% impurity extension probability, the probability that this creates a fixed lead due to a second extension by a correct nucleotide is 0.33%. Overall, a 1% impurity level results in ~0.5% probability of creating a leading strand in any given reaction trial.

Preparation of specific embodiments in accordance with the present invention will now be described in further detail. These examples are intended to be illustrative and the invention is not limited to the specific materials and methods set forth in these embodiments.

Example 1

Figure 3:
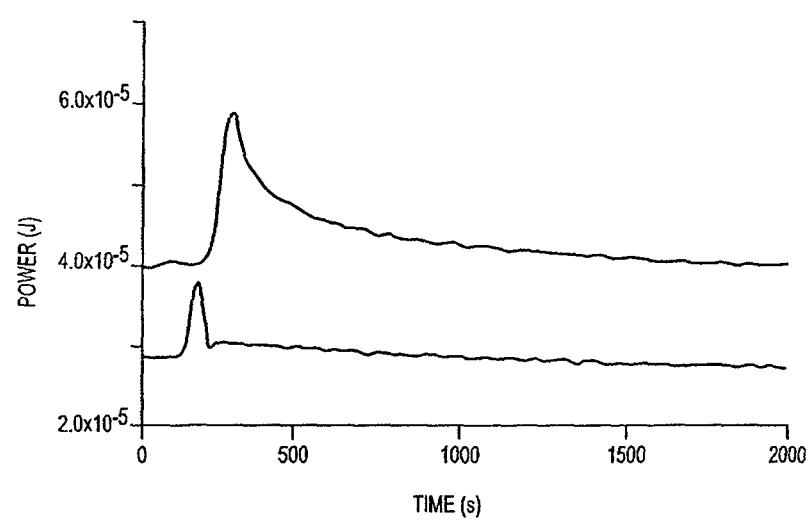
FIG. 3 is a schematic diagram illustrating a representative embodiment of micro calorimetry detection of a DNA polymerase reaction in accordance with the invention.

A microcalorimetic experiment was performed which demonstrates for the first time the successful thermal detection of a DNA polymerase reaction. The results are shown in FIG. 3. Approximately 20 units of 17 Sequenase was injected into a 3 mL reaction volume containing approximately 20 nmol of DNA template and complementary primer, and an excess of dNTPs. The primer was extended by 52-base pairs, the expected length given the size of the template. Using a commercial microcalorimeter (TAM Model 2273; Thermometrics, Sweden) a reaction enthalpy of 3.5-4 kcal per mole of base was measured (FIG. 3). This measurement is well within the value required for thermal detection of DNA polymerase activity. This measurement also demonstrates the sensitivity of thermopile detection as the maximum temperature rise in the reaction cell was $1\times10^{-3}$ C. The lower trace seen in FIG. 3 is from a reference cell showing the injection artifact for an enzyme-free injection into buffer containing no template system.

Example 2

To illustrate the utility of mutant T4 polymerases, two primer extension assays were performed with two different mutant T4 polymerases, both of which are exonuclease deficient. In one mutant, Asp112 is replaced with Ala and Glu114 is replaced with Ala (D112A/E114A). The exonuclease activity of this mutant on double-stranded DNA is reduced by a factor of about 300 relative to the wild type enzyme as described by Reha-Krantz and Nonay (1993, J. Biol. Chem. 268:27100-27108). In a second polymerase mutant, in addition to the DI12A/E114A amino acid substitutions, a third substitution replace Ile417 with Val (I417V/D112A/E114A). The I417V mutation increases the accuracy of synthesis by this polymerase (Stocki, S. A. and Reha-Krantz, L. J, 1995, J. Mol. Biol. 245:15-28; Reha-Krantz, L. J. and Nonay, R. L., 1994, J. Biol. Chem. 269:5635-5643).

Two separate primer extension reactions were carried out using each of the polymerase mutants. In the first, only a single correct nucleotide, dGTP, corresponding to a template C was added; The next unpaired template site is a G so that misincorporation would result in formation of a G-G mispair. A G-G mispair tends to be among the most difficult mispairs for polymerases to make. In the second primer extension reaction, two nucleotides, dGTP and dCTP, complementary to the first three unpaired template sites were added. Following correct incorporation of dGMP and dCMP, the next available template site is a T. Formation of C-T mispairs tend to be very difficult while G-T mispairs tend to be the most frequent mispairs made by polymerases.

Figure 4:
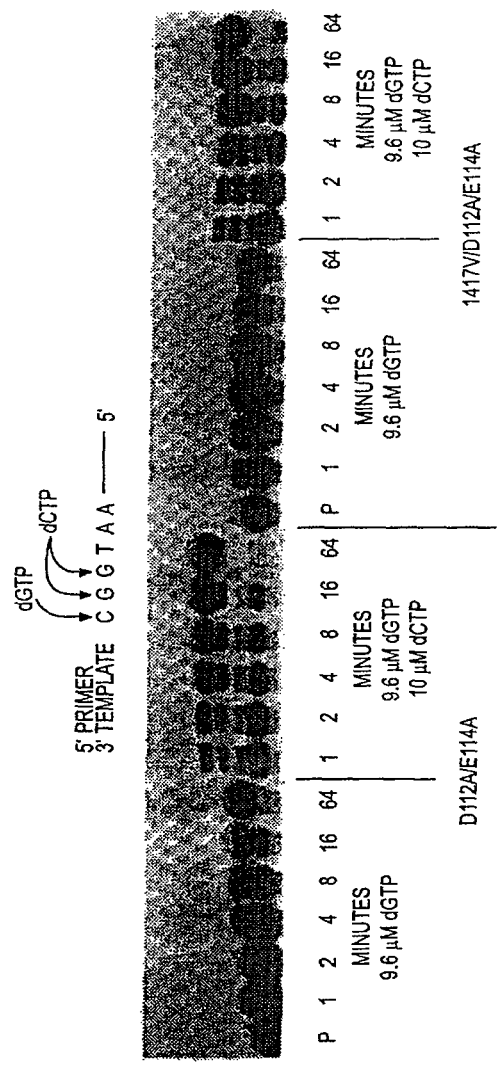
FIG. 4 is an electrophoretic gel showing a time course for primer extension assays catalyzed by T4 DNA polymerase mutants.

Time courses for primer extension reactions by both mutant T4 polymerases are shown in FIG. 4. Low concentrations of T4 polymerase relative to primer/template (p/t) were used so that incorporation reactions could be measured on convenient time scales (60 min). By 64 minutes 98% of the primers were extended. In reactions containing only dGTP, both polymerases nearly completely extended primer ends by dGMP without any detectable incorporation of dGMP opposite G. In reactions containing both dGMP and dCMP, both polymerases nearly completely extended primer ends by addition of one dGMP and two dCMP's. A small percentage (≈1%) of misincorporation was detectable in the reaction catalyzed by the D112A/E114Amutant. Significantly, no detectable misincorporation was seen in the reaction catalyzed by the I417V/D112A/E114A mutant.

Example 3

In accordance with the invention a fluorescent tag may be attached to the nucleotide base at a site other than the 3' position of the sugar moiety. Chemistries for such tags which do not interfere with the activity of the DNA polymerase have been developed as described by Goodwin et al. (1995, Experimental Technique of Physics 41:279-294). Generally the tag is attached to the base by a linker arm of sufficient length to move the bulky tag out of the active site of the enzyme during incorporation.

Figure 5:
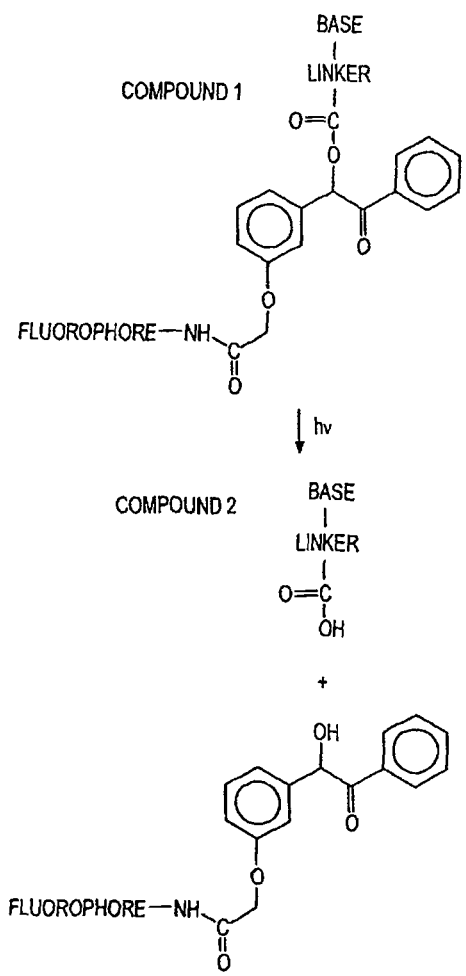
FIG. 5 is a schematic diagram illustrating a nucleotide attached to a fluorophore by a benzoin ester which is a photocleavable linker for use in the invention.

As illustrated in FIG. 5, a nucleotide can be connected to a fluorophore by a photocleavable linker, e.g., a benzoin ester. After the tagged dNMP is incorporated onto the 3' end of the DNA primer strand, the DNA template system is illuminated by light at a wave length corresponding to the absorption maximum of the fluorophore and the presence of the fluorophore is signaled by detection of fluorescence at the emission maximum of the fluorophore. Following detection of the fluorophore, the linker may be photocleaved to produce compound 2; the result is an elongated DNA molecule with a modified but non-fluorescent nucleotide attached. Many fluorophores, including for example, a dansyl group or acridine, etc., will be employed in the methodology illustrated by FIG. 5.

Alternatively, the DNA template system is not illuminated to stimulate fluorescence. Instead, the photocleavage reaction is carried out to produce compound 2 releasing the fluorophore, which is removed from the template system into a separate detection chamber. There the presence of the fluorophore is detected as before, by illumination at the absorption maximum of the fluorophore and detection of emission near the emission maximum of the fluorophore.

Example 4

Figure 6:
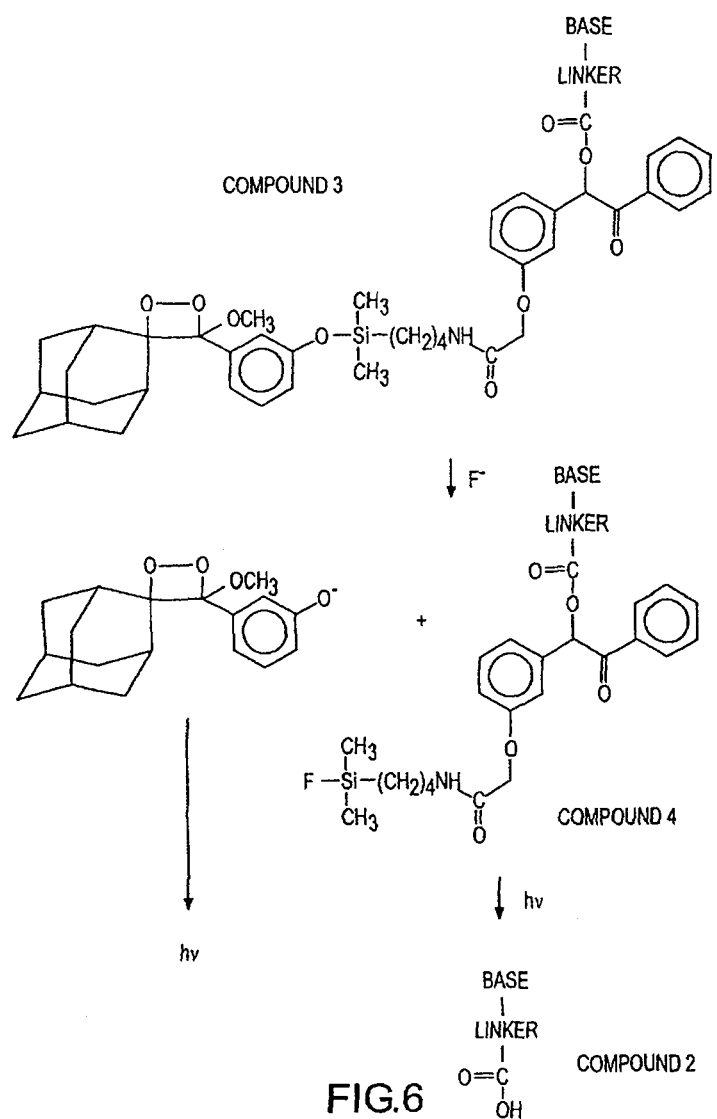
FIG. 6 is a schematic illustration of a nucleotide attached to a chemiluminescent tag for use in the invention.

In a specific embodiment of the invention, a linked system consisting of a chemiluminescently tagged dNTP can consist of a cherniluminescent group (the dioxetane portion of compound 4), a chemically cleavable linker (the silyl ether), and an optional photocleavable group (the benzoin ester) as depicted in FIG. 6. The cleavage of the silyl ether by a fluoride ion produces detectable chemiluminescence as described in Schaap, et al. (1991, "Chemical and Enzymatic Triggering of 1,2-dioxetanes: Structural Effects on Chemiluminescence Efficiency" in Bioluminescence & Chemiluminescence, Stanley, P. E. and Knicha, L. J. (Eds), Wiley, N.Y. 1991, pp. 103-106). In addition, the benzoin ester that links the nucleoside triphosphate to the silyl linker is photocleavable as set forth in Rock and Chan (1996, J. Org. Chem. 61: 1526-1529); and Felder, et al. (1997, First International Electronic Conference on Synthetic Organic Chemistry, September 1-30). Having both a chemiluminescent tag and a photocleavable linker is not always necessary; the silyl ether can be attached directly to the nucleotide base and the chemiluminescent tag is destroyed as it is read.

As illustrated in FIG. 6 with respect to compound 3, treatment with fluoride ion liberates the phenolate ion of the adamantyl dioxetane, which is known to chemiluminesce with high efficiency (Bronstein et al., 1991, "Novel Chemiluminescent Adamantyl 1,2-dioxetane Enzyme Substrates," in Bioluminescence & Chemiluminescence, Stanley, R E. and Kricka, R. J. (eds), Wiley, N.Y. 1991 pp. 73-82). The other product of the reaction is compound 4, which is no longer chemiluminescent. Compound 4 upon photolysis at 308-366 nm liberates compound 2.

The synthesis of compound 1 is achieved by attachment of the fluorophore to the carboxyl group of the benzoin, whose a-keto hydroxyl group is protected by 9(FMOC), followed by removal of the FMOC protecting group and coupling to the nucleotide bearing an activated carbonic acid derivative at its 3' end. Compound 4 is prepared via coupling of the vinyl ether form of the adamantyl phenol, to chloro (3-cyanopropyl)dimethylsilane, reduction of the cyano group to the amine, generation of the oxetane, and coupling of this chemiluminescence precursor to the nucleotide bearing an activated carbonic acid derivative at its 3' end.

Figure 7:
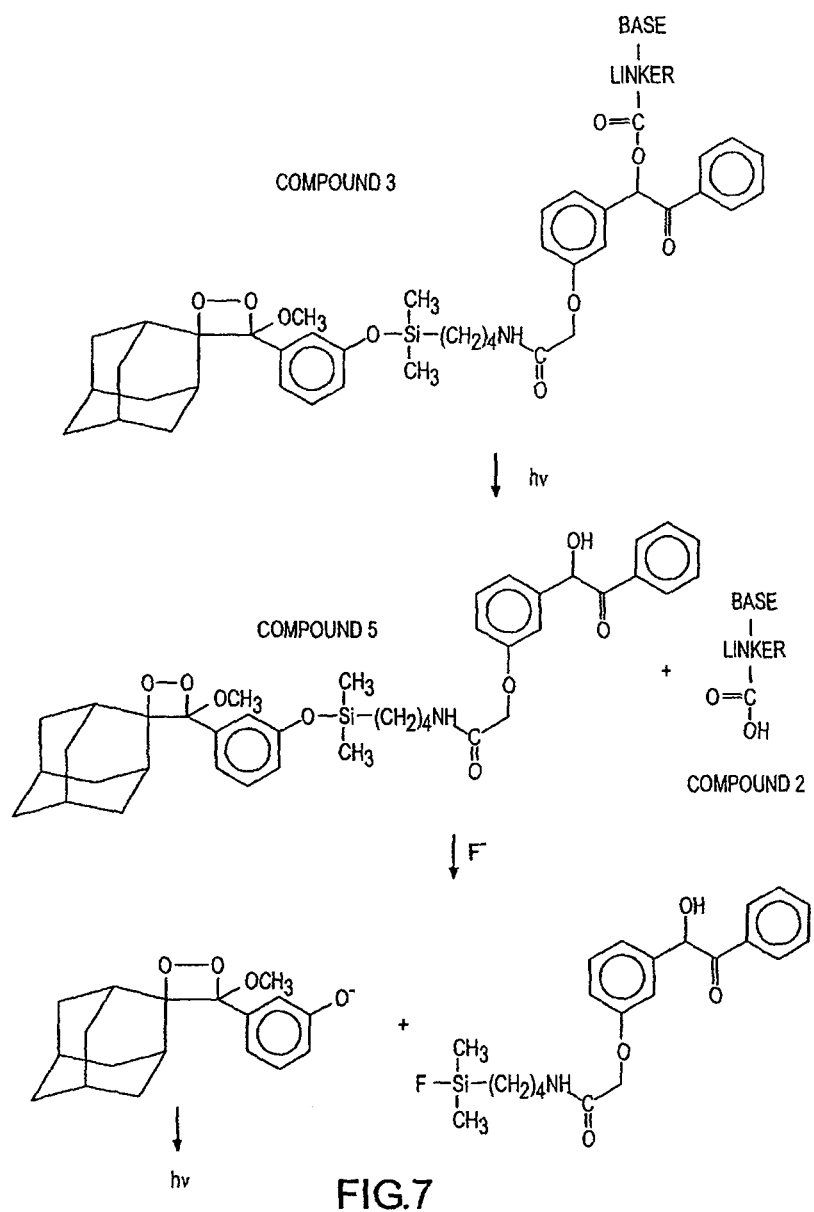
FIG. 7 is a schematic diagram of a nucleotide attached to a chemiluminescent tag by a cleavable linkage.

The chemiluminescent tag can also be attached to the dNTP by a cleavable linkage and cleaved prior to detection of chemiluminescence. As shown in FIG. 7, the benzoin ester linkage in compound 3 may be cleaved photolytically to produce the free chemiluminescent compound 5. Reaction of compound 5 with fluoride ion to generate chemiluminescence may then be carried out after compound 5 has been flushed away from the DNA template primer in the reaction chamber. As an alternative to photolytic cleavage, the tag may be attached by a chemically cleavable linker which is cleaved by chemical processing which does not trigger the chemiluminescent reaction.

Example 5

In this example, the nucleotide sequence of a template molecule comprising a portion of DNA of unknown sequence is determined. The DNA of unknown sequence is cloned into a single stranded vector such as M13. A primer that is complementary to a single stranded region of the vector immediately upstream of the foreign DNA is annealed to the vector and used to prime synthesis in reactive sequencing. For the annealing reaction, equal molar ratios of primer and template (calculated based on the approximation that one base contributes 330 g/mol to the molecular weight of a DNA polymer) is mixed in a buffer consisting of 67 mM TrisHCl pH 8.8, 16.7 mM $(NH_4)_2SO_4$ and 0.5 mM EDTA. This buffer is suitable both for annealing DNA and subsequent polymerase extension reactions. Annealing is accomplished by heating the DNA sample in buffer to 80° C. and allowing it to slowly cool to room temperature. Samples are briefly spun in a microcentrifuge to remove condensation from the lid and walls of the tube. To the DNA is added 0.2 mol equivalents of T4 polymerase mutant I417V/D112NE114A and buffer components so that the final reaction cell contains 67 mM TrisHCl pH 8.8, 16.7 mM $(NH_4)_2SO_4$, 6.7 mM $MgCl_2$ and 0.5 mM dithiothreitol. The polymerase is then queried with one dNTP at a time at a final concentration of 10 ÿM. The nucleotide is incubated with polymerase at 37° C. for 10 s. Incorporation of dNTPs may be detected by one of the methods described above including measuring fluorescence, chemiluminescence or temperature change. The reaction cycle will be repeated with each of the four dNTPs until the complete sequence of the DNA molecule has been determined.

Example 6

FIG. 7 illustrates a mechanical fluorescent sequencing method in accordance with the invention. A DNA template and primer are captured onto beads 18 using, for example, avidin-biotin or —$NH_2$/n hydroxysuccinimide chemistry and loaded behind a porous frit or filter 20 at the tip of a micropipette 22 or other aspiration device as shown in FIG. 7(a), step 1. Exonuclease deficient polymerase enzyme is added and the pipette tip is lowered into a small reservoir 24 containing a solution of fluorescently-labeled dNTP. As illustrated in step 2 of FIG. 7(a), a small quantity of dNTP solution is aspirated through the filter and allowed to react with the immobilized DNA. The dNTP solution also contains approximately 100 nM polymerase enzyme, sufficient to replenish rinsing losses. After reaction, as shown in step 3, the excess dNTP solution 24 is forced back out through the frit 20 into the dNTP reservoir 24. In step 4 of the process the pipette is moved to a reservoir containing buffer solution and several aliquots of buffer solution are aspirated through the frit to rinse excess unbound dNTP from the beads. The buffer inside the pipette is then forced out and discarded to waste 26. The pipette is moved to a second buffer reservoir (buffer 2), containing the chemicals required to cleave the fluorescent tag from the incorporated dNMP. The reaction is allowed to occur to cleave the tag. As shown in step 5 the bead/buffer slurry with the detached fluorescent tag in solution is irradiated by a laser or light source 28 at a wavelength chosen to excite the fluorescent tag, the fluorescence is detected by fluorescence detector 30 and quantified if incorporation has occurred.

Subsequent steps depend on the enzyme strategy used. If a single-stage strategy with an exonuclease-deficient polymerase is used, as illustrated in FIG. 7(b), the solution containing the detached fluorescent tag is discarded to waste (step 6) which is expelled, followed by a further rinse step with buffer 1 (step 7) which is thereafter discarded (step 8) and the pipette is moved to a second reservoir containing a different dNTP (step 9) and the process repeats starting from step 3, cycling through all four dNTPs.

Figure 8A:
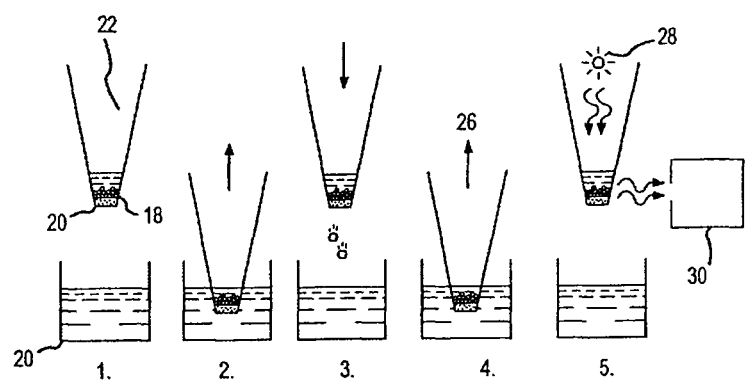
FIGS. 8(a) and 8(b) are schematic diagrams of a mechanical fluorescent sequencing method in accordance with the invention in which a DNA template and primer are absorbed on beads captured behind a porous frit.
Figure 8B:
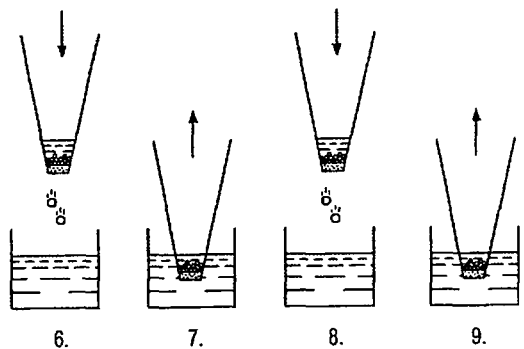
Figure 9:
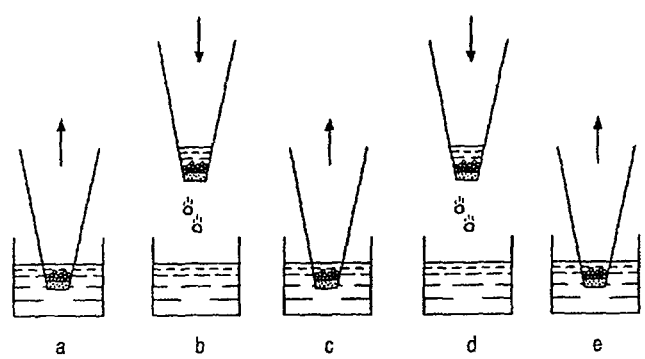
FIG. 9 is a schematic diagram of a sequencing method in accordance with the invention utilizing a two cycle system.

In a two-stage strategy, after the correct dNTP has been identified and the repeat length quantified in step 5, the reaction mixture is rinsed as shown in steps 6, 7, and 8 of FIG. 7(b) and the pipette is returned to a different reservoir containing the same dNTP (e.g., dentil) as shown in step (a) of FIG. 8 to which a quantity of exonuclease-proficient polymerase has been added and the solution is aspirated for a further stage of reaction which proof-reads the prior extension and correctly completes the extension. This second batch of dNTP need not be fluorescently tagged, as the identity of the dNTP is known and no sequence information will be gained in this proof-reading step. If a tagged dNTP is used, the fluorescent tag is preferably cleaved and discarded as in step 5 of FIG. 7(a) using Buffer 2. Alternatively, the initial incorporation reaction shown in step 2 of FIG. 7(a) is carried out for long enough, and the initial polymerase is accurate enough, so that the additional amount of fluorescent tag incorporated with dNTP1 at step a of FIG. 8 is small and does not interfere with quantification of the subsequent dNTP. Following proof-reading in step a of FIG. 8, excess dNTP is expelled (step b) and the reaction mixture is rinsed (steps c, d) with a high-salt buffer to dissociate the exo+polymerase from the DNA primer/template. It is important not to have exonuclease-proficient enzyme present if the DNA primer/template is exposed to an incorrect dNTP. The pipette is then moved to step e, in which the reservoir contains a different dNTP, and the process is repeated, again cycling through all four dNTPs.

Example 7

A new process for destruction of a fluorophore signal which involves reaction of the electronically excited fluorophore with an electron-abstracting species, such as diphenyliodonium salts, is described.

Figure 10:
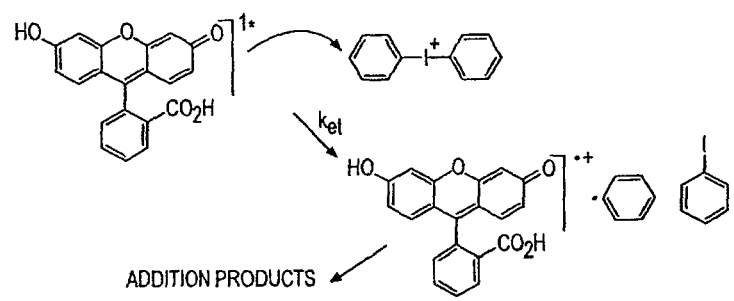
FIG. 10 is a diagram of the mechanism of photochemical degradation of fluorescein by diphenyliodonium ion (DPI).

The reaction of a diphenyliodonium ion with an electronically excited fluorescein molecule is illustrated in FIG. 10. The diphenyliodonium ion extracts an electron from the excited state of the fluorescein molecule producing a radical ion of the fluorescein molecule and a neutral diphenyliodonium free radical. The diphenyliodonium free radical rapidly decomposes to iodobenzene and a phenyl radical. The fluorescein radical ion then either reacts with the phenyl radical or undergoes an internal arrangement to produce a final product which is no longer fluorescent.

Figure 11:
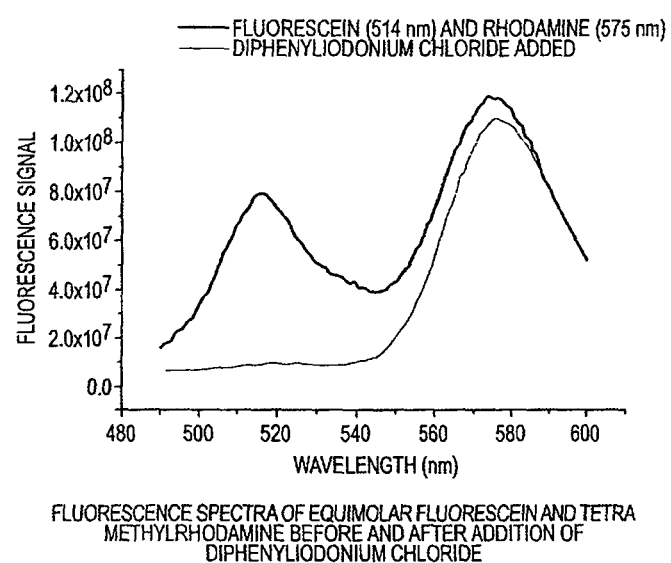
FIG. 11 shows fluorescence spectra of equimolar concentrations of fluorescein and tetramethylrhodamine dyes before and after addition of a solution of diphenyliodonium chloride.
Figure 12:
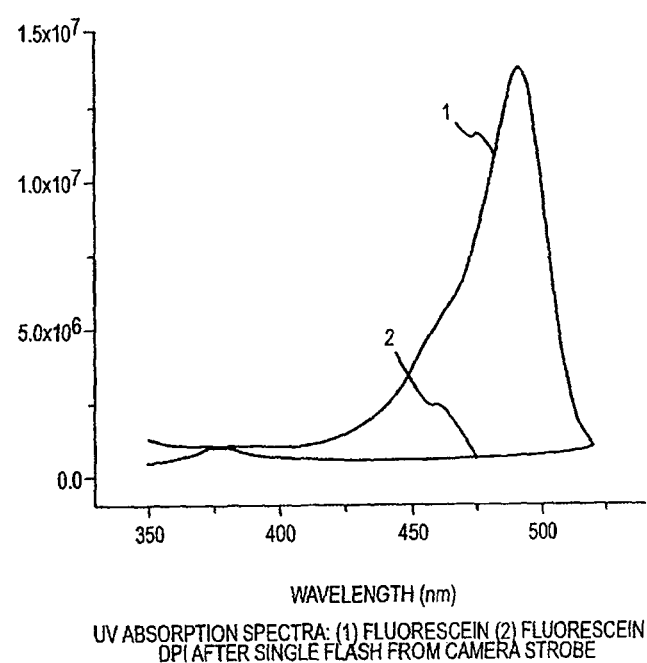
FIG. 12 is the UV absorption spectra obtained from (1) fluorescein and (2) fluorescein+DPI after a single flash from a xenon camera strobe.

FIGS. 11 and 12 demonstrate evidence for the specific destruction of fluorescein by diphenylionium ion. In FIG. 11, fluorescence spectra are presented for a mixture of fluorescein and tetramethylrhodamine dyes, before and after addition of a solution of diphenyliodonium chloride. It is seen that the fluorescence from the fluorescein dye is immediately quenched, demonstrating electron abstraction from the excited state of the molecule while the fluorescence from the rhodamine is unaffected, apart from a small decrease due to the dilution of the dye solution by the added diphenyliodonium chloride solution.

Elimination of the fluorescent signal from the fluorescein dye by diphenyliodonium chloride is not in itself proof that the fluorescein molecule has been destroyed, because electron abstraction from the excited state of fluorescein effectively quenches the fluorescence, and quenching need not result in destruction of the fluorescein molecule. However, FIG. 12 demonstrates that the fluorescein molecule is destroyed by reaction with the diphenyliodonium and not simply quenched. FIG. 12 demonstrates the ultraviolet (UV) absorption spectra for a fluorescein solution before and after addition of a solution of diphenyliodonium chloride. Spectrum 1 is the UV absorption spectrum of a pure fluorescein solution. Spectrum 2 is the UV absorption of the fluorescein solution following the addition of a solution containing a molar excess of diphenyliodonium (DPI) chloride and exposure to a single flash from a xenon camera strobe. The data show that fluorescein is essentially destroyed by the photochemical reaction with the DPI ion. FIG. 12 provides clear evidence that diphenyliodonium chloride not only quenches the fluorescence from the fluorescein dye but destroys the molecule to such an extent that it can no longer act as a fluorophore.

An experiment was performed to demonstrate efficient fluorescent detection and destruction of fluorophore using a template sequence. The template, synthesized with a alkylamino linker at the 5' terminus, was:

3'-H$_2$N—(CH$_2$)$_7$-GAC CAT TAT AGG TCT TGT
TAG GGA AAG GAA GA-5' (SEQ ID NO: 2)

The trial sequence to be determined is: G GGA AAG GAA GA (SEQ ID NO: 3).

A tetramethyrhodamine-labeled primer sequence was synthesized to be complementary to the template as follows:

5'-[Rhodamine]-(CH$_2$)$_6$-CTG GTA ATA TCC AGA
ACA AT-3' (SEQ ID NO: 4)

The alkyl amino-terminated template molecules were chemically linked to Sepharose beads derivatized with N-hydroxysuccinimide and the rhodamine-labeled primer was annealed to the template. The beads with attached DNA template and annealed primer were loaded behind a B-100 disposable filter in a 5-ml syringe. A volume containing a mixture of fluorescein-labeled and unlabelled dCTP in a ratio of 1:2 and exonuclease-deficient polymerase enzyme in a reaction buffer as specified by the manufacturer was drawn into the syringe. Reaction was allowed to proceed for 20 minutes, at 35° C. After the reaction, the fluid was forced out of the syringe, retaining the beads with the reacted DNA behind the filter, and three washes with double-distilled water were performed by drawing water through the filter into the syringe and expelling it. The beads were resuspended in phosphate buffer, the filter was removed and the suspension was dispensed into a cuvette for fluorescence analysis. Following fluorescence analysis, the bead suspension was loaded back into the syringe which was then fitted with a filter tip, and the phosphate buffer was dispensed. A solution of DPI was drawn up into the syringe with a concentration calculated to be in 1:1 molar equivalence to the theoretical amount of DNA template, the filter was removed and the bead suspension was dispensed into a cuvette for UV light exposure for 15 minutes. The suspension was recollected into a syringe, the filter was reattached, the DPI solution was expelled, and the beads were resuspended by drawing up 0.7 mL of phosphate buffer. After removal of the filter the bead suspension was dispensed into a clean cuvette for fluorescence analysis to check the completeness of destruction of the fluorescein by the reaction with the DPI. A subsequent polymerase reaction was performed using the same protocol with labeled dTTP and similarly measured for fluorescence.

Figure 13:
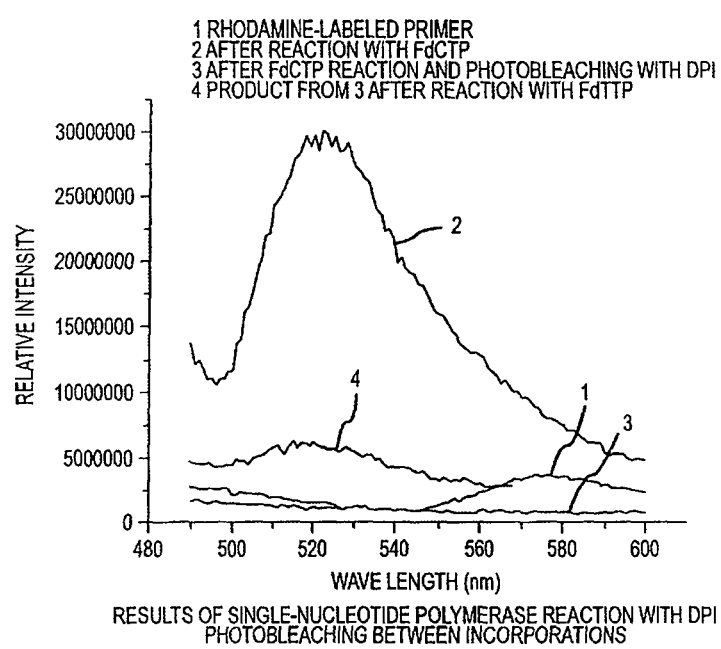
FIG. 13 displays the fluorescence spectra from single nucleotide polymerase reactions with DPI photobleaching between incorporation reactions.

FIG. 13 demonstrates the results of the polymerase reactions, with photochemical destruction of the fluorescein label by DPI following each nucleotide incorporation reaction. Curve 1 shows rhodamine fluorescence following annealing of the rhodamine labeled primer to the beads, demonstrating covalent attachment of the template strands to the beads and capture of the rhodamine-labeled primer strands. Curve 2 demonstrates detection of fluorescein following polymerase-catalyzed incorporation of three partially fluorescein-labeled dCMPs onto the 3' terminus of the primer strands. Curve 3 shows complete destruction of the incorporated fluorescein label by photo-induced reaction with diphenyliodonium chloride. Loss of rhodamine signal here is attributed to loss of a significant fraction of the beads which stuck to the filter during washes. Curve 4 shows detection of a new fluorescein label following photochemical destruction of the fluorescein attached to the dCMP's and subsequent polymerase-catalyzed incorporation of three partially fluorescein-labeled dTMPs onto the 3' terminus of the primer strands.

The following methods were utilized to demonstrate successful destruction of a fluorescein-labeled dTMP.

Sepharose beads were purchased from Amersham with surfaces derivatized with N-hydroxysuccinimide for reaction with primary amine groups. The alkyl amino-terminated templates were chemically linked to the Sepharose beads using the standard procedure recommended by the manufacturer.

The beads with attached template were suspended in 250 mM Tris buffer containing 250 mM NaCl and 40 nM $MgCl_2$. The solution containing the primer strands was added and the mixture heated to 80° C. and cooled over ~2 hours to anneal the primers to the surface-immobilized DNA template strands.

Fluorescein-labeled dUTP and dCTP were purchased from NEN Life Science Products. Unlabeled dTTP and dCTP were purchased from Amersham.

Prior to any reaction, the annealed primer/template was subjected to fluorescence analysis to ensure that annealing had occurred. The excitation wavelength used was 320 nm and fluorescence from fluorescein and rhodamine was detected at ~520 nm and ~580 nm respectively.

Reagent volumes were calculated on the assumption that the DNA template was attached to the beads with 100% efficiency.

The 5× reaction buffer contained:

| | |
|---|---|
| 1) | 250 mM Tris buffer, pH 7.5 |
| 2) | 250 mM NaCl |
| 3) | 40 mM $MgCl_2$ |
| 4) | 1 mg/mL BSA |
| 5) | 25 mM dithiothreitol (DTT) |
| — | mixed and brought to volume with double- |

T4 DNA polymerase was obtained from Worthington Biochemical Corp. The polymerase was dissolved in the polymerase buffer according to the manufacturer's protocols.

Fluorescein-labeled and unlabeled dCTP's were mixed in a ratio of 1:2.

The reaction was run in a 5 mL syringe (Becton Dickinson) fitted with a B-10 (Upchurch Scientific). This limits the reaction volume to 5 mL total:

| | |
|---|---|
| Primer template suspension | 0.7 mL |
| T4 DNA Polymerase | 1.0 mL |
| FdCTP/dCTP | 0.040 mL |
| 5X reaction buffer | 2.0 mL |
| double-dist. $H_2O$ | 1.0 mL |

The reaction was allowed to proceed in a 35° C. oven for 20 minutes. Following reaction, the fluid was forced out of the syringe allowing the filter to retain the beads with the reacted DNA. Three washes with double-distilled water were performed. All waste was collected and saved for future reuse. The beads were resuspended in 0.7 mL of phosphate buffer, the filter was removed and the suspension was dispensed into a cuvette for fluorescence analysis.

Following fluorescence analysis the bead suspension was collected into a 1 mL syringe (Becton Dickinson) which was then fitted with a filter tip. The phosphate buffer was dispensed and the waste collected. A solution of diphenyliodonium chloride (DPI) was drawn up with a concentration calculated to be in 1:1 molar equivalence to the theoretical amount of DNA template (i.e. DPI was present in excess of the incorporated fluorescein-labeled dCTP). The filter was removed and the bead suspension with added DPI was dispensed into a cuvette and exposed to UV light for 15 minutes. The suspension was recollected into a syringe, the filter reattached, the DPI solution was dispensed and the beads were resuspended in 0.7 mL of phosphate buffer. The bead suspension was dispensed into a clean cuvette for fluorescence analysis.

It should be noted that a significant fraction of the beads used in this procedure appeared to become stuck in the filter on the syringe. This resulted in a significant increase in the pressure needed to force fluids through the filter as it became clogged by the beads, and more importantly reduced the amount of DNA available for fluorescent detection of incorporated nucleotides and reduced the weak rhodamine signal from the labeled primer to the point where it was no longer detectable.

Following the successful incorporation reaction with dCTP, a subsequent polymerase reaction was run to incorporate dTTP. The incorporated fluorescein-labeled dTMP was detected, but with significantly lower intensity due to the losses of the beads in the filter in the multiple transfer steps between the reaction syringe and the analysis cuvette. The lowered signal could also result in part from a different labeling efficiency of the dTTP and a different incorporation efficiency for the labeled nucleotide in the polymerase reaction. Because the rhodamine signal was no longer detectable following the second incorporation reaction it was not possible to correct for bead losses.

The results are shown in FIG. 13. The data represented by the curves were obtained sequentially as follows:

Curve 1 shows the rhodamine fluorescence following annealing of the rhodamine-labeled primer to the bead-immobilized DNA template.

Curve 2 demonstrates detection of the fluorescein-labeled dCTP following polymerase-catalyzed incorporation of three dCMP's onto the 3' terminus of the primer strands.

Curve 3 demonstrates complete destruction of the incorporated fluorescein label on the dCMP's by photo-induced reaction with dipenyliodonium chloride. In this instance, the rhodamine label also has vanished; this is primarily because a significant fraction of the beads were lost by sticking in the filter used in the reagent flushing operation. It is possible that the rhodamine also was destroyed by the DPI photochemical reaction.

Curve 4 demonstrates detection of a new fluorescein label following photochemical destruction of the fluorescein label on the dCMP's and polymerase-catalyzed incorporation of three fluorescein-tagged dTMP's onto the 3' terminus of the primer strands. The lower signal compared to curve 2 results mainly from the bead losses in the syringe, but may also reflect a lower incorporation efficiency of the dTMP and/or a lower labeling efficiency. Because the rhodamine signal from the labeled primer is no longer detectable, the bead losses cannot be calibrated.

The results shown here demonstrate the concept of reactive sequencing by fluorescent detection of DNA extension followed by photochemical destruction of the fluorophore, which allows further extension and detection of a subsequent added fluorophore. This cycle can be repeated a large number of times if sample losses are avoided. In practical applications of this approach, such losses will be avoided by attaching the primer or template strands to the fixed surface of an array device, for example a microscope slide, and transferring the entire array device between a reaction vessel and the fluorescent reader.

Example 8

Read length is defined as the maximum length of DNA sequence that can be read before uncertainties in the identities of the DNA bases exceed some defined level. In the reactive sequencing approach, read length is limited by two types of polymerase failures: misincorporation, i.e., incorrectly incorporating a noncomplementary base, and extension failure, i.e., failure to extend some fraction of the DNA primer strands on a given cycle in the presence of the correct complementary base. Example 2 demonstrated that reaction conditions can be optimized such that neither type of failure affects more than ~1% of the arrayed strands for any given incorporation reaction. Neither type of failure directly produces an error signal in the sequence readout, because neither a 1% positive signal, for a misincorporation, nor a 1% decrease in the signal for a correct incorporation, in the case of extension failure, will be significant compared to the signals anticipated for a correct incorporation. However, accumulated failures limit the read length in a variety of different ways.

For example, misincorporation inhibits any further extension on the affected strand resulting in a reduction in subsequent signals. It is estimated that the probability of continuing to extend a given strand following a misincorporation is no greater than 0.1%, so that any contribution to the fluorescent signal resulting from misincorporation followed by subsequent extension of the error strand will be negligible. Instead, the accumulation of misincorporations resulting in inhibition of strand extension ultimately reduces the overall signal amplitude for correct base incorporation to a level at which noise signals in the detection system begin to have a significant probability of producing a false signal that is read as a true base incorporation.

Extension failures typically arise due to the kinetics of the extension reaction and limitations on the amount of time allotted for each extension trial with the single deoxynucleotide triphosphates (dNTP's). When reaction is terminated by flushing away the dNTP supply, a small fraction of the primer strands may remain unextended. These strands on subsequent dNTP reaction cycles will continue to extend but will be out of phase with the majority strands, giving rise to small out-of-phase signals, i.e., signaling a positive incorporation for an added dNTP which is incorrect for extension of the majority strands. Because extension failure can occur, statistically, on any extension event, the out-of-phase signals will increase as the population of strands with extension failures grows. If reaction conditions are chosen so that the reaction is 99.9% complete on a given reaction cycle, for example, after a further number, N, of successful extension reactions, the out-of-phase signal will be approximately $(1-0.999^N)$. The number N at which the out-of-phase signal becomes large enough to be incorrectly read as a correct extension signal is the read length. For example, after extension by 200 bases with 99.9% completion, the out-of-phase signal is approximately 18% of the in-phase signal, for a single base extension in either case. After extension by 400 bases the out-of-phase signal grows to 33%. The point at which the read must terminate is dictated by the ability to distinguish the in-phase signals from the out-of-phase signals.

In what follows, a length of single base repeats, e.g. AAAAA, is treated as a single base for the purposes of discussing the phase difference between strands. If the reaction cycle of the four dNTP's is unchanged, then a primer strand which has failed to extend when the correct dNTP, for example dATP, is in the reaction cell cannot trail the leading, i.e., majority strands, which did extend correctly, by more than 3 bases because the fourth base in the dNTP reaction cycle will always once again be the correct base (dATP) for the strand which failed to extend previously. It is assumed that extension failure is purely statistical, and that any strand which fails to extend has an equal chance of subsequent extension when the correct dNTP is supplied, and that this extension probability is sufficiently high that the chance of repeated extension failures on the same strand is vanishingly small. For example, if the probability of extension failure on a single strand is 0.1%, the probability of two extension failures on the same strand is $(0.001)^2$ or $10^{-6}$. Similarly, the trailing strand can never resynchronize with the leading strands if extension subsequently proceeds correctly, because the leading strands will always have extended by at least one more nucleotide—G, T, or C in the example discussion of an A extension failure—before the trailing strand can add the missing A. The effect is that after each complete dNTP cycle the trailing strands always follow the leading strands by an extension amount that represents the bases added in one complete dNTP cycle at a given point in the sequence. These observations predict that: (i) the gap between the leading and trailing strands perpetually oscillates between 1 and 3 bases and can never increase unless a second extension failure occurs on the same strand; and (ii) the gap between the leading and trailing strands is independent of the position along the trailing strand at which the extension failure occurs. This gap at any given point in the extension of the leading strands is solely a function of the sequence of the leading strand population up to that point and the dNTP probe cycle. In other words, a population of trailing strands is produced due to random extension failure at different points in the sequence, but these trailing strands themselves are all exactly in phase with each other.

Because the result of an extension failure is to produce a trailing strand population that trails the leading strands perpetually by an amount that oscillates between one and three nucleotides, assuming that a second extension failure does not occur on the trailing strand and that the probing dNTP cycle remains unchanged, therefore the gap between the leading and trailing strand populations can always be known by tracking the leading strand sequence by, for example, computer simulation and simulating an extension failure event at any point along the sequence.

Thus the present invention provides, first, a general method of computer tracking of the sequence information which allows the out of-phase error signals due to extension of trailing strands to be recognized and subtracted from the correct signals, and, second, methods of altering the probing dNTP cycle to selectively extend the trailing strands so that they move back into phase with the leading strands, thus completely eliminating sequence uncertainty due to out of-phase signals arising from the trailing strands that result from extension failure.

The statistics which govern the ability to distinguish an incorrect signal from out-of-phase strands from a correct signal depend upon the noise level and statistical variation of the fluorescence signal. Assuming that the signal for a correct 1-base extension has a standard deviation of ±5%, then statistically 99.75% of the signals will have an amplitude between 0.85 and 1.15 (±3 standard deviations from the average value) when the average value is 1.0 and the standard deviation is 0.05. If the extension signal must be at least 85% of the average single extension signal to register a correct extension, then statistically a correct extension will be missed only 0.13% of the time, i.e. the readout accuracy would be 99.87%. Another 0.13% of the signals for a correct extension will be greater than 1.15, but the concern is only with signals that are lower than average and so are more difficult to distinguish from a growing signal from out-of-phase strands. The statistics for errors arising from out-of-phase extension of a trailing strand are similar. If the standard deviation of the trailing strand signals is also ±5% of the mean extension signal which will be true whenever the trailing strand intensity approaches the leading strand intensity, then if the trailing strand intensity does not grow beyond 0.7, the fraction of trailing strand extensions that give rise to a signal of 0.85 or greater 4 standard deviations beyond the mean is less than 0.01%. Thus an out-of phase signal arising from a single-base extension on one of the three sets of trailing strands should be distinguishable from the in-phase signal with accuracy so long as the out-of-phase signal does not grow beyond −70% of the in-phase signal.

The above discussion assumes that all the extension events correspond to single base extensions. However, multiple single-base repeats are common in DNA sequences, thus one must consider the situation where the out-of-phase signal can be M times larger than that for a single base extension, where M is the repeat number. For example, if the population of one of the three sets of out-of-phase strands has grown to 20% of the leading strand population, at which level the in-phase and out-of-phase signals can readily be distinguished for a single base extension, then if this set of out-of-phase strands encounters a 5-base repeat, e.g. AAAAA, the signal for that repeat becomes identical in magnitude to that for a single base extension on the in-phase strands. Real-time computer monitoring of the extension signals permits discrimination against such repeat-enhanced out-of-phase signals, for example, by implementing linear and/or nonlinear auto-regressive moving average (ARMA) schemes. The essential points here are as follows (i) the out-of-phase strands are those that are trailing the majority strands as a result of extension failure; misincorporation events which could produce leading error strands have the effect of shutting down further extension on the affected strands and so do not give rise to significant out-of-phase error signals; (ii) there is always only one population of trailing strands regardless of where the extension failure occurred; all the primer strands in this population have been extended to the same point which trails the leading strand sequence by 1, 2 or 3 bases; and (iii) because the leading strands have always previously traversed the sequence subsequently encountered by the trailing strands, the sequence at least 1 base beyond the 3' terminus of the trailing strands is always known and allows prediction of exactly whether, and by how much, these trailing strands will extend for any nucleotide supplied, by simulating, in a computer for example, the effect of an extension failure at any point in the known sequence upstream of the position to which the leading strands have advanced.

On each incorporation trial, in addition to any possible correct extension signal for the leading strands, there may also be an error signal corresponding to extension of the trailing strands. For example, let us assume that the trailing strand population has grown as large as 20% of the leading strand population. The size of this population can be monitored by detecting the incorporation signal when the trailing strands extend and the leading strands do not. Assume that the leading strand population has just traversed a single base repeat region on the template, for example AAAAA, and incorporated onto the primer the complementary T repeat: TTTTT. The trailing strands will not traverse this same AAAAA repeat for at least a complete cycle of the four probing nucleotides, until the next time the strands are probed with dTTP. Knowing the size of the trailing strand population from the amplitude of its incorporation signals, determined at any point where the leading strands do not extend but the trailing strands do, the signal to be expected from the trailing strand population due to the TTTTT incorporation can be calculated precisely. If the trailing strand population is ⅕ as large as the leading strand population, for example, this signal will mimic incorporation of a single T on the leading strand population. In the absence of the computer-aided monitoring method discussed here, such a false signal would give rise to a drastic sequence error.

Figure 14A:
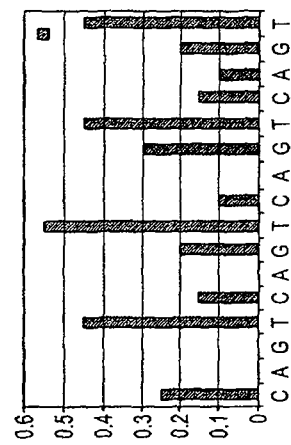
FIG. 14A-D. Simulation of Reactive Sequencing of [CTGA] GAA ACC AGA AAG TCC [T] (SEQ ID NO: 1), probed with a dNTP cycle. 14A. Sequence readout close to the primer where no extension failure has occurred. 14B. Sequence readout downstream of primer where 60% of the strands have undergone extension failure and are producing out of phase signals and misincorporation has prevented extension on 75% of all strands. 14C. Downstream readout with error signals from trailing strands (dark shading) distinguished from correct readout signals from leading strands (light shading) using knowledge of the downstream sequence of the trailing strands. 14D. Corrected sequence readout following subtraction of error signals from trailing strands. Note the similarity to the data of FIG. 1A.
Figure 14C:
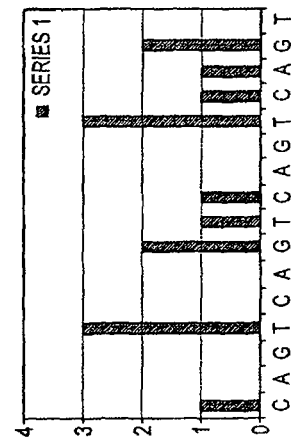
Figure 14B:
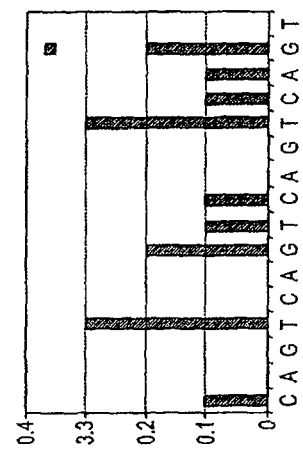
Figure 14D:

FIGS. 14A and 14B demonstrate how data would appear for a sequence: [CTGA] GAA ACC AGA AAG TCC [T] (SEQ ID NO: 1), probed with a dNTP cycle: CAGT, close to the primer where no extension failure has occurred (FIG. 14A) and well downstream (FIG. 14B) at a point where 60% of the strands have undergone extension failure and are producing out-of-phase signals, and misincorporation has shut down extension on 75% of all strands. The readouts shown start at the second G in the sequence (beyond the [CTGA] sequence in parentheses) and end at the last C (before the [T] in parentheses). The digital nature of the signal in FIG. 14A and also the amplitude scale should be noted. In FIG. 14B, the signal for a single base extension has been reduced by 60%, from 1.0 to 0.4 due to the extension failure strands, and by a further factor of 4 to 0.1 due to misincorporation and the resulting 75% signal loss. However, added to the correct extension signals are signals due to the out-of-phase extension of the trailing strands. At first sight, the readout is completely different from the correct readout shown in FIG. 14A, due to the superposition of signals produced when the trailing strands encounter the sequence previously traversed by the leading strands. Particularly large errors arise whenever the trailing strand population encounters the AAA repeats. For example, the second T probe yields a signal amplitude corresponding to an AAAAA repeat instead of the correct single A, the third G probe gives a signal corresponding to CCC when in fact there is no C at this point in the leading strand sequence, the fourth T probe reads 4 A's when the correct sequence has none (the trailing strands encounter the second AAA repeat). However, because the sequence from the leading strands is known, the false signals arising from the trailing strands can be predicted and subtracted from the total signal to obtain the correct sequence readout. This is shown in FIG. 14C, where the signals arising from the trailing strands are coded by different shading from the leading strand signal. Because the signals due to the trailing strands can be predicted, the error signals can be subtracted to obtain the correct digital sequence readout shown in FIG. 14D. It should be noted that the data in FIG. 14D are now identical to those in FIG. 14A, and yield the correct sequence readout for the leading strands, the only difference being that the overall intensity is reduced due to the assumed loss of signal due to misincorporation and extension failure, the latter populating the trailing strands. In other words, by keeping track of the sequence in a computer the effect is as though one could directly visualize the different contributions as depicted on the plot in FIG. 14C. Therefore, it is possible to predict for any probe nucleotide event exactly what the signal from the trailing strand population should be, and subtract this error signal from the measured signal to arrive at a true digital signal representative of the sequence of the leading strand population, which is the desired result.

Given the ability to compute and subtract any trailing strand signals as discussed, the accuracy with which nucleotide incorporation or non-incorporation on the leading strands can be sensed is limited, not by the absolute size of the trailing strand signal, but instead by the noise on those signals. For example, assume that the signal for a single-base extension of a trailing strand population equal to 20% of the leading strand population is 0.2±0.05. If the trailing strands encounter a 5-base repeat, the resulting signal would be identical in amplitude to that produced by a single-base extension of the leading strands, but this signal could be subtracted from the observed signal to yield either a signal resulting from a leading strand extension, or a null signal corresponding to no extension of the leading strands. Assuming that the noise is purely statistical and therefore is reduced in proportion to the square root of the signal amplitude, for a 5-base extension of the trailing strands or a single extension of the leading strands the signal would be 1±(0.05×45), i.e. 1±0.11, because the statistical noise on a set of added signals grows as the square root of the number of signals. One can subtract from this value a correction signal which is much more accurately known because the trailing strand signal has been repeatedly measured yielding better statistics on this value. It is assumed that the uncertainty in the correction signal is negligible. For no extension of the leading strands, the resulting difference signal would be 0±0.11, whereas a single extension of the leading strands would yield a difference signal of 1±0.11; the two signals are distinguishable with better than 99.9% accuracy.

The example given here is an extreme case: in fact, the extension failure can be corrected at any point, so that it will be possible to minimize the trailing strand population below a level where it would produce signals that make the leading strand sequence uncertain.

There are additional advantages to the computer-aided monitoring method proposed. First, the signals from the trailing strands serve as an additional check on the leading strand sequence. Second, the trailing strand population could be allowed to surpass the leading strand population in magnitude. Without computer-aided monitoring, readout would have to cease well before this point, however, with computer-aided monitoring, readout can continue, now using the trailing strands rather than the leading strands to reveal the sequence. Thus, the strand population that trails due to only one extension failure now becomes the leading strand population for the purposes of computer aided monitoring. This allows readout to continue until further complications arise from the occurrence of 2 extension failures on the same strand, producing a new trailing strand population which can be tracked in the same way as the single failure strands, while the population of strands that have undergone no error failure diminishes to the point where it contributes no detectable signal.

Optimization of reagents, enzyme and reaction conditions should allow misincorporation probabilities below 1%, and extension failure probabilities as low as 0.1%. The computer aided monitoring method of the present invention additionally provides a means for healing the trailing strand population by selectively extending this population so that it is again synchronous with the leading strands. For example, given a dNTP probe cycle of GCTA, and a template sequence (beyond the 3' end of the primer) of:

```
                                     (SEQ ID NO: 5)
     ......GTGCAGATCTG ...
``` and assuming that when dCTP is in the reaction chamber, the polymerase fails to incorporate a C in some fraction of the primer strands, the following results:

```
                                     (SEQ ID NO: 5)
     Template           ......GTG CAG ATC TG ...

Main strands       ......C (SEQ ID NO: 5)
     Template           ......GTG CAG ATC TG Failure strands    ......
```

At the end of the first cycle, the main strands have extended by . . . CA, while the failure strand has not advanced. After one more complete cycle, the main strand extension is . . . CAC and the failure strand now reads . . . CA, i.e. now just one base out of phase.

```
                                     (SEQ ID NO: 5)
     Template           ......GTG CAG ATC TG ...

Main strands       ......CAC (SEQ ID NO: 5)
     Template           ......GTG CAG ATC TG Failure strands    ......CA
```

Because the phase lag arises from the repeating interaction of the probe cycle sequence with the template sequence, the unchanged probe cycle can never have the correct sequence to resynchronize the strands. Instead, if the probe cycle is unchanged, and if no further extension failures occur, the phase lag for a given failure strand oscillates perpetually between 1 and 3 bases, counting single base repeats as one base for this purpose. However because the leading strand sequence up to the last extension is always known, one can determine the effect of introducing an extension failure at some upstream position. It should be noted that an extension failure introduced at any arbitrary upstream position, or any base type, always produces the same phase lag because the effect of an extension failure is to cause extension of the affected strand to lag by one complete dNTP cycle. Thus, it is possible to alter the probe cycle sequence, for example to probe with a C, instead of a G, after the last A in the sequence discussed above. The failure strand would advance while the main strands did not and the phase lag would heal. In yet another embodiment the dNTP probe cycle may be reversed whenever the phase lag shrinks to only 1 base. Whenever the phase difference declines to a single base, or repeats of a single base, then simply reversing the probe cycle sequence always resynchronizes the strands.

FIG. 15 shows how a leading strand population arising from incorrect extension of a fraction of primer strands due to nucleotide impurities can adversely affect the signals from the main population. Using the same template sequence as before: [CTGA] GAA ACC AGA AA GTC C [TC AGT] (SEQ ID NO: 6) and the same probe cycle: CAGT, the effect of a leading strand population which is 20% of the main strand population can be simulated and 2 bases ahead of the main strands at the time the main strand sequence begins to be read. The leading strands have already extended by -C TTT. The first C probe extends the main primer strands by one base complementary to the first G in the sequence giving a single base extension signal of 1. The first G extends the leading strands by -GG- complementary to the -CC- repeat, giving a signal of 0.4. Greater ambiguity arises when the leading strands encounter the second AAA-repeat at the second T probe, increasing the main strand signal from the correct value for a single base extension to 1.6. In the absence of further information, this value will be ambiguous or may be interpreted as a 2-base repeat.

Correction for these ambiguities comes from the fact that the correct sequence of the main strands is read following the leading strand read. In general, a large multiple repeat which can give an error signal when encountered by the leading strands will subsequently give a larger signal when encountered by the main strands, and superimposed on this correct signal will be a leading strand signal for which there are three possibilities: (i) zero signal: the leading strands do not extend; (ii) small signal that does not create ambiguity— the leading strands extend by a single base or a repeat number small enough not to simulate an additional base extension of the main strands; (iii) large signal; the leading strands encounter a second large repeat. By monitoring the main strand sequence, it is possible at each extension to retroactively estimate the effects of a leading strand population and subtract such signals from the main strand signals to arrive at a correct sequence. In the case where the leading strands encounter a repeat large enough to create ambiguity in the sequence, even if the leading strands subsequently encounter a second or third large repeat when the main strands encounter the first repeat, the main strands will eventually traverse the same region to give sufficient information to derive the correct sequence. In other words, the sequence information at any point is always overdetermined—the signal for any given extension is always read twice, by the leading strands and the main strands, and so yields sufficient information to determine both the correct sequence and the fractional population of the leading strands, which are the two pieces of information required.

Because the sequence of the leading strand population produced by impure nucleotides cannot be known until it is subsequently traversed by the main strands, one cannot know what dNTP probe cycle would act to extend the main strands while not extending the leading strands, as was the case for a trailing strand population produced by extension failure. However, as with trailing strands, the gap between the leading and main strands oscillates perpetually between one and three bases, and can be reconnected by reversing the dNTP probe sequence whenever the gap between the leading and main strands shrinks to a single base. Although it cannot be known when this single base gap occurs, the dNTP probe sequence can be reversed at regular intervals. Trials indicate that such a process ultimately reconnects approximately $2/3$ of the leading strands. The statistics for this process are as follows.

Statistically, because the gap between the main and leading strands can be there is a $1/3$ probability that the leading strand population will have only a 1. any time the cycle is reversed. The 1-base phase difference will always be h reversal. Another $1/3$ of the time the leading strands are 2 bases ahead at th reversed. For the next probing base the following possibilities exist:

| Lead strand | Main strand | |
|---|---|---|
| 0 | 0 | No extension on either strand: Prob. $3/4 \times 3/4 = 9/16$ |
| +1 | 0 | Phase lag increases: Prob. $1/4 \times 3/4 = 3/12$ |
| +1 | 0 | Both strands advance: Prob. $1/4 \times 1/4 = 1/16$ |
| 0 | +1 | Phase lag decreases: Prob. $3/4 \times 1/4 = 3/12$ |

Phase lag stays at 2: Number of chances = $10/16$

Phase lag decreases Number of chances = $3/12$

Phase lag increases Number of chances = $3/12$

So the chance of making a 2-base gap worse is $(3/12)/(10/16+3/12)=28\%$ three gap sizes: 1-base gap heals (33% of population); 2-base gap gets wore only $1/3$ of gaps are 2 base, so 9% total get worse; 3-base gap also gets wo again 9% overall effect. In sum, 33% heal at a given reversal, 18% lose at a the remaining 50% are unchanged. Even assuming the 18% are permanent gap increased to a 3 base gap can still rejoin), at each subsequent reversal I strands are healed, which are unchanged by the previous reversal, as follow

| Reversal # | Fraction of gaps healed |
|---|---|
| 1 | 33% |
| 2 | 17% |
| 3 | 9% |
| 4 | 4.5% |
| 5 | 2.5% |
| 6 | 1% |
| Total | ~67% |

Therefore, repeated reversal of the dNTP probe cycle can reduce by $2/3$ the phase signals due to incorrect extension by nucleotide impurities, or random effectively increasing the read length when limited by either effect by a factor Although the invention has been described herein with reference to specific embodiments, many modifications and variations therein will readily occur to those skilled in the art. Accordingly, all such variations and modifications are included within the intended scope of the invention.

The invention claimed is:

1. A method for phase error compensation, comprising:
providing a plurality of template nucleic acid strands;
adding, in an order, individual types of deoxynucleoside triphosphates serially to the plurality of template nucleic acid strands to perform a series of nucleotide incorporation reactions;
after each nucleotide incorporation reaction of the series, detecting a signal transmitted from incorporation of nucleotides resulting from the adding of the deoxynucleoside triphosphates, the signal having an amplitude corresponding to a number of nucleotide incorporations; and
altering the order of the addition of the individual types of deoxynucleoside triphosphates to perform one or more subsequent nucleotide incorporation reactions, thereby compensating for phasing errors due to one or more out-of-phase template nucleic acid strand populations.

2. The method of claim 1, wherein the plurality of template nucleic acid strands are hybridized to a primer.

3. The method of claim 1, wherein the one or more out-of-phase template nucleic acid strand populations comprises a trailing fraction of the template nucleic acid strands that are out of phase relative to an in-phase fraction of the template nucleic acid strands because of extension failures.

4. The method of claim 3, further comprising monitoring the trailing fraction of the template nucleic acid strands to determine where and how to alter the order of addition of the individual types of deoxynucleoside triphosphates so as selectively to extend the trailing fraction of the template nucleic acid strands to bring them back into phase with the in-phase fraction of the template nucleic acid strands.

5. The method of claim 3, wherein altering the order of addition of the individual types of deoxynucleoside triphosphates comprises reversing the order of addition of the individual types of deoxynucleoside triphosphates at arbitrary intervals to bring back into phase about one-third of the trailing fraction of the template nucleic acid strands.

6. The method of claim 1, wherein the one or more out-of-phase template nucleic acid strand populations comprise a leading fraction of the template nucleic acid strands that are out of phase relative to an in-phase fraction of the template nucleic acid strands because of incorrect extensions.

7. The method of claim 6, wherein altering the order of addition of the individual types of deoxynucleoside triphosphates comprises reversing the order of addition of the individual types of deoxynucleoside triphosphates at arbitrary intervals to bring back into phase about two-thirds of the leading fraction of the template nucleic acid strands.

8. The method of claim 3, wherein the one or more out-of-phase template nucleic acid strand populations further comprise a leading fraction of the template nucleic acid strands that are out of phase relative to an in-phase fraction of the template nucleic acid strands because of incorrect extensions.

9. The method of claim 8, wherein altering the order of addition of the individual types of deoxynucleoside triphosphates comprises reversing the order of addition of the deoxynucleoside triphosphates at arbitrary intervals to bring back into phase about two-thirds of the leading fraction of the template nucleic acid strands.

10. A method for phase error compensation, comprising:
providing a plurality of template nucleic acid strands;
adding, in an order, individual types of deoxynucleoside triphosphates serially to the plurality of template nucleic acid strands to perform a series of nucleotide incorporation reactions;
after each nucleotide incorporation reaction of the series, detecting a signal transmitted from incorporation of nucleotides resulting from the adding of the deoxynucleoside triphosphates, the signal having an amplitude corresponding to a number of nucleotide incorporations; and
altering the order of the addition of the individual types of deoxynucleoside triphosphates to perform one or more subsequent nucleotide incorporation reactions, thereby compensating for phasing errors due to one or more out-of-phase template nucleic acid strand populations,
wherein the one or more out-of-phase template nucleic acid strand populations comprises a trailing fraction of the template nucleic acid strands that are out of phase relative to an in-phase fraction of the template nucleic acid strands because of extension failures, and
wherein altering the order of the addition of the individual types of deoxynucleoside triphosphates is based on monitoring the trailing fraction of the template nucleic acid strands to determine where to alter the order of addition of the deoxynucleoside triphosphates so as selectively to extend the trailing fraction of the template nucleic acid strands to bring them back into phase with the in-phase fraction of the template nucleic acid strands.

11. The method of claim 10, wherein the plurality of template nucleic acid strands are hybridized to a primer.

12. The method of claim 10, wherein altering the order of the addition of the individual types of deoxynucleoside triphosphates comprises reversing the order of addition of the individual types of deoxynucleoside triphosphates at arbitrary intervals to bring back into phase about one-third of the trailing fraction of template nucleic acid strands.

13. A method for phase error compensation, comprising:
providing a plurality of template nucleic acid strands;
adding, in an order, individual types of deoxynucleoside triphosphates serially to the plurality of template nucleic acid strands to perform a series of nucleotide incorporation reactions;
after each nucleotide incorporation reaction of the series, detecting a signal transmitted from incorporation of nucleotides resulting from the adding of the deoxynucleoside triphosphates, the signal having an amplitude corresponding to a number of nucleotide incorporations; and
altering the order of the addition of the individual types of deoxynucleoside triphosphates to perform one or more subsequent nucleotide incorporation reactions, thereby compensating for phasing errors due to one or more out-of-phase template nucleic acid strand populations,
wherein the one or more out-of-phase template nucleic acid strand populations comprise a leading fraction of the template nucleic acid strands that are out of phase relative to an in-phase fraction of the template nucleic acid strands because of incorrect extensions; and
wherein altering the order of addition of the individual types of deoxynucleoside triphosphates comprises reversing the order of addition of the individual types of deoxynucleoside triphosphates at arbitrary intervals.

14. The method of claim 13, wherein the plurality of template nucleic acid strands are hybridized to a primer.

* * * * *